(12) United States Patent
Grace et al.

(10) Patent No.: US 10,842,567 B2
(45) Date of Patent: *Nov. 24, 2020

(54) LASER-INDUCED FLUID FILLED BALLOON CATHETER

(71) Applicant: The Spectranetics Corporation, Colorado Springs, CO (US)

(72) Inventors: Kenneth P. Grace, Woodland Park, CO (US); Thomas Triffo, Colorado Springs, CO (US); James Cezo, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 474 days.

This patent is subject to a terminal disclaimer.

(21) Appl. No.: 15/476,183

(22) Filed: Mar. 31, 2017

(65) Prior Publication Data
US 2017/0265942 A1     Sep. 21, 2017

Related U.S. Application Data

(63) Continuation-in-part of application No. 14/984,050, filed on Dec. 30, 2015, now Pat. No. 10,201,387.
(Continued)

(51) Int. Cl.
*A61B 18/26* (2006.01)
*A61B 18/24* (2006.01)
(Continued)

(52) U.S. Cl.
CPC ............ *A61B 18/26* (2013.01); *A61B 18/245* (2013.01); *A61B 2017/22024* (2013.01);
(Continued)

(58) Field of Classification Search
CPC ....... A61B 18/245; A61B 18/26; A61B 18/20; A61B 2018/263; A61B 2018/00285;
(Continued)

(56) References Cited

U.S. PATENT DOCUMENTS 4,770,653 A     9/1988  Shturman
4,785,806 A    11/1988  Deckelbaum
(Continued)

FOREIGN PATENT DOCUMENTS

CN     103462688 A    12/2013
DE       2517019 A    10/1976
(Continued)

OTHER PUBLICATIONS

International Preliminary Report on Patentability issued in PCT/US2015/068161, dated Jul. 13, 2017, 15 pages.
(Continued)

*Primary Examiner* — Sarah A Simpson

(57) ABSTRACT

The present disclosure relates generally to the use of medical devices for the treatment of vascular conditions. In particular, the present disclosure provides devices and methods for using laser-induced pressure waves to disrupt vascular occlusions. The present disclosure not only provides devices and methods for using laser-induced pressure waves to disrupt vascular occlusions or portions thereof, but the present disclosure also provides devices and methods for disrupting calcium in the media and/or intima layer of an arterial wall.

19 Claims, 33 Drawing Sheets

Related U.S. Application Data which is a continuation-in-part of application No. 13/800,214, filed on Mar. 13, 2013, now Pat. No. 9,320,530.

(60) Provisional application No. 62/316,423, filed on Mar. 31, 2016, provisional application No. 62/098,242, filed on Dec. 30, 2014, provisional application No. 62/209,691, filed on Aug. 25, 2015, provisional application No. 62/232,318, filed on Sep. 24, 2015, provisional application No. 62/248,875, filed on Oct. 30, 2015, provisional application No. 62/248,913, filed on Oct. 30, 2015, provisional application No. 62/257,404, filed on Nov. 19, 2015, provisional application No. 62/261,085, filed on Nov. 30, 2015.

(51) Int. Cl.
    *A61B 18/00* (2006.01)
    *A61B 17/22* (2006.01)

(52) U.S. Cl.
    CPC ............ *A61B 2018/00285* (2013.01); *A61B 2018/00404* (2013.01); *A61B 2018/00577* (2013.01); *A61B 2018/263* (2013.01)

(58) Field of Classification Search
    CPC .. A61B 2018/0022; A61B 2018/00214; A61B 2017/22024
    See application file for complete search history.

(56) References Cited

U.S. PATENT DOCUMENTS

| | | |
|---|---|---|
| 4,793,359 A | 12/1988 | Sharrow |
| 4,832,023 A | 5/1989 | Murphy-Chutorian et al. |
| 4,862,886 A | 9/1989 | Clarke et al. |
| 4,878,492 A | 11/1989 | Sinofsky et al. |
| 4,966,596 A | 10/1990 | Kuntz et al. |
| 4,993,412 A | 2/1991 | Murphy-Chutorian |
| 5,010,886 A | 4/1991 | Passafaro et al. |
| 5,026,366 A | 6/1991 | Leckrone |
| 5,026,367 A | 6/1991 | Leckrone et al. |
| 5,029,588 A | 7/1991 | Yock et al. |
| 5,041,108 A | 8/1991 | Fox et al. |
| 5,053,033 A | 10/1991 | Clarke |
| 5,055,109 A | 10/1991 | Gould et al. |
| 5,176,674 A | 1/1993 | Hofmann |
| 5,192,278 A | 3/1993 | Hayes et al. |
| 5,281,212 A | 1/1994 | Savage et al. |
| 5,304,171 A | 4/1994 | Gregory et al. |
| 5,334,207 A | 8/1994 | Gay et al. |
| 5,350,375 A | 9/1994 | Deckelbaum et al. |
| 5,354,324 A | 10/1994 | Gregory |
| 5,383,199 A * | 1/1995 | Laudenslager ........ A61B 18/20 372/25 |
| 5,395,361 A | 3/1995 | Fox et al. |
| 5,423,805 A | 6/1995 | Brucker et al. |
| 5,468,239 A | 11/1995 | Tanner et al. |
| 5,470,330 A | 11/1995 | Goldenberg et al. |
| 5,573,531 A | 11/1996 | Gregory |
| 5,649,923 A | 7/1997 | Gregory et al. |
| 5,722,972 A | 3/1998 | Power et al. |
| 5,722,979 A | 3/1998 | Kusleika |
| 5,733,301 A | 3/1998 | Forman |
| 5,741,246 A | 4/1998 | Prescott |
| 5,769,843 A | 6/1998 | Abela et al. |
| 5,876,373 A | 3/1999 | Giba et al. |
| 5,876,397 A | 3/1999 | Edelman et al. |
| 5,944,687 A | 8/1999 | Benett et al. |
| 6,022,309 A | 2/2000 | Celliers et al. |
| 6,024,738 A | 2/2000 | Daikuzono et al. |
| 6,123,718 A | 9/2000 | Tu et al. |
| 6,132,423 A | 10/2000 | Aita et al. |
| 6,210,404 B1 | 4/2001 | Shadduck |
| 6,283,958 B1 | 9/2001 | Vogl et al. |
| 6,379,325 B1 | 4/2002 | Benett et al. |
| 6,551,302 B1 | 4/2003 | Rosinko et al. |
| 6,561,998 B1 | 5/2003 | Roth et al. |
| 6,592,612 B1 | 7/2003 | Samson et al. |
| 6,660,001 B2 | 12/2003 | Gregory |
| 6,752,800 B1 | 6/2004 | Winston et al. |
| 7,125,404 B2 | 10/2006 | Levatter |
| 7,144,248 B2 | 12/2006 | Irwin |
| 7,226,470 B2 | 6/2007 | Kemény et al. |
| 7,238,178 B2 | 7/2007 | Maschke |
| 7,306,585 B2 | 12/2007 | Ross |
| 7,818,053 B2 | 10/2010 | Kassab |
| 7,891,361 B2 | 2/2011 | Irwin |
| 8,104,483 B2 | 1/2012 | Taylor |
| 8,162,964 B2 | 4/2012 | Piippo et al. |
| 8,167,810 B2 | 5/2012 | Maschke |
| 8,396,548 B2 | 3/2013 | Perry |
| 8,454,669 B2 | 6/2013 | Irwin |
| 8,465,452 B2 | 6/2013 | Kassab |
| 8,551,096 B2 | 10/2013 | Perry et al. |
| 8,574,247 B2 | 11/2013 | Adams et al. |
| 8,684,970 B1 | 4/2014 | Koyfman et al. |
| 8,702,773 B2 | 4/2014 | Keeler |
| 8,709,075 B2 | 4/2014 | Adams et al. |
| 8,728,091 B2 | 5/2014 | Hakala et al. |
| 8,747,416 B2 | 6/2014 | Hakala et al. |
| 8,790,386 B2 | 7/2014 | Dwork |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,138,249 B2 | 9/2015 | Adams et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,320,530 B2 | 4/2016 | Grace |
| 2001/0027310 A1 | 10/2001 | Parisi et al. |
| 2003/0009157 A1 | 1/2003 | Levine |
| 2003/0181938 A1 | 9/2003 | Roth et al. |
| 2003/0229370 A1 | 12/2003 | Miller |
| 2004/0143287 A1 | 7/2004 | Konstantino |
| 2005/0021071 A1 | 1/2005 | Konstantino |
| 2005/0216044 A1 | 9/2005 | Hong |
| 2005/0240212 A1 | 10/2005 | McAuley |
| 2005/0251116 A1 | 11/2005 | Steinke et al. |
| 2006/0189930 A1 | 8/2006 | Lary et al. |
| 2006/0190022 A1 * | 8/2006 | Beyar ............... A61F 2/958 606/192 |
| 2007/0078500 A1 | 4/2007 | Ryan et al. |
| 2007/0093745 A1 | 4/2007 | Steward et al. |
| 2007/0198047 A1 | 8/2007 | Schon et al. |
| 2008/0103575 A1 | 5/2008 | Gerber |
| 2008/0249515 A1 | 10/2008 | Taylor |
| 2009/0112198 A1 | 4/2009 | Khanna et al. |
| 2009/0112239 A1 | 4/2009 | To |
| 2009/0270846 A1 | 10/2009 | Okada et al. |
| 2009/0270850 A1 | 10/2009 | Zhou et al. |
| 2010/0016862 A1 | 1/2010 | Hawkins et al. |
| 2010/0049182 A1 | 2/2010 | Ryan et al. |
| 2010/0152720 A1 | 6/2010 | Sauro et al. |
| 2010/0222786 A1 * | 9/2010 | Kassab ............. A61B 5/053 606/127 |
| 2011/0130708 A1 * | 6/2011 | Perry ............ A61B 18/1492 604/21 |
| 2011/0152683 A1 | 6/2011 | Gerrans et al. |
| 2011/0208185 A1 | 8/2011 | Diamant et al. |
| 2012/0116289 A1 | 5/2012 | Hawkins et al. |
| 2012/0203255 A1 | 8/2012 | Hawkins et al. |
| 2012/0221013 A1 * | 8/2012 | Hawkins ........... A61B 17/2202 606/128 |
| 2012/0303011 A1 | 11/2012 | Schaeffer |
| 2013/0030431 A1 | 1/2013 | Adams |
| 2013/0030447 A1 | 1/2013 | Adams |

(56) References Cited

U.S. PATENT DOCUMENTS

| | | |
|---|---|---|
| 2013/0046293 A1 | 2/2013 | Arai et al. |
| 2013/0096545 A1 | 4/2013 | Laudenslager et al. |
| 2013/0197555 A1 | 8/2013 | Schaer |
| 2014/0005576 A1 | 1/2014 | Adams et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052114 A1 | 2/2014 | Ben-Oren et al. |
| 2014/0052145 A1 | 2/2014 | Adams et al. |
| 2014/0074113 A1 | 3/2014 | Hakala et al. |
| 2014/0133814 A1 | 5/2014 | Stevens |
| 2014/0163592 A1 | 6/2014 | Hawkins et al. |
| 2014/0214061 A1 | 7/2014 | Adams |
| 2014/0276682 A1 | 9/2014 | Hendrick et al. |
| 2014/0288570 A1 | 9/2014 | Adams |
| 2015/0039002 A1 | 2/2015 | Hawkins |
| 2015/0073430 A1 | 3/2015 | Hakala et al. |
| 2015/0105714 A1 | 4/2015 | Laudenslager et al. |
| 2015/0238208 A1 | 8/2015 | Adams et al. |
| 2015/0238209 A1 | 8/2015 | Hawkins et al. |
| 2015/0320432 A1 | 11/2015 | Adams |
| 2017/0333132 A1 | 11/2017 | Grace et al. |
| 2018/0008348 A1 | 1/2018 | Grace et al. |

FOREIGN PATENT DOCUMENTS

| | | |
|---|---|---|
| DE | 4240182 C2 | 6/1994 |
| DE | 4437578 A1 | 5/1996 |
| EP | 0182689 B1 | 5/1986 |
| EP | 0189329 A3 | 7/1986 |
| EP | 0355200 A1 | 2/1990 |
| EP | 0820786 A2 | 1/1998 |
| EP | 0902654 B1 | 3/1999 |
| EP | 1200002 B1 | 5/2002 |
| JP | H01148278 A | 6/1989 |
| JP | 2004215862 A | 8/2004 |
| JP | 2009061083 A | 3/2009 |
| KR | 100996733 B1 | 11/2010 |
| WO | WO199006087 A | 6/1990 |
| WO | 1991010403 A1 | 7/1991 |
| WO | WO199745157 A | 12/1997 |
| WO | WO2000012168 A1 | 3/2000 |
| WO | 2003057060 A1 | 7/2003 |
| WO | WO2004060460 A2 | 7/2004 |
| WO | 2006006169 A2 | 1/2006 |
| WO | 2010054048 A2 | 5/2010 |
| WO | 2009152352 A8 | 12/2010 |
| WO | 2011006017 A1 | 1/2011 |
| WO | 2013070750 A1 | 5/2013 |
| WO | 2013169807 A1 | 11/2013 |
| WO | 2014004887 A1 | 1/2014 |
| WO | 2014025397 A1 | 2/2014 |
| WO | 2014025620 A1 | 2/2014 |
| WO | 2014025981 A1 | 2/2014 |
| WO | 2014028885 A1 | 2/2014 |
| WO | 2014043400 A1 | 3/2014 |
| WO | 2014163955 A1 | 10/2014 |
| WO | 2015017499 A1 | 2/2015 |
| WO | 2015034840 A8 | 5/2015 |
| WO | 2015171515 A1 | 11/2015 |

OTHER PUBLICATIONS

International Search Report and Written Opinion issued in PCT/US2015/068169, dated Jul. 13, 2017, 21 pages.
International Search Report and Written Opinion issued in PCT/US2017/043680, dated Oct. 31, 2017, 14 pages.
International Search Report and Written Opinion issued in PCT/US2017/043762, dated Oct. 31, 2017, 14 pages.
International Preliminary Report on Patentability issued in PCT/US2014/019268, dated Sep. 24, 2015, 9 pages.
International Search Report and Written Opinion issued in International Application No. PCT/US13/25147, dated Jun. 13, 2013, 11 pages.
International Search Report and Written Opinion issued in PCT/US2014/019268 dated Jun. 13, 2014, 13 pages.
International Search Report and Written Opinion issued in PCT/US2015/068161, dated May 4, 2016, 19 pages.
International Search Report and Written Opinion issued in PCT/US2015/068169, dated May 13, 2016, 28 pages.
International Search Report and Written Opinion issued in PCT/US2015/068170, dated May 13, 2016, 13 pages.
International Search Report and Written Opinion issued in PCT/US2015/068173, dated Apr. 19, 2016, 16 pages.
Supplemental European Search Report issued in EP Application 14778867, dated Aug. 10, 2016, 7 pages.
U.S. Appl. No. 14/984,050 entitled Laser-Induced Fluid Filled Balloon Catheter, filed Dec. 30, 2015.
U.S. Appl. No. 14/984,294 entitled Electrically-Induced Fluid Filled Balloon Catheter, filed Dec. 30, 2015.
U.S. Appl. No. 14/984,308 entitled Laser-Induced Pressure Wave Emitting Catheter Sheath, filed Dec. 30, 2015.
U.S. Appl. No. 14/984,710 entitled Electrically-Induced Pressure Wave Emitting Catheter Sheath, filed Dec. 30, 2015.
U.S. Appl. No. 15/090,736 entitled "Apparatus and Method for Balloon Angioplasty," filed Apr. 5, 2016.

* cited by examiner

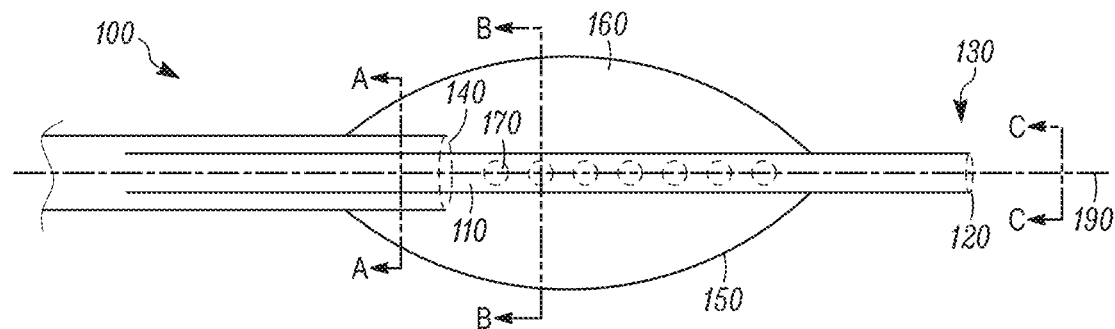
FIG. 1
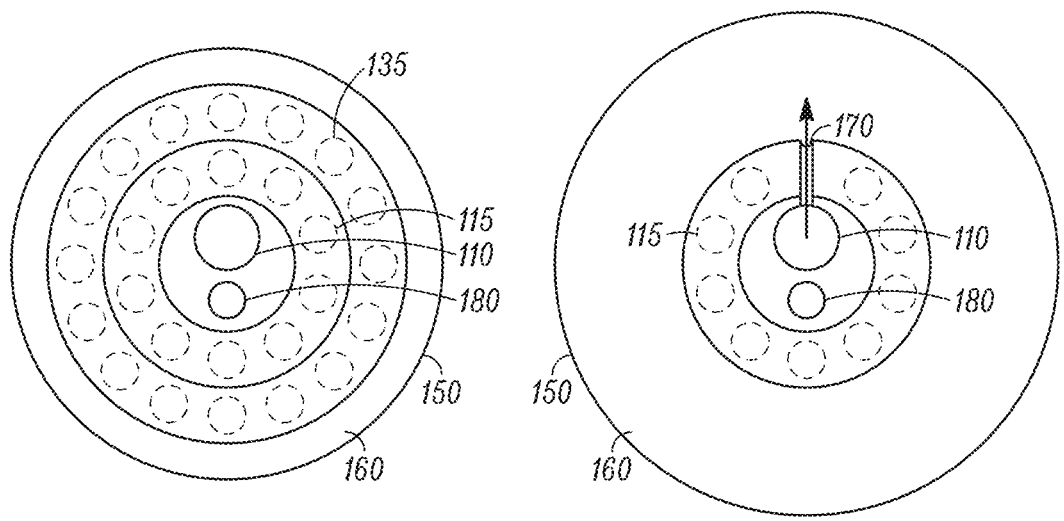
FIG. 1A
FIG. 1B
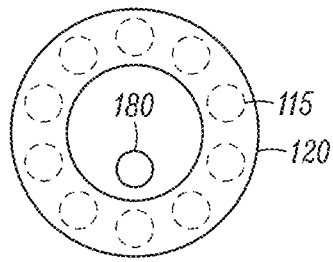
FIG. 1C

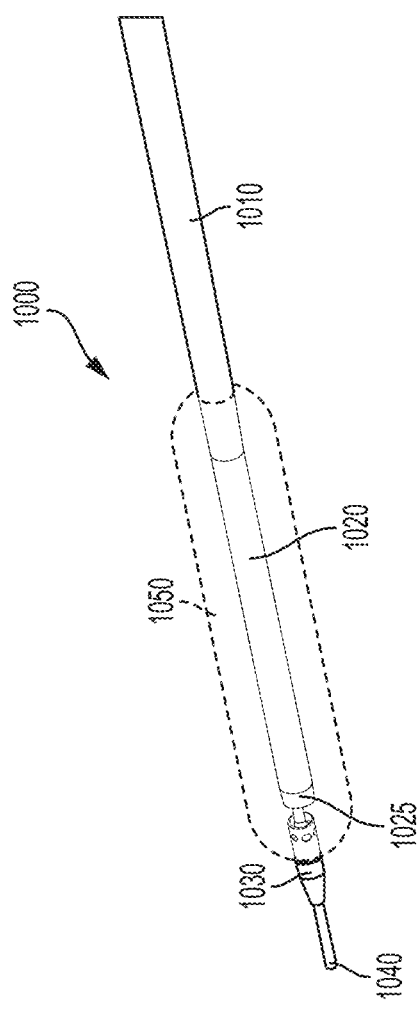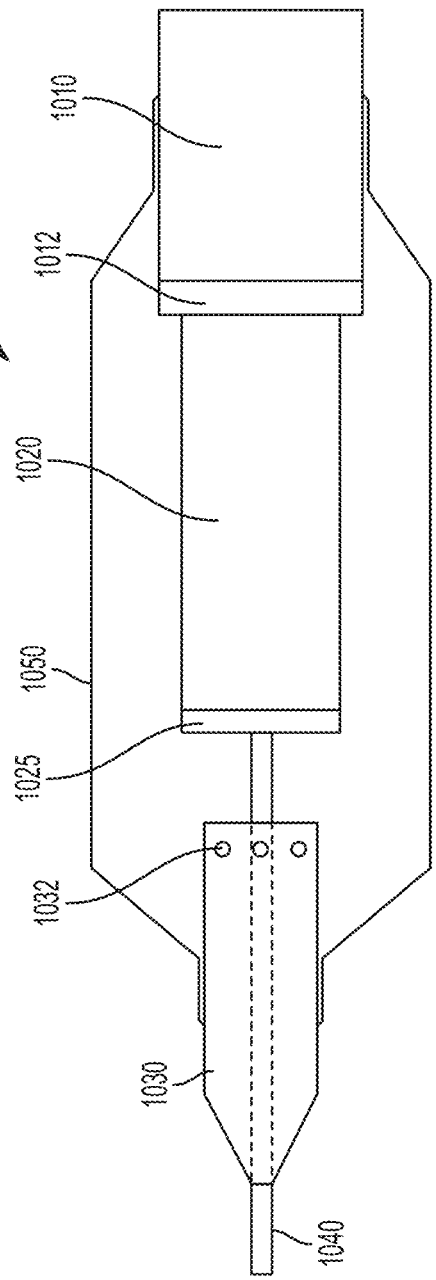
FIG. 10
FIG. 10A

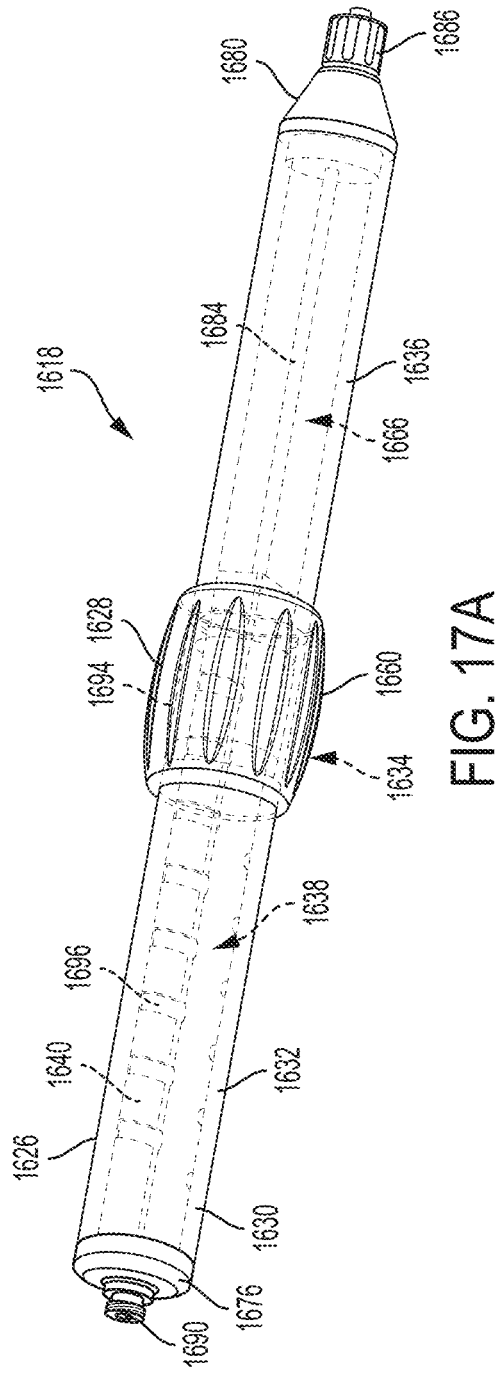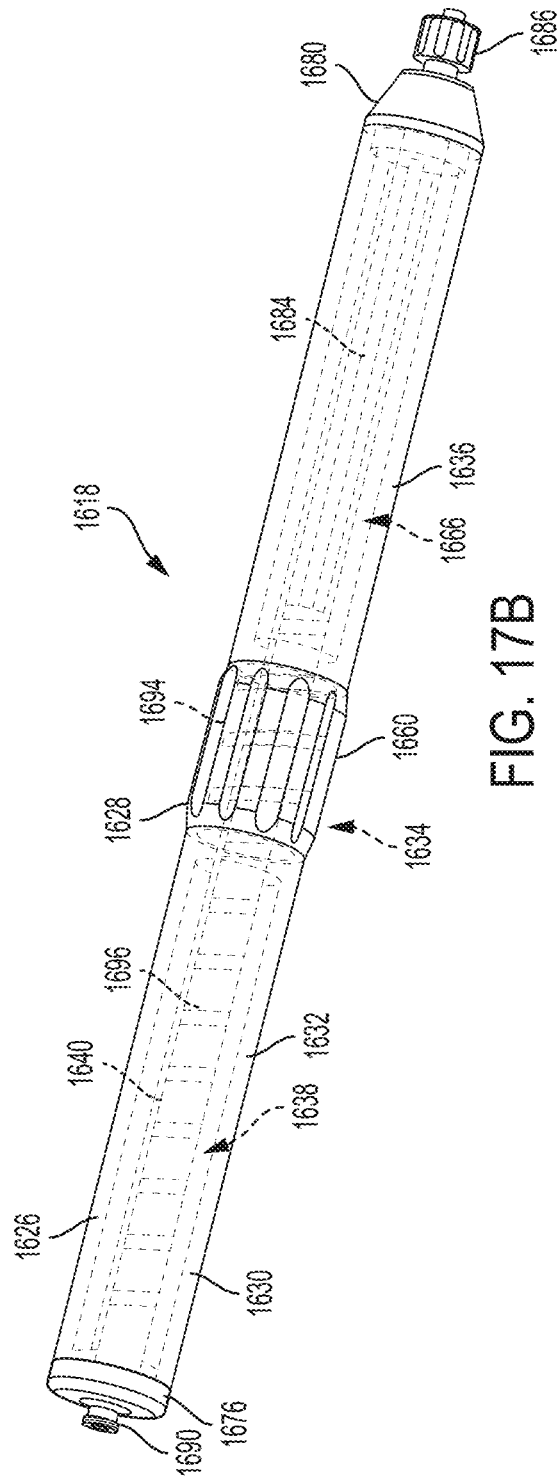
FIG. 17A
FIG. 17B

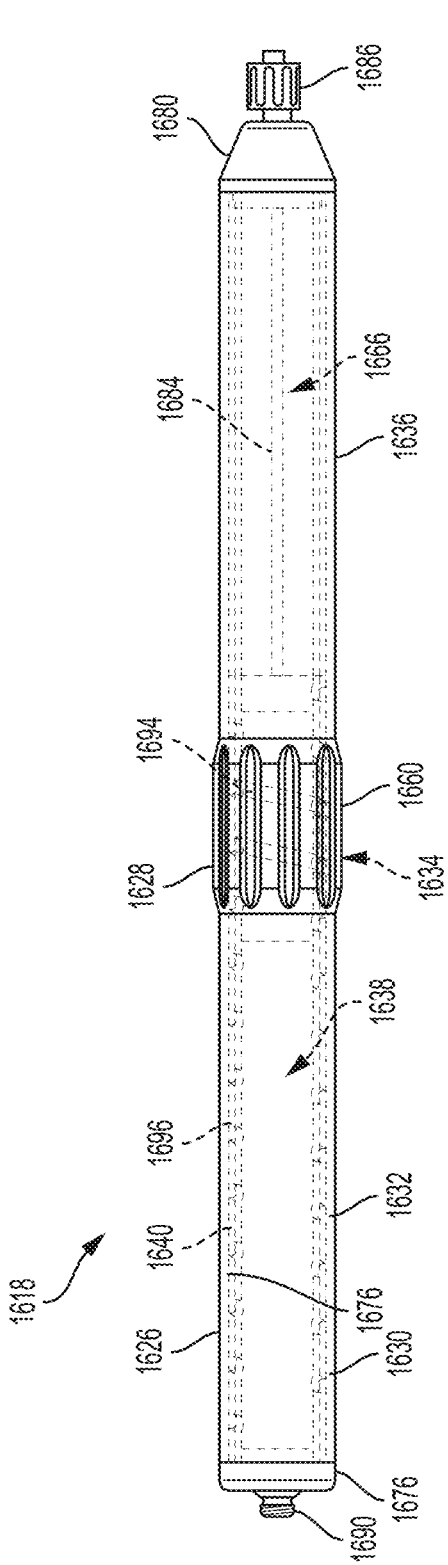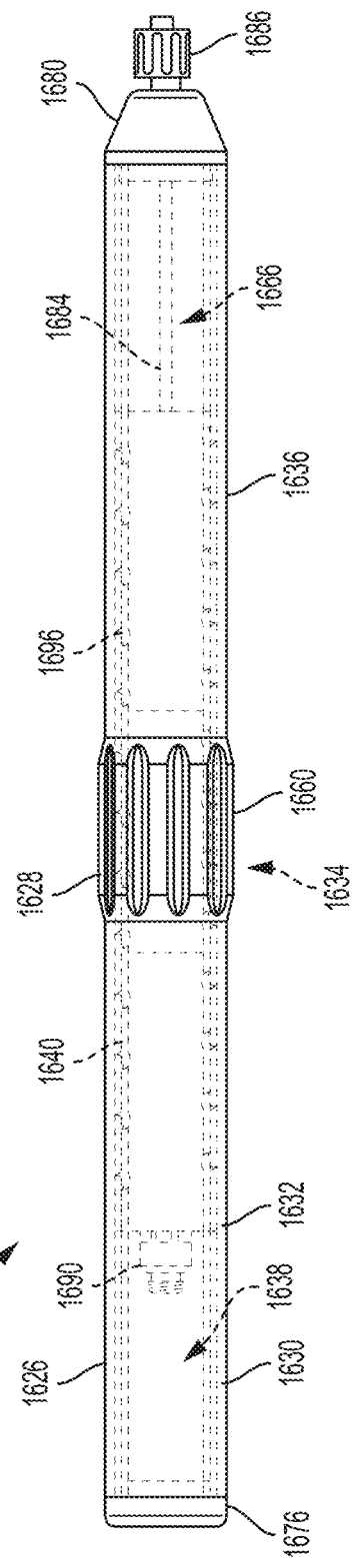

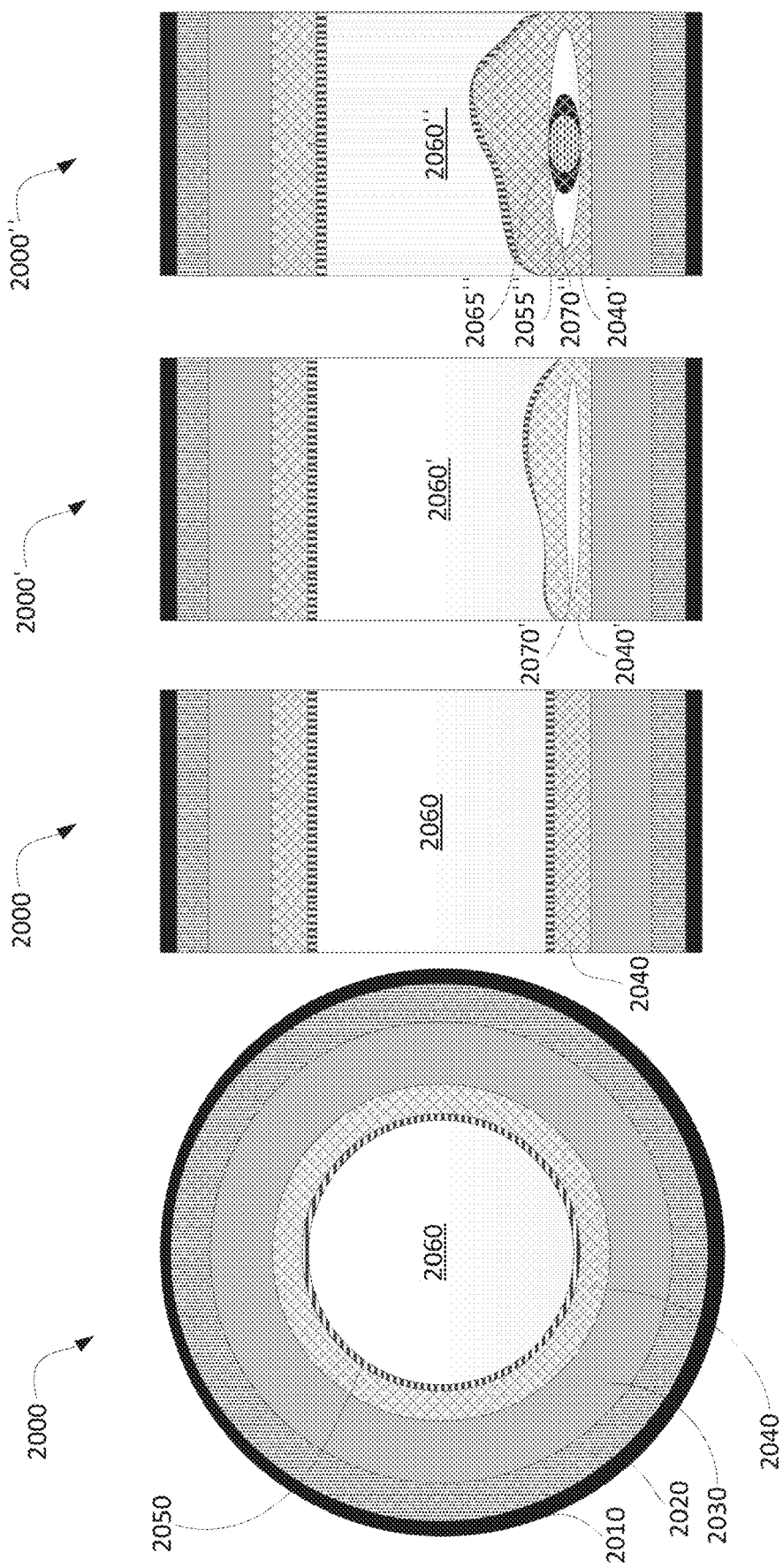

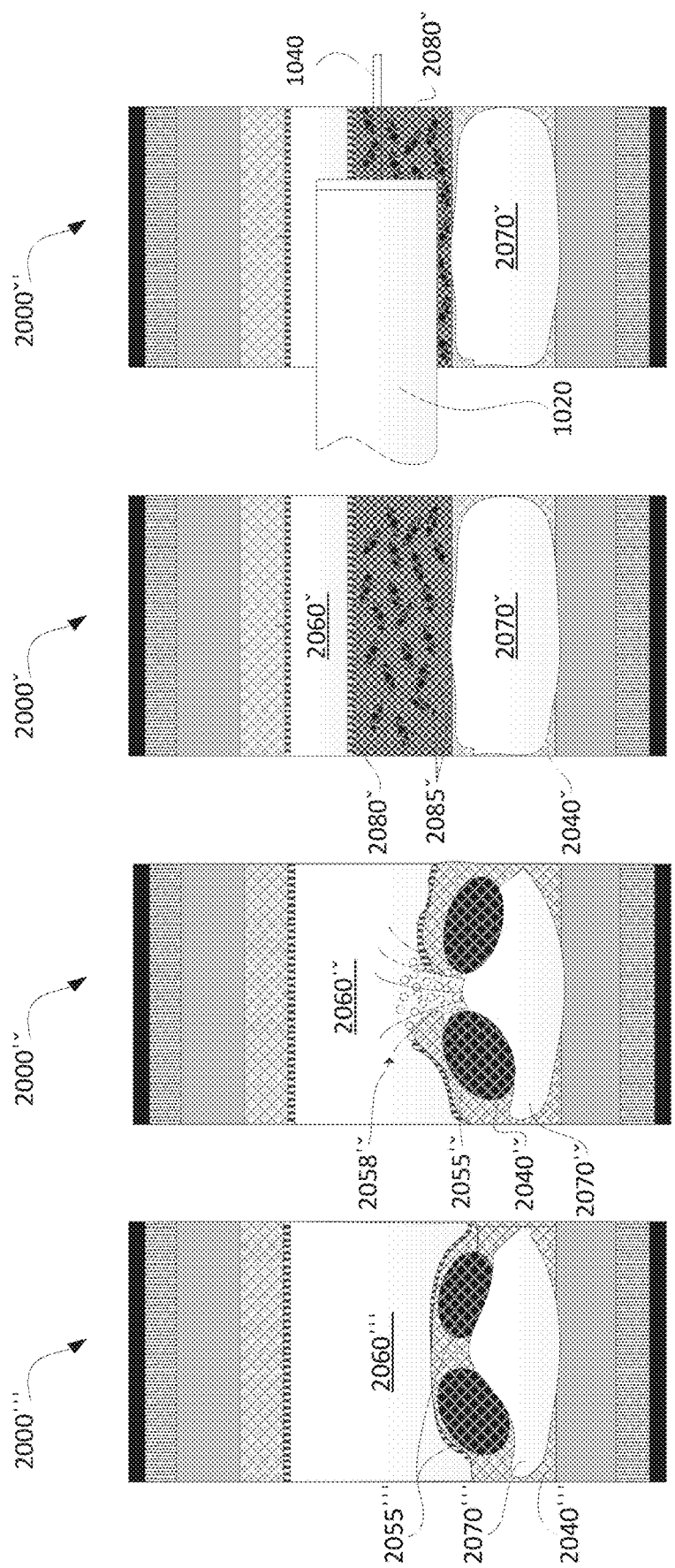

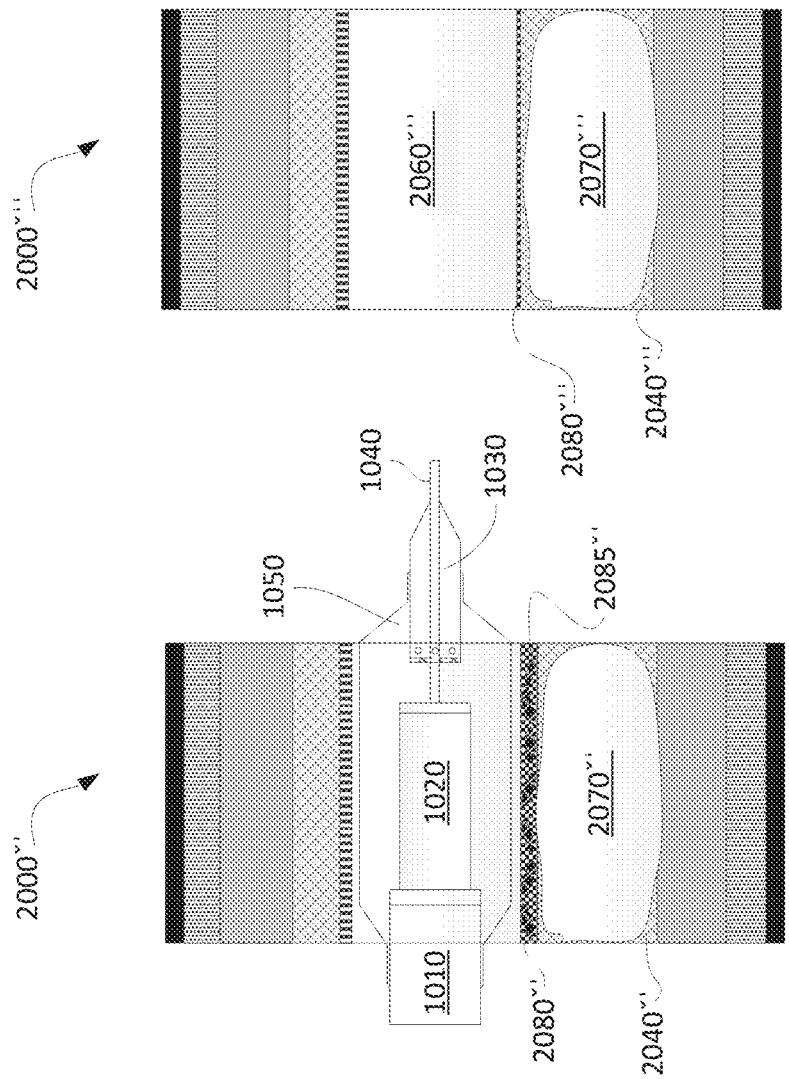

LASER-INDUCED FLUID FILLED BALLOON CATHETER

CROSS REFERENCE TO RELATED APPLICATIONS

The present application is a continuation-in-part of commonly assigned, co-pending U.S. application Ser. No. 14/984,050, filed on Dec. 30, 2015 which is hereby incorporated herein by reference in its entirety for all that it teaches and for all purposes, which is a continuation-in-part of commonly assigned, co-pending U.S. application Ser. No. 13/800,214, filed on Mar. 13, 2013, now U.S. Pat. No. 9,320,530, which is hereby incorporated herein by reference in its entirety for all that it teaches and for all purposes. U.S. application Ser. No. 14/984,050 claims the benefit of and priority, under 35 U.S.C. § 119(e), to commonly assigned, U.S. Application Ser. No. 62/098,242, filed on Dec. 30, 2014 which is hereby incorporated herein by reference in its entirety for all that it teaches and for all purposes. U.S. application Ser. No. 14/984,050 the benefit of and priority, under 35 U.S.C. § 119(e), to commonly assigned, U.S. Application Ser. No. 62/209,691, filed on Aug. 25, 2015 which is hereby incorporated herein by reference in its entirety for all that it teaches and for all purposes. U.S. application Ser. No. 14/984,050 claims the benefit of and priority, under 35 U.S.C. § 119(e), to commonly assigned, U.S. Application Ser. No. 62/232,318, filed on Sep. 24, 2015 which is hereby incorporated herein by reference in its entirety for all that it teaches and for all purposes. U.S. application Ser. No. 14/984,050 claims the benefit of and priority, under 35 U.S.C. § 119(e), to commonly assigned, U.S. Application Ser. No. 62/248,875, filed on Oct. 30, 2015 which is hereby incorporated herein by reference in its entirety for all that it teaches and for all purposes. U.S. application Ser. No. 14/984,050 claims the benefit of and priority, under 35 U.S.C. § 119(e), to commonly assigned, U.S. Application Ser. No. 62/248,913, filed on Oct. 30, 2015 which is hereby incorporated herein by reference in its entirety for all that it teaches and for all purposes. U.S. application Ser. No. 14/984,050 claims the benefit of and priority, under 35 U.S.C. § 119(e), to commonly assigned, U.S. Application Ser. No. 62/257,404, filed on Nov. 19, 2015 which is hereby incorporated herein by reference in its entirety for all that it teaches and for all purposes. U.S. application Ser. No. 14/984,050 claims the benefit of and priority, under 35 U.S.C. § 119(e), to commonly assigned, U.S. Application Ser. No. 62/261,085, filed on Nov. 30, 2015 which is hereby incorporated herein by reference in its entirety for all that it teaches and for all purposes. The present application claims the benefit of and priority, under 35 U.S.C. § 119(e), to commonly assigned, U.S. Application Ser. No. 62/316,423, filed on Mar. 31, 2016 which is hereby incorporated herein by reference in its entirety for all that it teaches and for all purposes.

FIELD

The present disclosure relates generally to the use of medical devices for the treatment of vascular conditions. In particular, the present disclosure provides materials and methods for using laser-induced pressure waves to disrupt vascular blockages and to deliver therapeutic agents to the blockage area.

BACKGROUND

Coronary artery disease (CAD) is the most common form of heart disease, affecting millions of people. Peripheral artery disease (PAD) also affects millions of people. CAD and PAD most often results from a condition known as atherosclerosis, which generally manifests as the accumulation of a waxy substance on the inside of a subject's arteries. This substance, called plaque, is made of cholesterol, fatty compounds, calcium, and a blood-clotting material called fibrin.

As the plaque builds up, the coronary and peripheral arteries narrows, or becomes stenotic, making it more difficult for blood to flow to the heart. As the blockage worsens in a person's coronary arteries, blood flow to the heart slows, and a condition called angina pectoris, or simply angina, may develop. Angina is like a squeezing, suffocating, or burning feeling in the chest. The pain typically develops when the heart requires additional blood, such as during exercise or times of emotional stress. In time, a narrowed or blocked artery can lead to a heart attack.

A number of medicines can be used to relieve the angina pain that comes with CAD, but these medicines cannot clear blocked arteries. A moderate to severely narrowed coronary artery may need more aggressive treatment to reduce the risk of a heart attack. Similarly, as the plaque builds up in peripheral arteries, the artery narrows, or becomes stenotic, thereby making it more difficult for blood to flow through the peripheral arteries. The reduced blood flow in the peripheral arties limits the amount of oxygen that is delivered to the extremities, which in turn may cause pain in the extremities and, in severe cases, gangrene, which may ultimately require amputation.

Balloon angioplasty and other transluminal medical treatments are well-known and have been proven efficacious in the treatment of stenotic lesions at the core of CAD and/or PAD. In a typical angioplasty procedure, a catheter is inserted into the groin or arm of a subject and guided to the affected arteries, such as the aorta and into the coronary arteries of the heart when treating CAD and the peripheral arteries when treating PAD. There, blocked arteries can be opened with a balloon positioned at the tip of the catheter.

Initially, angioplasty was performed only with balloon catheters, but technical advances have been made and improved patient outcomes have been achieved with the placement of small metallic spring-like devices called "stents" at the site of the blockage. The implanted stent serves as a scaffold that keeps the artery open. Angioplasty and stenting techniques are widely used around the world and provide an alternative option to bypass surgery for improving blood flow to the heart muscle. There are, however, limitations associated with angioplasty and stenting, one of which is called "restenosis."

Restenosis occurs when the treated vessel becomes blocked again. For example, when a stent is placed in a blood vessel, new tissue grows inside the stent, covering the struts of the stent. Initially, this new tissue consists of healthy cells from the lining of the arterial wall (such as, endothelium). This is a favorable effect because development of normal lining over the stent allows blood to flow smoothly over the stented area without clotting. Later, scar tissue may form underneath the new healthy lining. However, in about 25 percent of patients, the growth of scar tissue underneath the lining of the artery may be so thick that it can obstruct the blood flow and produce another blockage. "In-stent" restenosis is typically seen 3 to 6 months after the initial procedure. Another significant limitation of the use of stents is stent thrombosis, which, although rare (occurring in only 1 percent of patients), most commonly presents as acute myocardial infarction.

In addition to angioplasty and the deployment of stents, other types of intervention for stenotic vessels include atherectomy, bypass surgery, and the use of laser ablation and mechanical cutting systems to reduce the plaque size. Treatments using various pharmacological agents have also been developed, including medical infusions, drug-eluding stents (DES), and drug eluting balloons (DEB). Given the persistence of CAD and PAD, however, the most efficacious means for improving therapeutic outcomes may involve combinations of therapies designed not only to reduce plaque size in the short term, but also to prevent future complications such as restenosis. Combinatorial therapies may offer the best chance to improve therapeutic outcomes for people suffering from CAD and PAD.

SUMMARY

These and other needs are addressed by the various aspects, embodiments, and configurations of the present disclosure.

The present disclosure provides a catheter comprising of a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium.

A catheter, wherein the at least one emitter is configured to emit laser light energy at wavelengths between about 300 nanometers to about 350 nanometers, at pulse durations between about 100 nanoseconds to about 150 nanoseconds, and at frequencies between about 1 pulse per second to about 250 pulses per second.

A catheter, wherein the at least one emitter is configured to emit laser light energy at wavelengths of about 308 nanometers, at pulse durations between about 120 nanoseconds and about 140 nanoseconds, and at frequencies between about 25 pulses per second to about 80 pulses per second.

A catheter, wherein the total energy output for the at least one emitter is between about 30 to about 80 millijoules per millimeter squared (mJ/mm$^2$).

A catheter, wherein the total energy output for the at least one emitter may be between about 20 to about 1000 millijoules per millimeter squared (mJ/mm$^2$).

A catheter further comprising additional emitters within the catheter, the additional emitters having a distal end corresponding to the distal end of the catheter, the distal end of the additional emitters being disposed distally of the balloon catheter.

A catheter, wherein the distal end of the additional emitters are configured to emit laser light energy at wavelengths between about 300 nanometers to about 350 nanometers, at pulse durations between about 100 nanoseconds to about 150 nanoseconds, and at frequencies between about 1 pulse per second to about 250 pulses per second.

A catheter, wherein the distal end of the additional emitters are configured to emit laser light energy at wavelengths of about 308 nanometers, at pulse durations between about 120 nanoseconds and about 140 nanoseconds, and at frequencies between about 25 pulses per second to about 80 pulses per second.

A catheter, wherein the liquid medium is contrast medium or contrast solution.

A catheter, wherein the liquid medium is any one of iodine-containing contrast medium or gadolinium contrast medium.

A catheter, wherein the liquid medium is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 1000 pulses per second.

A catheter, wherein the liquid medium is delivered into the balloon to create a pressure greater than 0.0 atmospheres to about 20.0 atmospheres within the balloon catheter.

A catheter, wherein the at least one emitter is two or more concentric emitters.

A catheter, wherein the at least one emitter is two or more single emitters.

A catheter, wherein the at least one emitter is configured to translate within the balloon catheter.

The present disclosure provides a method for treating an obstruction or restriction within the vasculature of a subject, the method comprising positioning a catheter within the vasculature of a subject, the catheter comprising a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium, positioning the balloon adjacent to an obstruction or restriction within the vasculature, inflating the balloon by delivering a liquid medium through an inner lumen of the catheter and out one or more liquid medium ports into the balloon until a desired inflation pressure is obtained, and activating the at least one energy source to emit one or more pulses of light energy from the at least one emitter within the balloon, wherein emitting the one or more pulses of light energy from the at least one emitter reacts with the liquid medium and generates a plurality of propagating laser-induced pressure waves that engage and disrupt at least a portion of the vascular obstruction or restriction.

A method, wherein the at least one emitter is configured to emit light energy at wavelengths of between about 300 nanometers to about 350 nanometers, at pulse durations between about 100 nanoseconds to about 150 nanoseconds, and at frequencies between about 1 pulse per second to about 250 pulses per second.

A method, wherein the at least one emitter is configured to emit laser light energy at wavelengths of about 308 nanometers, at pulse durations between about 120 nanoseconds and about 140 nanoseconds, and at frequencies between about 25 pulses per second to about 80 pulses per second.

A method, wherein the liquid medium is any one of iodine-containing contrast medium or gadolinium contrast medium.

A method, wherein the inflation pressure obtained by delivering liquid medium into the dilation balloon catheter is between about 0.25 atmospheres and about 5.0 atmospheres of pressure.

The present disclosure provides a method for treating an obstruction or restriction within the vasculature of a subject, the method comprising positioning a catheter within the vasculature of a subject, the catheter comprising a lumen, a proximal end and a distal end, one or more emitters circumferentially arranged around or adjacent to the lumen, a balloon circumferentially arranged around a portion of the catheter, wherein at least a portion of the balloon is coated with one or more therapeutic agents, at least one energy source coupled to the at least one emitter, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium, positioning the balloon adjacent to an obstruction or restriction within the vasculature, inflating the balloon by delivering a liquid medium through an inner lumen of the catheter and out one or more liquid medium ports into the balloon until a desired inflation pressure is obtained, and activating the at least one energy source to emit one or more pulses of light energy from the at least one emitter within the balloon, wherein emitting the one or more pulses of light energy from the at least one emitter reacts with the liquid medium and generates a plurality of propagating laser-induced pressure waves that delivers the one or more therapeutic agents to the vascular obstruction or restriction or to the tissues surrounding the vascular obstruction or restriction.

A method, wherein the plurality of propagating laser-induced pressure waves enhances the penetration of the one or more therapeutic agents into the vascular obstruction or restriction or into the tissues surrounding the vascular obstruction or restriction.

A method, wherein the at least one emitter is configured to emit light energy at wavelengths of between about 300 nanometers to about 350 nanometers, at pulse durations between about 100 nanoseconds to about 150 nanoseconds, and at frequencies between about 1 pulse to about 250 pulses per second.

A method, wherein the at least one emitter is configured to emit laser light energy at wavelengths of about 308 nanometers, at pulse durations between about 120 nanoseconds and about 140 nanoseconds, and at frequencies between about 25 pulses per second to about 80 pulses per second.

A method, wherein the liquid medium is contrast medium or contrast solution, wherein the liquid medium is any one of iodine-containing contrast medium or gadolinium contrast medium, and/or wherein the liquid medium is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 1000 pulses per second.

A method, wherein the liquid medium is delivered into the balloon catheter to create a pressure greater than 0.0 atmospheres to about 20.0 atmospheres within the balloon catheter.

A method, wherein the one or more therapeutic agents comprises one or more oxidation-insensitive drugs in a polymer-free drug preparation.

A method, wherein the one or more oxidation-insensitive drugs is one or more of taxanes, thalidomide, statins, corticoids, and lipophilic derivatives of corticoids.

The present disclosure also provides a catheter having a guidewire lumen, an inflation lumen, a proximal end and a distal end, one or more emitters circumferentially arranged around or adjacent to the lumen, a balloon circumferentially arranged around a portion of the catheter, at least one energy source coupled to the at least one emitter, a means for directing a laser-induced pressure wave and/or cavitation event towards the guidewire lumen or a guidewire within the guidewire lumen, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium.

A catheter, wherein the means for directing a laser-induced pressure wave and/or cavitation event towards the guidewire lumen or a guidewire within the guidewire lumen comprises an outer band coupled to the distal end of the catheter, wherein the outer band comprises a distal end, and the emitter is disposed proximate the distal end of the outer band. A catheter, wherein the emitter is directed at the guidewire lumen or a guidewire.

A catheter, wherein the means for directing a laser-induced pressure wave and/or cavitation event towards the guidewire lumen or a guidewire comprises a cap coupled to the distal end of the catheter.

A catheter, wherein the cap is configured to direct a laser-induced pressure wave and/or cavitation event towards the guidewire lumen or a guidewire within the guidewire lumen.

A catheter, wherein cap comprises an interior side and an exterior side, wherein the interior side is tapered to direct a laser-induced pressure wave and/or cavitation event towards the guidewire lumen or a guidewire within the guidewire lumen.

A catheter, wherein emitter is disposed proximate the interior side of the cap.

A catheter, wherein the at least one emitter is configured to emit laser light energy at wavelengths of between about 300 nanometers to about 350 nanometers, at pulse durations between about 100 nanoseconds to about 150 nanoseconds, and at frequencies between about 1 pulse per second to about 250 pulses per second.

A catheter, wherein the at least one emitter is configured to emit laser light energy at wavelengths of about 308 nanometers, at pulse durations between about 120 nanoseconds and about 140 nanoseconds, and at frequencies between about 25 pulses per second to about 80 pulses per second.

A catheter, wherein total energy output for the at least one emitter is between about 30 to about 80 millijoules per millimeter squared (mJ/mm$^2$).

A catheter, wherein the liquid medium is contrast medium or contrast solution.

A catheter, wherein the liquid medium is any one of iodine-containing contrast medium or gadolinium contrast medium.

A catheter, wherein the liquid medium is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 1000 pulses per second.

A catheter, wherein the means for directing a laser-induced pressure wave and/or cavitation event towards the guidewire lumen or a guidewire within the guidewire lumen comprises pressure-wave reflective material in the balloon catheter such that upon the laser-induced pressure wave and/or vapor bubble reaching the pressure-wave reflective material in the balloon catheter, the reflective material directs the laser-induced pressure wave and/or cavitation event toward the guidewire lumen and/or guidewire to excite and/or vibrate the guidewire.

A catheter, wherein the cavitation event occurs on a guidewire within the guidewire lumen, resulting in excitation and/or vibration of the guidewire.

The present disclosure also provides a method for treating an obstruction or restriction within vasculature of a subject, the method comprising positioning a catheter within vasculature of a subject, the catheter having a guidewire lumen, an inflation lumen, a proximal end and a distal end, one or more emitters circumferentially arranged around or adjacent to the lumen, a balloon circumferentially arranged around a portion of the catheter, at least one energy source coupled to the at least one emitter, a means for directing a laser-induced pressure wave and/or cavitation event towards the guidewire lumen or a guidewire within the guidewire lumen, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium, positioning the balloon adjacent to an obstruction or restriction within the vasculature, inflating the balloon by delivering a liquid medium through an inner lumen of the catheter and out one or more liquid medium ports into the balloon until a desired inflation pressure is obtained, and activating the at least one energy source to emit one or more pulses of light energy from the at least one emitter within the balloon, wherein emitting the one or more pulses of light energy from the at least one emitter reacts with the liquid medium and generates a plurality of propagating laser-induced pressure waves that engage and disrupt at least a portion of the vascular obstruction or restriction, and wherein the means for directing laser-induced pressure wave and/or cavitation event towards the guidewire lumen or a guidewire within the guidewire lumen induces vibrations within the guidewire.

A method, wherein the means for directing laser-induced pressure wave and/or cavitation event towards the guidewire lumen or a guidewire within the guidewire lumen comprises an outer band coupled to the distal end of the catheter, wherein the outer band comprises a distal end, and the emitter is disposed proximate the distal end of the outer band.

A method, wherein the emitter is directed at the guidewire lumen or a guidewire.

A method, wherein the means for directing laser-induced pressure wave and/or cavitation event towards the guidewire lumen or a guidewire comprises a cap coupled to the distal end of the catheter.

A method, wherein the cap is configured to for directing laser-induced pressure wave and/or cavitation event towards the guidewire lumen or a guidewire within the guidewire lumen.

A method, wherein cap comprises an interior side and an exterior side, wherein the interior side is tapered to direct the laser-induced pressure wave and/or cavitation event towards the guidewire lumen or a guidewire within the guidewire lumen.

A method, wherein emitter is disposed proximate the interior side of the cap.

A method, wherein the balloon is deflated and the positioning, inflating, and activating steps are repeated.

The present disclosure also provides a catheter comprising a catheter having a first guidewire lumen, a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium, a sealable valve having a second guidewire lumen and a seal, a balloon having a proximal end and distal end, wherein the proximal end of the balloon is coupled to the distal end of the catheter, wherein the distal end of the balloon is coupled to the sealable valve, and whereupon introducing a guidewire into the first guidewire lumen and the second guidewire lumen and introducing liquid medium through the inflation lumen and into the balloon, the liquid medium actuates the seal within the valve and closes an opening between the valve and the guidewire.

The catheter, wherein the sealable valve further comprises an exterior wall and a flange disposed radially therein, wherein a gap exists between the exterior wall and the flange.

The catheter, wherein the sealable valve comprises a proximal portion and a distal portion, and wherein the flange is disposed toward the proximal end of the sealable valve.

The catheter, wherein the proximal portion of the sealable valve is tubular.

The catheter, wherein the distal portion of the sealable valve is tapered radially inward from the exterior wall towards the second guidewire lumen.

The catheter, wherein sealable valve further comprises openings within the exterior wall toward the proximal portion.

The catheter, wherein the flange is tapered radially inward towards the second guidewire lumen as the flange progresses from the distal portion toward the proximal portion.

The present disclosure also provides a system for treating an obstruction or restriction within vasculature of a subject, the system comprising a catheter with a first guidewire lumen, a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium, a sealable valve having a second guidewire lumen and a seal, a balloon having a proximal end and distal end, wherein the proximal end of the balloon is coupled to the distal end of the catheter, wherein the distal end of the balloon is coupled to the sealable valve, and whereupon introducing a guidewire into the first guidewire lumen and the second guidewire lumen and introducing liquid medium through the inflation lumen and into the balloon, the liquid medium actuates the seal within the valve and closes an opening between the valve and the guidewire, and a laser catheter comprising a proximal portion, distal portion, at least one or more emitters disposed therein, wherein the at least one or more emitters extend from the proximal portion, wherein the proximal portion is coupled to an energy source, wherein the at least one emitter is disposed within the balloon.

The system and the catheter, wherein the at least one emitter is configured to emit laser light energy at wavelengths of between about 300 nanometers to about 350 nanometers, at pulse durations between about 100 nanoseconds to about 150 nanoseconds, and at frequencies between about 1 pulse per second to about 250 pulses per second.

The system and the catheter, wherein the at least one emitter is configured to emit laser light energy at wavelengths of about 308 nanometers, at pulse durations between about 120 nanoseconds and about 140 nanoseconds, and at frequencies between about 25 pulses per second to about 80 pulses per second.

The system and the catheter, wherein total energy output for the at least one emitter is between about 30 to about 80 millijoules per millimeter squared (mJ/mm2).

The present disclosure also provides a method for treating an obstruction or restriction within vasculature of a subject, the method comprising positioning a guidewire within vasculature of a subject, positioning a catheter within the vasculature of a subject over the guidewire, the catheter comprising a comprising a catheter with a first guidewire lumen, a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium, a sealable valve having a second guidewire lumen and a seal, a balloon having a proximal end and distal end, wherein the proximal end of the balloon is coupled to the distal end of the catheter, wherein the distal end of the balloon is coupled to the sealable valve, and whereupon introducing a guidewire into the first guidewire lumen and the second guidewire lumen and introducing liquid medium through the inflation lumen and into the balloon, the liquid medium actuates the seal within the valve and closes an opening between the valve and the guidewire, and introducing at least one emitter into the balloon, activating the at least one energy source to emit one or more pulses of light energy from the at least one emitter within the balloon, wherein emitting the one or more pulses of light energy from the at least one emitter reacts with the liquid medium and generates a plurality of propagating laser-induced pressure waves that engage and disrupt at least a portion of the vascular obstruction or restriction.

The method, wherein the at least one emitter is configured to emit laser light energy at wavelengths of between about 300 nanometers to about 350 nanometers, at pulse durations between about 100 nanoseconds to about 150 nanoseconds, and at frequencies between about 1 pulse per second to about 250 pulses per second.

The method, wherein the at least one emitter is configured to emit laser light energy at wavelengths of about 308 nanometers, at pulse durations between about 120 nanoseconds and about 140 nanoseconds, and at frequencies between about 25 pulses per second to about 80 pulses per second.

The method, wherein total energy output for the at least one emitter is between about 30 to about 80 millijoules per millimeter squared (mJ/mm$^2$).

The method, wherein the liquid medium is contrast medium or contrast solution.

The method, wherein the liquid medium is any one of iodine-containing contrast medium or gadolinium contrast medium.

The method, wherein the liquid medium is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 1000 pulses per second.

According to the present disclosure, the method(s) include delivering one or more therapeutic agents comprising one or more oxidation-insensitive drugs in a polymer-free drug preparation, including one or more of taxanes, thalidomide, statins, corticoids, and lipophilic derivatives of corticoids. The therapeutic agents may also include one or more lipophilic antioxidants, such as nordihydroguaiaretic acid, resveratrol and propyl gallate in a polymer-free preparation. For example, U.S. application Ser. No. 13/628,608, which is a continuation of International Application No. PCT/EP2010/066754, filed Nov. 3, 2010, both of which are hereby incorporated herein by reference in their entireties for all that they teach and for all purposes, discloses a scoring or cutting balloon catheter providing improved adherence of therapeutic agents to the balloon catheter using a combination of an oxidation-insensitive drug and a lipophilic antioxidant.

Additionally, U.S. application Ser. No. 13/707,401, filed Dec. 6, 2012, and issued on Oct. 21, 2014, which is a divisional application of U.S. application Ser. No. 11/411,635, filed Apr. 26, 2006, and which claims priority to U.S. Provisional Application Ser. No. 60/680,450, filed May 11, 2005, all of which are hereby incorporated herein by reference in their entireties for all that they teach and for all purposes, discloses scoring elements of a balloon catheter coated with a polymer matrix to deliver hydrophobic and lipophilic drugs to regions within a thrombus or plaque.

Additionally, U.S. application Ser. No. 13/310,320, filed Dec. 2, 2011, and issued Oct. 22, 2013, which is a divisional application of U.S. application Ser. No. 12/712,134, filed Feb. 24, 2010, and issued Mar. 6, 2012, and U.S. application Ser. No. 12/726,101, filed Mar. 17, 2010, and issued Feb. 14, 2012, which is a continuation-in-part of U.S. application Ser. No. 12/712,134, filed Feb. 24, 2010, and issued Mar. 6, 2012, which is a continuation-in-part of U.S. application Ser. No. 12/558,420, filed Sep. 11, 2009, which is a continuation-in-part of U.S. application Ser. No. 12/210,344, filed Sep. 15, 2008, and issued Sep. 4, 2012, and U.S. application Ser. No. 14/149,862, filed Jan. 8, 2014, which is a continuation of U.S. application Ser. No. 13/560,538, filed Jun. 27, 2012, and issued Mar. 18, 2014, which is a divisional application of U.S. application Ser. No. 12/210,344, filed Sep. 15, 2008, and issued Sep. 4, 2012, all of which are hereby incorporated herein by reference in their entireties for all that they teach and for all purposes, disclose methods and devices for local delivery of water-soluble and water-insoluble therapeutic agents to the surface of normal and diseased body lumens.

Additionally, U.S. application Ser. No. 13/926,515, filed Jun. 25, 2013, which claims priority to U.S. Provisional Application Ser. No. 61/665,758, filed Jun. 28, 2012, both of which are hereby incorporated herein by reference in their entireties for all that they teach and for all purposes, disclose methods and devices for coating a medical device that includes a therapeutic agent dispersed in a polymer or oligomer matrix.

The present disclosure also provides a catheter comprising a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more inflation ports disposed about the catheter and within the balloon, wherein said inflation ports are used to fill the balloon with a inflation medium, and a light absorbing material located within the balloon catheter such that the light absorbing material interacts with light emitted from at least one emitter.

A catheter, wherein the at least one emitter is configured to emit laser light energy at wavelengths of between about 300 nanometers to about 350 nanometers, at pulse durations between about 100 nanoseconds to about 150 nanoseconds, and at frequencies between about 1 pulse per second to about 250 pulses per second.

A catheter, wherein the at least one emitter is configured to emit laser light energy at wavelengths of about 308 nanometers, at pulse durations between about 120 nanoseconds and about 140 nanoseconds, and at frequencies between about 25 pulses per second to about 80 pulses per second.

A catheter, wherein total energy output for the at least one emitter is between about 30 to about 80 millijoules per millimeter squared (mJ/mm$^2$).

A catheter further comprising additional emitters within the catheter, the additional emitters having a distal end corresponding to the distal end of the catheter, the distal end of the additional emitters being disposed distally of the balloon catheter A catheter, wherein the additional emitters within the catheter are configured to emit laser light energy at wavelengths between about 300 nanometers to about 350 nanometers, at pulse durations between about 100 nanoseconds to about 150 nanoseconds, and at frequencies between about 1 pulse per second to about 250 pulses per second.

A catheter, wherein the one or more inflation medium ports are used to deliver an inflation medium into the balloon catheter to inflate the balloon catheter.

A catheter, wherein the inflation medium is a liquid medium comprising saline, or wherein the inflation medium is a gas medium comprising an inert gas.

A catheter, wherein the light absorbing material is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 1000 pulses per second.

A catheter, wherein the light absorbing material is applied as a coating to a support structure located within the balloon catheter.

A catheter, wherein the at least one emitter is two or more concentric emitters.

A catheter, wherein the at least one emitter is two or more single-fiber emitters.

A catheter, wherein the at least one emitter is configured to translate within the balloon catheter.

The present disclosure also provides a method for treating an obstruction or restriction within vasculature of a subject. The method comprises positioning a catheter within vasculature of a subject, a catheter comprising a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more inflation ports disposed about the catheter and within the balloon, wherein said inflation ports are used to fill the balloon with a inflation medium, and a light absorbing material located within the balloon catheter such that the light absorbing material interacts with light emitted from at least one emitter. The method also provides positioning the balloon catheter adjacent an obstruction or restriction within the vasculature, inflating the balloon catheter by delivering inflation medium through an inner lumen of the catheter and out one or more inflation medium ports into the balloon catheter until a desired inflation pressure is obtained, and activating the at least one emitter within the balloon catheter to transmit a pulse of light energy such that the light energy interacts with at least a portion of the light absorbing material, wherein the light energy reacts with the light absorbing material to generate a plurality of pressure waves which engage and disrupt at least a portion of the vascular obstruction or restriction.

The method, wherein the at least one emitter is configured to emit light energy at wavelengths of between about 300 nanometers to about 350 nanometers, at pulse durations between about 100 nanoseconds to about 150 nanoseconds, and at frequencies between about 1 pulse per second to about 250 pulses per second.

The method, wherein the light absorbing material is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 1000 pulses per second.

The method, wherein the light absorbing material is applied as a coating to a support structure located within the balloon catheter.

The present disclosure also provides a method for treating an obstruction or restriction within vasculature of a subject. The method comprises positioning a catheter within vasculature of a subject, a catheter comprising a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more inflation ports disposed about the catheter and within the balloon, wherein said inflation ports are used to fill the balloon with a inflation medium, and a light absorbing material located within the balloon catheter such that the light absorbing material interacts with light emitted from at least one emitter. The method also provides positioning the balloon catheter adjacent an obstruction or restriction within the vasculature, inflating the balloon catheter by delivering inflation medium through an inner lumen of the catheter and out one or more inflation medium ports into the balloon catheter until a desired inflation pressure is obtained, and activating the at least one emitter within the balloon catheter to transmit a pulse of light energy such that the light energy interacts with at least a portion of the light absorbing material, wherein the light energy reacts with the light absorbing material to generate a plurality of pressure waves that deliver one or more therapeutic agents to the vascular obstruction or restriction or to the tissues surrounding the vascular obstruction or restriction.

The method, wherein the plurality of pressure waves enhances the penetration of the one or more therapeutic agents into the vascular obstruction or restriction or into the tissues surrounding the vascular obstruction or restriction.

The method, wherein the at least one emitter is configured to emit light energy at wavelengths of between about 300 nanometers to about 350 nanometers, at pulse durations between about 100 nanoseconds to about 150 nanoseconds, and at frequencies between about 1 pulse to about 250 pulses per second.

The method, wherein the light absorbing material is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 1000 pulses per second.

The method, wherein the light absorbing material is applied as a coating to a support structure located within the balloon catheter.

The present disclosure provides a catheter comprising of a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium, and a pressure-wave reflective element disposed adjacent to the balloon, wherein the pressure-wave reflective element attenuates the vapor bubble generated within the balloon catheter by the reaction between laser light emitted by the emitter and a liquid medium introduced into the balloon via the one or more liquid medium ports.

The catheter, wherein the pressure-wave reflective element is integrally disposed within the balloon catheter.

The catheter, wherein the balloon catheter has an exterior, and wherein the pressure-wave reflective element is disposed on the exterior of the balloon catheter.

The catheter, wherein the balloon catheter has an interior, and wherein the pressure-wave reflective element is disposed on the interior of the balloon catheter.

The catheter, wherein the pressure-wave reflective element comprises a plurality of openings.

The catheter, wherein the plurality of openings are between 10 microns and 10 millimeters.

The catheter, wherein a percentage of the openings within an area of a portion of the pressure-wave reflective element is between 10 percent and 90 percent.

The catheter, wherein an area of the pressure-wave reflective element comprises the openings and a structural mass, wherein a ratio of the openings to the structural mass within the area is between 10:1 and 1:10.

The catheter, wherein the plurality of openings comprise at least one of the following shapes: circle; oval; triangle; square; rectangle; polygon; diamond; pentagon; hexagon; heptagon; octagon; nonagon; and decagon.

The catheter, wherein at least one emitter is configured to emit laser light energy at wavelengths of between about 300 nanometers to about 350 nanometers, at pulse durations between about 100 nanoseconds to about 150 nanoseconds, and at frequencies between about 1 pulse per second to about 250 pulses per second.

The catheter, wherein at least one emitter is configured to emit laser light energy at wavelengths of about 308 nanometers, at pulse durations between about 120 nanoseconds and about 140 nanoseconds, and at frequencies between about 25 pulses per second to about 80 pulses per second.

The catheter, wherein total energy output for the at least one emitter is between about 30 to about 80 millijoules per millimeter squared (mJ/mm$^2$).

A catheter, wherein the total energy output for the at least one emitter is between about 20 to about 1000 millijoules per millimeter squared (mJ/mm$^2$).

The catheter, wherein the liquid medium is contrast medium or contrast solution.

The catheter, wherein the liquid medium is any one of iodine-containing contrast medium or gadolinium contrast medium.

The catheter, wherein the liquid medium is configured to exhibit high absorption of light energy emitted from the at least one emitter at wavelengths of between about 1 nanometer to about 1 millimeter, at pulse durations between about 1 nanosecond to about 1 second, and at frequencies between about 1 pulse per second to about 1000 pulses per second.

The present disclosure also provides a method for treating an obstruction or restriction within vasculature of a subject, the method comprising positioning a catheter within vasculature of a subject, a catheter comprising of a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a liquid medium, and a pressure-wave reflective element disposed adjacent to the balloon, wherein the pressure-wave reflective element attenuates the vapor bubble generated within the balloon catheter by the reaction between laser light emitted by the emitter and a liquid medium introduced into the balloon via the one or more liquid medium ports, positioning the balloon catheter adjacent to an obstruction or restriction within the vasculature, inflating the balloon catheter by delivering a liquid medium through the inflation lumen and out one or more liquid medium ports into the balloon catheter until a desired inflation pressure is obtained, and activating the at least one energy source to emit at least one pulse of light energy from the emitter within the balloon, whereupon the light energy reacts with the liquid medium and generates one or more laser-induced pressure waves that propagate through the balloon and disrupt at least a portion of the vascular obstruction or restriction, wherein the pressure-wave reflective element attenuates the vapor bubble.

The catheter, wherein the pressure-wave reflective element is integrally disposed within the balloon catheter.

The catheter, wherein the balloon catheter has an exterior, and wherein the pressure-wave reflective element is disposed on the exterior of the balloon catheter.

The catheter, wherein the balloon catheter has an interior, and wherein the pressure-wave reflective element is disposed on the interior of the balloon catheter.

The catheter, wherein the pressure-wave reflective element comprises a plurality of openings.

The method, wherein the plurality of openings are between 10 microns and 10 millimeters.

The method, wherein a percentage of the openings within an area of a portion of the pressure-wave reflective element is between 10 percent and 90 percent.

The method, wherein an area of the pressure-wave reflective element comprises the openings and a structural mass, wherein a ratio of the openings to the structural mass within the area is between 10:1 and 1:10.

The method, wherein the plurality of openings comprise at least one of the following shapes: circle; oval; triangle; square; rectangle; polygon; diamond; pentagon; hexagon; heptagon; octagon; nonagon; and decagon.

The method further comprising the step of re-positioning the balloon catheter such that the balloon is adjacent another portion of the obstruction or restriction.

The method further comprising the step of moving the at least one emitter within the balloon catheter.

The method, wherein the at least one emitter is moving within the pressure-wave reflective element.

The method further comprising the step of re-positioning the at least one emitter within the balloon catheter.

The method further comprising the step of re-positioning the at least one emitter within the pressure-wave reflective element.

The method further comprising the steps of removing the catheter from the vasculature.

The method further comprising the step of inserting a drug-coated balloon into the vasculature such that the drug-coated balloon is disposed adjacent a remaining portion of the occlusion.

The method further comprising the step of inflating the drug-coated balloon and applying a drug disposed on the drug-coated balloon to the remaining portion of the occlusion.

The present disclosure also provides a catheter system comprising a balloon catheter, comprising a catheter having a proximal end and a distal end and a lumen therein, and a balloon coupled to the catheter, wherein one or more liquid medium ports disposed about the catheter and within the balloon, wherein said liquid medium ports are used to fill the balloon with a liquid medium, a laser catheter comprising a proximal portion, distal portion, at least one or more emitters disposed therein, wherein the at least one or more emitters extend from the proximal portion, wherein the proximal portion is coupled to an energy source, wherein the at least one emitter is disposed within the balloon, a means for introducing a liquid medium into the balloon, a handle comprising a base coupled to the proximal end of the catheter, and a drive mechanism translatably coupled to the base, the drive mechanism coupled to the laser catheter such that translation of the drive mechanism relative to the base causes translation of the laser catheter within the lumen of the catheter and within the balloon.

The catheter system, wherein the drive mechanism comprises a control element movably coupled to the base; and a coupling translatably coupled to the base and driven by the control element, the coupling coupled to the laser catheter such that movement of the control element relative to the base causes translation of the laser catheter within the lumen of the catheter and within the balloon.

The catheter system, wherein the control element is rotatably coupled to the base, and rotation of the control element relative to the base causes translation of the laser catheter within the lumen of the catheter and within the balloon.

The catheter system, wherein the control element includes a first threaded surface, and the drive mechanism further includes a shaft that is translatable within the base and coupled to the coupling, the shaft including a second threaded surface, and the second threaded surface coupling to the first threaded surface such that rotation of the control element relative to the base causes translation of the shaft within the base and translation of the laser catheter within the lumen of the catheter and within the balloon.

The catheter system, wherein the handle further comprises a tube coupled to the base, the tube receiving the laser catheter, and wherein the shaft includes an inner lumen that translatably receives the tube as the shaft translates within the base.

The catheter system, wherein the drive mechanism further comprises a seal coupled to the shaft, the seal translatably engaging the tube.

The catheter system, wherein the tube is a hypotube.

The catheter system, wherein the base includes a first key feature, the shaft includes a second key feature that couples to the first key feature to inhibit rotation of the shaft relative to the base.

The catheter system, wherein the base includes an opening disposed within the control element, the second threaded surface extending through the opening to couple to the first threaded surface.

The present disclosure also provides for a handle for coupling to a catheter and a laser catheter, the handle comprising a base configured to couple to a proximal end of the catheter, and a drive mechanism translatably coupled to the base, the drive mechanism configured to couple to the laser catheter such that translation of the drive mechanism relative to the base causes translation of the laser catheter within a lumen of the catheter and within a balloon coupled to the catheter.

The handle, wherein the drive mechanism comprises a control element movably coupled to the base, and a coupling translatably coupled to the base and driven by the control element, the coupling being configured to couple to the laser catheter such that movement of the control element relative to the base causes translation of the laser catheter within the lumen of the catheter and within the balloon.

The handle, wherein the control element is rotatably coupled to the base, and rotation of the control element relative to the base causes translation of the laser catheter within the lumen of the catheter and within the balloon.

The handle, wherein the control element includes a first threaded surface, and the drive mechanism further includes a shaft that is translatable within the base and coupled to the coupling, the shaft including a second threaded surface, and the second threaded surface coupling to the first threaded surface such that rotation of the control element relative to the base causes translation of the shaft within the base and translation of the laser catheter within the lumen of the catheter and within the balloon.

The handle, wherein the handle further comprises a tube coupled to the base, the tube receiving the laser catheter, and wherein the shaft includes an passageway that translatably receives the tube as the shaft translates within the base and within the balloon.

The handle, wherein the drive mechanism further comprises a seal coupled to the shaft, the seal translatably engaging the tube.

The handle, wherein the tube is a hypotube.

The handle, wherein the base includes a first key feature, the shaft includes a second key feature that couples to the first key feature to inhibit rotation of the shaft relative to the base.

The handle, wherein the base includes an opening disposed within the control element, the second threaded surface extending through the opening to couple to the first threaded surface.

The present disclosure also provides a catheter system comprising a balloon catheter having a proximal end and a distal end and a lumen therein, and a balloon coupled to the catheter, wherein one or more liquid medium ports disposed about the catheter and within the balloon, wherein said liquid medium ports are used to fill the balloon with a liquid medium, a laser catheter comprising a proximal portion, distal portion, at least one or more emitters disposed therein, wherein the at least one or more emitters extend from the proximal portion, wherein the proximal portion is coupled to an energy source, wherein the at least one emitter is disposed within the balloon, a means for introducing a liquid medium into the balloon, a handle comprising a base coupled to the proximal end of the catheter, and a drive mechanism translatably coupled to the base, the drive mechanism coupled to the laser catheter such that translation of the drive mechanism relative to the base causes translation of the laser catheter within the lumen of the catheter and within the balloon, positioning the balloon adjacent to an obstruction or restriction within the vasculature, inflating the balloon by delivering a liquid medium through an inner lumen of the catheter and out one or more liquid medium ports into the balloon until a desired inflation pressure is obtained, and activating the at least one energy source to emit one or more pulses of light energy from the at least one emitter within the balloon, wherein emitting the one or more pulses of light energy from the at least one emitter reacts with the liquid medium and generates a plurality of propagating laser-induced pressure waves that engage and disrupt at least a portion of the vascular obstruction or restriction, and actuating the handle and sliding the at least one emitter within the balloon.

The method further incorporating the structure or steps.

The present disclosure provides a method for treating an obstruction or restriction within the vasculature of a subject, the method comprising positioning a catheter within the vasculature of a subject, the catheter comprising a lumen, a proximal end and a distal end, one or more emitters circumferentially arranged around or adjacent to the lumen, a balloon circumferentially arranged around a portion of the catheter, at least one energy source coupled to the at least one emitter, wherein said emitter is coupled to the catheter and disposed within the balloon, wherein said emitter is disposed proximate to the distal end of the catheter, wherein one or more liquid medium ports disposed about the catheter and within the balloon, wherein said liquid medium ports are used to fill the balloon with a gas-saturated liquid medium positioning the balloon adjacent to an obstruction or restriction within the vasculature, inflating the balloon by delivering a gas-saturated liquid medium through an inner lumen of the catheter and out one or more liquid medium ports into the balloon until a desired inflation pressure is obtained, and activating the at least one energy source to emit one or more pulses of light energy from the at least one emitter within the balloon, wherein emitting the one or more pulses of light energy from the at least one emitter reacts with the gas-saturated liquid medium and generates a plurality of propagating laser-induced pressure waves that engage and disrupt at least a portion of the vascular obstruction or restriction.

The method wherein the at least one emitter is configured to emit light energy at wavelengths of between about 300 nanometers to about 350 nanometers, at pulse durations between about 100 nanoseconds to about 150 nanoseconds, and at frequencies between about 1 pulse per second to about 250 pulses per second.

The method, wherein the gas-saturated liquid medium is any one of iodine-containing contrast medium or gadolinium contrast medium.

The method, wherein the gas-saturated liquid medium comprises a super saturated liquid medium.

The method, wherein the inflation pressure obtained by delivering liquid medium into the dilation balloon catheter is greater than 0.0 atmospheres and up to about 20.0 atmospheres of pressure.

The present disclosure provides a method for improving the compliance of a blood vessel within a subject, the method comprising locating a calcified portion in the media and/or the intima of the blood vessel of the subject, positioning a catheter within the blood vessel, the catheter comprising a tube having a lumen, a proximal end and a distal end, one or more emitters arranged around or adjacent to the lumen, wherein the emitters have respective distal ends disposed adjacent the distal end of the tube, a balloon circumferentially arranged around a portion of the distal end of the tube, and one or more liquid medium ports disposed about the catheter and within the balloon, positioning the balloon adjacent the calcified portion in the media and/or the intima, inflating the balloon by delivering a liquid medium through an inner lumen of the tube and out one or more liquid medium ports into the balloon until a desired inflation pressure is obtained, and emitting one or more pulses of light energy from the distal end of the emitters, wherein the one or more pulses of light energy reacts with the liquid medium and generates a plurality of propagating laser-induced pressure waves that disrupt the calcified portion of media and/or intima, thereby improving the compliance of the blood vessel.

The method, wherein the at one or more pulses of light energy comprises a wavelength of between about 300 nanometers to about 350 nanometers, at pulse durations between about 100 nanoseconds to about 150 nanoseconds, and at frequencies between about 1 pulse per second to about 250 pulses per second.

The method, wherein the liquid medium is any one of iodine-containing contrast medium or gadolinium contrast medium.

The method, wherein the inflation pressure obtained by delivering liquid medium into the dilation balloon is between about 0.25 atmospheres and about 5.0 atmospheres of pressure.

The method, wherein the plurality of propagating laser-induced pressure waves enhances penetration of one or more therapeutic agents into the media and/or the intima.

The method, wherein the one or more therapeutic agents comprises one or more oxidation-insensitive drugs in a polymer-free drug preparation.

The method, wherein the one or more oxidation-insensitive drugs is one or more of taxanes, thalidomide, statins, corticoids, and lipophilic derivatives of corticoids.

The method, wherein the one or more pulses of light energy comprises a wavelength a of about 308 nanometers, at pulse durations between about 120 nanoseconds and about 140 nanoseconds, and at frequencies between about 25 pulses per second to about 80 pulses per second.

The method, wherein total energy output for the one or more pulses of light energy comprises energy between about 30 to about 80 millijoules per millimeter squared (mJ/mm2).

The present disclosure provides a method for disrupting a calcified portion contained within the media and/or the intima of a blood vessel wall of a subject, the method comprising positioning a catheter within the blood vessel of the subject, the catheter comprising a tube having a guidewire lumen, an inflation lumen, a proximal end and a distal end, a plurality of emitters circumferentially arranged around or adjacent to the guidewire lumen, wherein at least a portion of the plurality of emitters comprises a distal end, a balloon circumferentially arranged around a portion of the tube and around at least a portion of the distal end of the emitters, one or more liquid medium ports disposed within the tube and within the balloon; and a pressure-wave reflective element disposed adjacent the balloon, positioning the balloon adjacent the calcified portion in the media and/or the intima of the blood vessel, inflating the balloon by delivering a liquid medium through the inflation lumen and out one or more liquid medium ports into the balloon until a desired inflation pressure is obtained, and emitting at least one pulse of light energy from the distal end of the emitters, whereupon the light energy reacts with the liquid medium and generates one or more laser-induced pressure waves that propagate through the balloon and disrupt the calcified portion in the media and/or the intima, wherein the pressure-wave reflective element reduces formation of vapor bubbles arising from the laser-induced pressure wave.

The method, wherein the pressure-wave reflective element comprises a plurality of openings.

The method, wherein the plurality of openings are between 10 microns and 10 millimeters.

The method, wherein a percentage of the openings within an area of a portion of the pressure-wave reflective element is between 10 percent and 90 percent.

The method, wherein an area of the pressure-wave reflective element comprises the openings and a structural mass, wherein a ratio of the openings to the structural mass within the area is between 10:1 and 1:10.

The method, wherein the plurality of openings comprise at least one of the following shapes: circle; oval; triangle; square; rectangle; polygon; diamond; pentagon; hexagon; heptagon; octagon; nonagon; and decagon.

The method further comprising the step of re-positioning the balloon such that the balloon is adjacent another portion of the obstruction or restriction.

The method, further comprising the step of moving the plurality of emitters within the balloon.

The method, wherein the within the plurality of emitters is re-positioned within the pressure-wave reflective element.

The method, further comprising the step of re-positioning the plurality of emitters within the balloon.

The method, wherein the within the plurality of emitters is re-positioned within the pressure-wave reflective element.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "catheter" as used herein generally refers to a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

The term "balloon catheter" as used herein generally refers to the various types of catheters which carry a balloon for containing fluids. Balloon catheters may also be of a wide variety of inner structure, such as different lumen design, of which there are at least three basic types: triple lumen, dual lumen and co-axial lumen. All varieties of internal structure and design variation are meant to be included by use of the term "balloon catheter" herein.

The terms "emitter" as used herein refers to a fiber or an optical component (including any portion thereof, such as the end of a fiber) that emits light from a distal end of device, such as a catheter, towards a desired target. An emitter can be the output end of any device that transports light from an optical energy source to a target or treatment area. These optical energy transport devices can include glass or fused silica fiber optics, plastic fiber optics, air or gas light guides, and liquid light guides. As described herein, an emitter or emitters can be used to emit light of any wavelength. An emitter or emitters can emit light, including but not limited to, laser light, white light, visible light, infrared light, and ultraviolet light According to the present disclosure, the catheter contains at least one emitter, which may comprise glass or fused silica fiber optics, plastic fiber optics, air or gas light guides, and liquid light guides. Examples of a liquid light guide, or a catheter that contain a liquid light guide can be seen in U.S. application Ser. No. 11/923,488, filed Oct. 24, 2007 and U.S. application Ser. No. 12/254,254, filed Oct. 20, 2008, both of which are hereby incorporated herein by reference in their entireties for all that they teach and for all purposes.

The term "laser-induced pressure wave" as used herein is a pressure wave caused by a reaction between laser light and an absorptive material. The laser-induced pressure wave may be generated in a gas, liquid, or solid.

The term "pressure-wave reflective element" as used herein is any component which redirects a laser-induced pressure wave.

The term "vapor bubble" as used herein is a gaseous cavity created within a liquid.

The term "cavitation event" as used herein describes the rapid fluid movement that leads to collapse of a vapor bubble to its smallest radius.

The term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

The term "therapeutic agent" as used herein generally refers to any known or hereafter discovered pharmacologically active agent that provides therapy to a subject through the alleviation of one or more of the subject's physiological symptoms. A therapeutic agent may be a compound that occurs in nature, a chemically modified naturally occurring compound, or a compound that is chemically synthesized. The agent will typically be chosen from the generally recognized classes of pharmacologically active agents, including, but not necessarily limited to, the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; restenosis inhibitors; muscle relaxants; narcotic antagonists; nicotine; nutritional agents, such as vitamins, essential amino acids and fatty acids; ophthalmic drugs such as antiglaucoma agents; parasympatholytics; psychostimulants; sedatives; steroids; sympathomimetics; tranquilizers; and vasodilators including general coronary, peripheral and cerebral.

The terms "vasculature" and "vascular" as used herein refer to any part of the circulatory system of a subject, including peripheral and non-peripheral arteries and veins. Vasculature can be comprised of materials such as nucleic acids, amino acids, carbohydrates, polysaccharides, lipids fibrous tissue, calcium deposits, remnants of dead cells, cellular debris and the like.

The term "vascular occlusion" refers to buildup of fats, lipids, fibrin, fibro-calcific plaque, thrombus and other atherosclerotic tissue within the lumen or within the intima of an artery that either narrows or completely obstructs the inner lumen the artery thereby restricting or blocking normal blood flow through the artery segment.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 1 is a representative longitudinal view of the distal end of a catheter with the balloon catheter partially inflated, according to one embodiment of the present disclosure.

FIG. 1A is a representative cross-sectional view (through plane A in FIG. 1) of the distal end of a catheter with the balloon catheter in a partially inflated configuration, according to one embodiment of the present disclosure.

FIG. 1B is a representative cross-sectional view (through plane B in FIG. 1) of the distal end of a catheter with the balloon catheter in a partially inflated configuration, according to one embodiment of the present disclosure.

FIG. 1C is a representative cross-sectional view (through plane C in FIG. 1) of the distal tip of the catheter, according to one embodiment of the present disclosure.

FIG. 6N is a representative cross-sectional view of the distal end of the catheter illustrated in FIG. 6 through plan A-A, according to an alternate embodiment of the present disclosure.

FIG. 10 is a representative perspective view of the distal end of a balloon catheter with a laser ablation catheter slidable within the balloon and balloon catheter, according to one embodiment of the present disclosure.

FIG. 10A is a representative cross-sectional side view of the distal end of the balloon catheter and laser ablation catheter illustrated in FIG. 10.

FIG. 17A is a perspective view of the handle of FIG. 16A, wherein several external components are partially transparent to illustrate internal components, and a shaft of the handle is shown in a proximal position.

FIG. 17B is another perspective view of the handle of FIG. 16A, wherein several external components are partially transparent to illustrate internal components, and the shaft is shown in the proximal position.

FIG. 17C is an elevation view of the handle of FIG. 16A, wherein several external components are partially transparent to illustrate internal components, and the shaft is shown in the proximal position.

FIG. 17D is an elevation view of the handle of FIG. 16A, wherein several external components are partially transparent to illustrate internal components, and the shaft is shown in an intermediate position.

FIG. 20A is reduced version of the cross-sectional view of the arterial wall in FIG. 20.

FIG. 21A is a longitudinal-sectional view of a healthy arterial wall taken along a direction parallel to the longitudinal axis of the arterial wall.

FIG. 21B is a longitudinal-sectional view of an arterial wall taken along a direction parallel to the longitudinal axis of the arterial wall, wherein the arterial wall includes fat and/or lipids.

FIG. 21C is a longitudinal-sectional view of an arterial wall taken along a direction parallel to the longitudinal axis of the arterial wall, wherein the arterial wall includes plaque and calcium in the intima.

FIG. 21D is a longitudinal-sectional view of an arterial wall taken along a direction parallel to the longitudinal axis of the arterial wall, wherein the arterial wall includes calcified plaque and lipids in the intima FIG. 21E is a longitudinal-sectional view of an arterial wall taken along a direction parallel to the longitudinal axis of the arterial wall, wherein the arterial wall has ruptured.

FIG. 21F is a longitudinal-sectional view of an arterial wall taken along a direction parallel to the longitudinal axis of the arterial wall, wherein the artery includes an obstruction or restriction.

FIG. 21G is a longitudinal-sectional view of an arterial wall taken along a direction parallel to the longitudinal axis of the arterial wall with a laser catheter removing the obstruction or restriction depicted in FIG. 21F.

FIG. 21H is a longitudinal-sectional view of an arterial wall taken along a direction parallel to the longitudinal axis of the arterial wall with a laser-induced balloon catheter located adjacent the remaining portion of the obstruction or restriction depicted in FIG. 21G.

FIG. 21I is a longitudinal-sectional view of an arterial wall taken along a direction parallel to the longitudinal axis of the arterial wall after utilizing the laser-induced balloon catheter illustrated in FIG. 21H.

DETAILED DESCRIPTION

Figure 2:
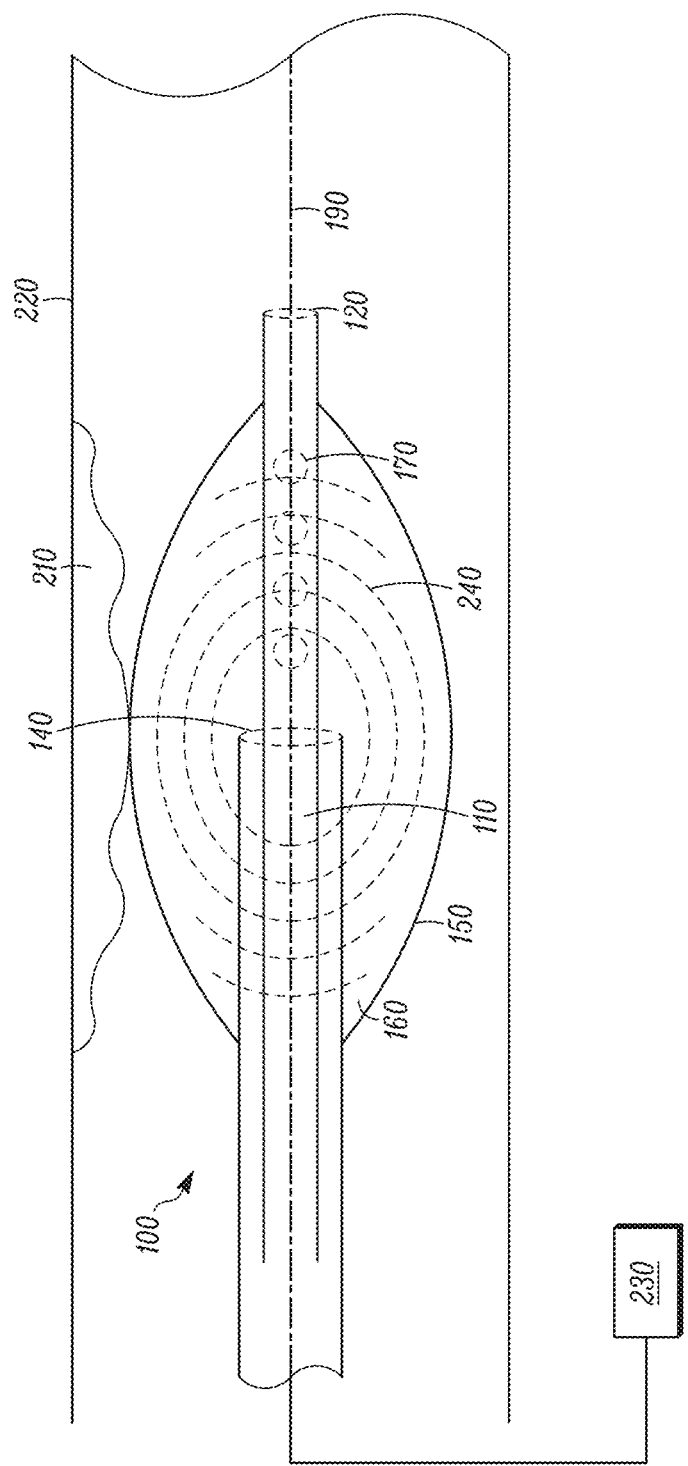
FIG. 2 is a representative longitudinal view of the distal end of a catheter adjacent to a vascular obstruction or restriction within a vessel of a subject, according to one embodiment of the present disclosure.

The present disclosure relates generally to the use of medical devices for the treatment of vascular conditions. In particular, the present disclosure provides materials and methods for using laser-induced pressure waves to disrupt vascular blockages and to deliver therapeutic agents to the blockage area.

Referring to FIG. 1, the distal end of catheter 100 of the present disclosure includes one or more layers of optical fibers arranged circumferentially around or adjacent to an inner lumen 110. The proximal end of the catheter 100 is coupled to a laser generator, which is not shown. The one or more layers of optical fibers are housed in a flexible tubular catheter and terminate at different points of emission (such as, emitters), where the laser light energy is released and directed towards a desired target. The inner layer of optical fibers 115 terminates at the distal emitter 120 at the distal tip 130 of the catheter, while the outer layer of optical fibers 135 terminates at the proximal emitter 140 of the catheter. The proximal laser emitter 140 is disposed proximate of the distal tip and contained within the balloon 150, which is circumferentially arranged around a portion of the distal end of the catheter excluding the distal tip 130 of the catheter and the distal emitter 140. Although the proximal laser emitter 140 is at the distal end of the catheter 100, it may be located at the central portion of the catheter. The inner lumen 110 provides a conduit for the delivery of a liquid medium 160 that is used to inflate the balloon to a desired pressure. The liquid medium 160 travels through the inner lumen 110 until being released from one or more liquid medium ports 170 enclosed within the balloon 150. In the inflated or partially inflated configuration, as shown in FIG. 1, the proximal laser emitter 140 is in direct contact with the liquid medium 160 such that when laser light energy is emitted from the proximal emitter 140, the liquid medium 160 absorbs the emitted light.

Upon emitting the light into the liquid medium and the liquid medium absorbing the light, a laser-induced pressure wave is created in the liquid medium. The pressure wave compresses the fluid surrounding its origin, thereby generating a vapor bubble. As the pressure wave propagates away from its origin, the fluid surrounding the vapor bubble displaces inward, collapsing the vapor bubble and creating a cavitation event. The vapor bubble and subsequent cavitation event are byproducts of the laser-induced pressure wave. The laser-induced pressure wave penetrates and/or passes through the balloon catheter 140, and the fluid movement associated with the formation and collapse of the vapor bubble expands and then reduces the diameter of the balloon of the balloon catheter.

FIG. 1A is a representative cross-sectional view of the distal end of the catheter 100 of the present disclosure taken along the plane demarcated by line A-A in FIG. 1. As shown, the distal end of the catheter 100 includes one or more layers of optical fibers 115 arranged circumferentially around an inner lumen 110. The inner layer of optical fibers 115 extends to the distal tip 130 of the catheter and terminates at the distal emitter 120, while the outer layer of optical fibers 135 terminates at the proximal emitter 140 within the balloon 150. In the inflated or partially inflated configuration shown in FIGS. 1-1B, the balloon 150 is inflated with liquid medium 160. As shown in FIG. 1B, a cross-sectional view along the plane demarcated by line B-B in FIG. 1, the liquid medium 160 is delivered into the balloon 150 via one or more liquid medium ports 170 (see arrow in FIG. 1B). The liquid medium ports 170 may also serve as a means for removing the liquid medium to modulate the pressure within the balloon (for example, different pressures required by different procedures) and to deflate the balloon 150.

The ability of liquid medium 160 to absorb light energy can degrade after prolonged exposure to the light energy.

Liquid medium 160 can be removed from the balloon 150 through a separate set of liquid medium ports that act as liquid medium exit ports. Liquid medium exit ports can, for example, be configured to allow for the slow purgation or exchange of liquid medium 160 through an inner lumen in the catheter, while not significantly altering the overall pressure within the balloon catheter itself.

In some embodiments, the catheter of the present disclosure includes one or more additional lumens located near the inner lumen 110. For example, as shown in FIG. 1C, a cross-sectional view along the plane demarcated by line C-C in FIG. 1, the catheter of the present disclosure can include a guidewire lumen 180 to allow a guidewire 190 to be inserted therethrough, thereby facilitating the positioning of the distal end of the catheter within the vessel of the subject, as well as lumens for the insertion of cameras, and cutting or ablation devices. Generally, the number of rows of optical fibers, emitters, and lumens located in the catheter assembly and/or located concentrically around or adjacent to the lumen and the number of optical fibers, emitters, and lumens in each row can vary by application and are not limited to the depicted configurations.

FIG. 2 is a representative longitudinal view of the distal end of laser balloon catheter 100 adjacent to a vascular obstruction or restriction 210 within a vessel of a subject 220. The catheter 10 has been placed at the desired location by sliding the catheter 100 over a guidewire 190 through the guidewire lumen 180. To treat a subject having a vascular obstruction or restriction 210, the distal end of the laser balloon catheter 100 is positioned adjacent to the vascular obstruction or restriction 210. The balloon 150 is inflated to a desired pressure with a liquid medium 160 delivered from an inner lumen 110 through one or more liquid medium ports 170 within the balloon 150. When the laser system is activated, light energy travels through one or more layers of optical fibers until the light energy is released from the proximal laser emitter 140.

Figure 9:
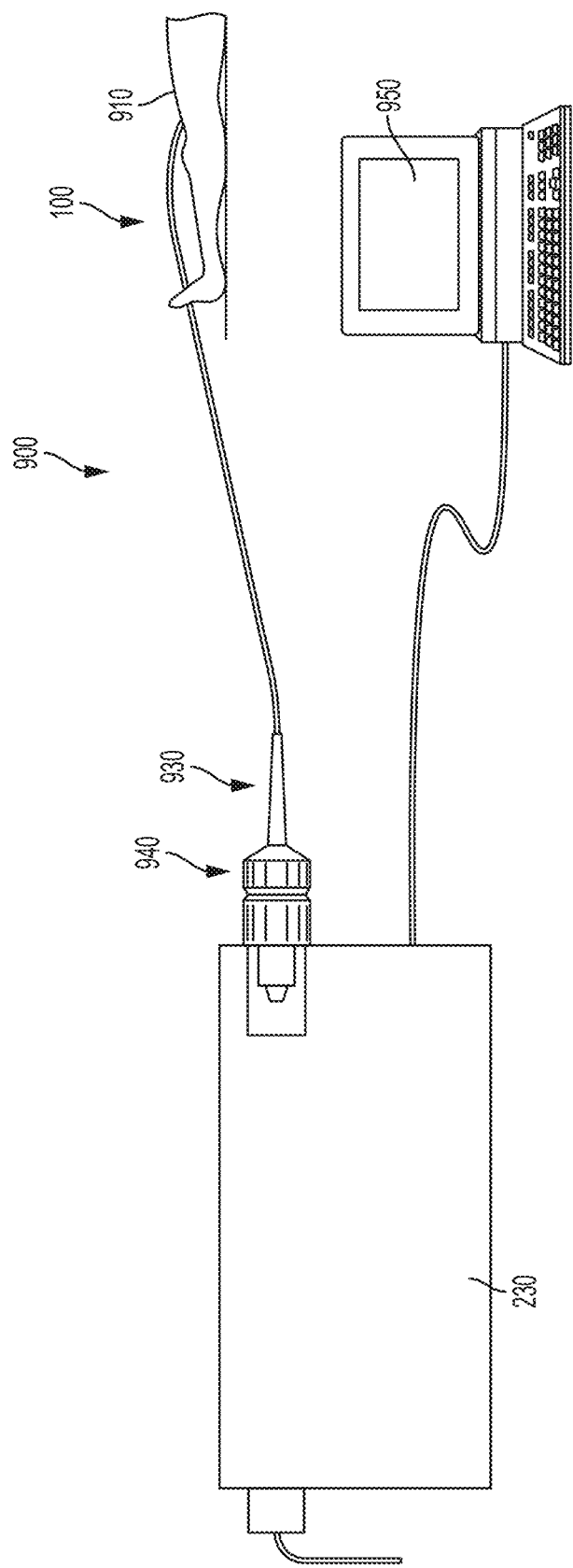
FIG. 9 illustrates an exemplary ablation system, including a laser generator and a laser-induced pressure wave emitting balloon catheter.

For example, referring to FIG. 9, there is depicted an exemplary laser system 900 of the present disclosure. Laser system 900 includes a laser balloon catheter 100 coupled to a laser controller 950. Controller 950 includes one or more computing devices programmed to control laser 230. Controller 950 may be internal or external to laser apparatus 920, such as a laser generator. The laser apparatus 230 may include an excimer laser or another suitable laser. In some embodiments, the laser 230 produces light in the ultraviolet frequency range. In one embodiment, the laser 230 produces optical energy in pulses.

Laser 230 is connected with the proximal end of a laser energy delivery system, illustratively a laser catheter 100 via coupler 140. Laser catheter 170 includes one or more transport members which receive laser energy from laser 940 and transports the received laser energy from a first, proximal end of laser energy catheter 100 towards a second, distal end of laser catheter 100. The distal end of catheter 100 may be inserted into a vessel or tissue of a human body 910. In some embodiments, system 900 employs a plurality of light guides as the transport members, such as optical fibers, that guide laser light from laser 230 through catheter 100 toward a target area in human body 910.

Exemplary laser catheter devices or assemblies may include laser catheters and/or laser catheters. Examples of laser catheters or laser catheter are sold by The Spectranetics Corporation under the tradenames ELCA™ and Turbo Elite™ (each of which is used for coronary intervention or peripheral intervention, respectively, such as recanalizing occluded arteries, changing lesion morphology, and facilitating stent placement) and SLSII™ and GlideLight™ (which is used for surgically implanted lead removal). The working (distal) end of a laser catheter typically has a plurality of laser emitters that emit energy and ablate the targeted tissue. The opposite (proximal) end of a laser catheter typically has a fiber optic coupler 940 and an optional strain-relief member 930. The fiber optic coupler 940 connects to a laser system or generator 930. One such example of a laser system is the CVX-300 Excimer Laser System, which is also sold by the Spectranetics Corporation.

The laser controller 950 of FIG. 9 includes a non-transitory computer-readable medium (for example, memory) that includes instructions that, when executed, cause one or more processors to control laser 930 and/or other components of ablation system 900. Controller 950 includes one or more input devices to receive input from an operator. Exemplary input devices include keys, buttons, touch screens, dials, switches, mouse, and trackballs which providing user control of laser 930. Controller 950 further includes one or more output devices to provide feedback or information to an operator. Exemplary output devices include a display, lights, audio devices which provide user feedback or information.

FIG. 9 depicts the catheter 100 entering the leg, preferably through the femoral artery, of the human body. As discussed above, it may be desirable to treat either CAD or PAD. After entering the femoral artery, it the catheter 100 is intended to treat CAD, the catheter 170 will be directed through the patient's vasculature system and to the coronary arteries. Alternatively, if the catheter 100 is intended to treat PAD, the catheter 100 will be directed through the patient's vasculature system and to the peripheral arteries, such as the vasculature below the knee, particularly the vasculature in the patient's legs and/or feet.

As discussed above, upon emitting the light into the liquid medium and the liquid medium absorbing the light, a pressure wave is created in the liquid medium, which in turn generates a vapor bubble and a cavitation event. The pressure waves penetrate and/or pass through the balloon catheter 140, and the fluid movement associated with the formation and collapse of the vapor bubble expands and then reduces the diameter of the balloon catheter. Referring again to FIG. 2, as the liquid medium 160 absorbs the light energy, the pressure waves 240 (dotted lines) propagate through the liquid medium 160 and through the balloon 150. Upon passing through the balloon 150, the resultant energy of the pressure waves 240 transferred to the vascular obstruction or restriction 210 and/or to the walls of the vessel 220. The transfer of the energy produced by the pressure waves 240 to the vascular obstruction or restriction 210 and/or to the walls of the vessel 220 is sufficient to disrupt intraluminal as well as medial (within the tissue layer of the vascular wall) vascular obstructions or restrictions (for example, calcium deposits). The forces generated by the pressure waves 240 can propagate radially, including in forward (such as, parallel to the vessel), upward (such as, perpendicular to the vessel), and backward (such as, proximally) directions. Laser-induced pressure waves produced in this manner can also be used to increase vessel compliance prior to performing another procedure, such as a traditional balloon angioplasty.

Laser-induced pressure waves generally have different characteristics in comparison to ultrasound. Ultrasound typically consists of periodic oscillations with limited bandwidth. Laser-induced pressure waves are single, mainly positive pressure pulses that are followed by comparatively small tensile wave components. Ultrasound applies an alternating high frequency load to tissue, with a frequency range of several megahertz, and can thus lead to heating, tissue tears and cavitation at high amplitudes. The effect of laser-induced pressure waves in comparison, however, largely involves radially directed energy, as described above, enabling the treatment of deep tissue as well as adjacent tissue with enhanced sensitivity.

Again, upon emitting the light into the liquid medium and the liquid medium absorbing the light, a pressure wave in the liquid medium is not only produced, but a vapor bubble is also created. The vapor bubbles created within the balloon 150 of the balloon catheter or on the exterior of the balloon cause the balloon 150 to expand and contract. The fluid movement associated with the formation and collapse of the vapor bubble expands and then reduces the diameter of the balloon 150 creating a hydraulic force that is also transferred to the vascular obstruction or restriction 210 and/or to the walls of the vessel 220 is sufficient to disrupt intraluminal as well as medial (within the tissue layer of the vascular wall) vascular obstruction or restrictions (for example, calcium deposits).

Additionally or alternatively, the catheter of the present disclosure can also be used to deliver one or more therapeutic agents to the vascular obstruction or restriction 210 and/or to the vascular tissues of the vessel 220. The outwardly propagating pressure waves 240 generated by the absorption of the light energy by the liquid medium 160 and/or the rapid expansion and contraction of the balloon 150 can deliver one or more therapeutic agents that have been coated, for example, on the outside of the balloon 150. When the balloon 150 is brought in contact with the desired target (for example, a vascular obstruction or restriction 210 and/or the vascular tissues of the vessel 220), the propagation of the pressure waves 240 through the balloon 150 and/or the expansion and contraction of the balloon 150 causes the therapeutic agent to become detached from the balloon 150 and be delivered to or embedded in the desired target. Additionally, under suitable therapeutic parameters, the pressure waves 240 may create small spaces within the vascular obstruction or restriction 210 and/or within the vascular tissues of the vessel 220, which may enhance the penetration of the therapeutic agent into the vascular obstruction or restriction 210 or the vascular tissue of the vessel 220. Energy from the pressure waves 240 may also increase the kinetic energy of the molecules making up the therapeutic agents, which may further enhance the delivery and penetration of the therapeutic agent into the target tissue.

The therapeutic agents of the present disclosure can be chosen based upon functional characteristics, including, but not necessarily limited to, the ability to inhibit restenosis, mitosis or cellular proliferation. For example, a therapeutic agent can be a taxane, including paclitaxel, docetaxel, protaxel, DHA-paclitaxel, PG-paclitaxel, docosahexaenoic acid (DHA), or any combinations or derivatives thereof capable of inhibiting mitosis or cellular proliferation. In some cases, the presence of a mitotic inhibitor prevents restenosis that may occur in the absence of the inhibitor. Other examples of therapeutic agents include rapamycin (for example, sirolimus) or a derivative of rapamycin (for example, everolimus), or any combinations or derivatives thereof. Additionally or alternatively, specific inhibitors of neovascularization such as thalidomide, statins such as atorvastatin, cerivastatin, fluvastatin, or anti-inflammatory drugs like corticoids or lipophilic derivatives of corticoids such as betamethasone dipropionate or dexa-methasone-21-palmitate are examples of oxidation-insensitive drugs that can be used with the laser ablation catheters of the present disclosure. Various therapeutic agents may be applied or combined if different pharmacological actions are required or efficacy or tolerance is to be improved.

The therapeutic agents can also be combined with various adjuvants and excipients to enhance efficacy or delivery of the therapeutic agents. For example, the therapeutic agents can be combined with lipophilic antioxidant such as nordihydroguaiaretic acid, resveratrol and propyl gallate to enhance the adhesion of the therapeutic to, for example, a balloon catheter. In some cases, the combination of a therapeutic agent such as paclitaxel and a lipophilic antioxidant such as nordihydroguaiaretic acid can be applied to a balloon catheter without the need for additional polymers (such as, polymer-free).

The ability of the catheter of the present disclosure to generate pressure waves 240 for treating a vascular obstruction or restriction 210 in a subject involves the suitable coupling of the light system 240 and the liquid medium 160. Any wavelength of light can be used, including but not limited to, laser light, visible light, ultraviolet light and infrared light, as long as the light being emitted is coupled with a liquid medium capable of absorbing the light and producing pressure waves. Additionally, any liquid medium can be used, as long as the liquid medium is coupled with a light source that emits light at a suitable wavelength such that the liquid absorbs the light and produces resultant pressure waves. In some cases, the liquid medium can be contrast medium (for example, iodine-containing contrast medium or gadolinium contrast medium) and/or the liquid medium can be a contrast solution comprising a biocompatible fluid (for example, saline) in which a contrast dye(s) or particle(s) have been mixed at various concentrations.

The force amplitude generated by the laser-induced pressure waves 240 depends in part on the degree of absorption of the light energy by the liquid medium 160. Generally, the greater the absorption of the light energy by the liquid medium 160, the greater the force generated by the pressure waves 240. For example, an excimer laser typically emits laser light at a wavelength of about 308 nanometers at pulse durations between about 120 nanoseconds and about 140 nanoseconds, at frequencies between about 25 pulses per second to about 80 pulses per second, and with a total energy output between about 30 to about 80 millijoules per millimeter squared (mJ/mm$^2$). In some cases, however, total energy output of a laser light system can range from greater than 0 to about 300 mJ/mm$^2$. When emitted within contrast medium, such as iodine-containing contrast medium or gadolinium contrast medium, there will be a very high degree of absorption by the contrast medium, thus creating pressure waves with sufficient force to treat a vascular obstruction or restriction in a subject.

Light energy can be emitted at any suitable wavelength capable of generating pressure waves. Light energy can be emitted between about 1 nanometer and about 1 millimeter. In some cases, light can be emitted from about 10 nanometers to about 5000 nanometers. In some cases, light can be emitted from about 100 nanometers to about 1000 nanometers. In some cases, light can be emitted from about 250 nanometers to about 750 nanometers. In some cases, light can be emitted from about 300 nanometers to about 600 nanometers. In still other cases, light can be emitted from about 300 nanometers to about 350 nanometers.

Light energy can be emitted at any suitable pulse duration capable of generating pressure waves. In some cases, light can be emitted at pulse durations between about 1 nanosecond to about 1 second. In some cases, light can be emitted at pulse durations between about 10 nanoseconds to about 500 nanoseconds. In some cases, light can be emitted at pulse durations between about 100 nanoseconds to about 150 nanoseconds. In still other cases, light can be emitted at pulse durations between about 120 nanoseconds and about 140 nanoseconds.

Light energy can be emitted at any suitable pulse repetition frequency (PRF), or pulses per second, capable of generating pressure waves that propagate through the balloon catheter and the surrounding vasculature. In some cases, light can be pulsed at a frequency of between about 1 pulse to about 500 pulses per second. In some cases, light can be pulsed at a frequency of between about 10 pulses to about 250 pulses per second. In some cases, light can be pulsed at a frequency of between about 10 pulses to about 150 pulses per second. In some cases, light can be pulsed at a frequency of between about 10 pulses to about 100 pulses per second. In other cases, light can be pulsed at a frequency of between about 50 pulses to about 150 pulses per second. In other cases, light can be pulsed at a frequency of between about 50 pulses to about 100 pulses per second. In still other cases, light can be pulsed at a frequency of between about 25 pulses to about 80 pulses per second.

The total number of pulses administered during a particular treatment period depends on a variety of factors, including patient characteristics, the type of condition being treated, and the specific characteristics of the vascular obstruction or restriction, as one of ordinary skill in the art would readily appreciate based on the present disclosure. In some cases, the total number of pulses administered during a treatment period can range from a single pulse to any number of pulses generated in a 10 second treatment period, a 15 second treatment period, a 20 second treatment period, a 25 second treatment period, a 30 second treatment period, up to a 1 minute treatment period. Treatment periods can be repeated depending on the extent of the vascular obstruction or restriction remaining after initial treatment.

The degree of force generated by the pressure waves 240 can be modulated by using lasers that produces laser light energy at different wavelengths and at different pulse durations, as would be appreciated by one of ordinary skill in the art based on the present disclosure. For example, different degrees of force may be required to break apart a vascular obstruction or restriction, as compared to the degree of force required to deliver a therapeutic agent to vascular tissue. In some embodiments, a laser having a holmium source, referred a Holmium laser, can emit laser light energy at a wavelength of about 2,100 nanometers (nm) and can be coupled with various light absorbing materials, including an aqueous or saline-based medium, to treat a vascular obstruction or restriction in a subject.

Several other additional sources of laser light energy can be paired with corresponding light absorbing materials to generate pressure waves to treat a vascular obstruction or restriction. For example, YAG crystal lasers can produce wavelengths of infrared light, which is highly absorptive in aqueous solutions. Aqueous solutions can be used as light absorbing material or medium to generate pressure waves. Aqueous solutions include, but are not limited to, saline, dextrose, radio-opaque contrast, lactated ringer's, and electrolyte solutions. In some cases, YAG wavelengths can be doubled to generate visible spectrum light of 532 nm wavelength. Materials or medium capable of absorbing light of this wavelength include, but are not limited to, gold nanospheres, nitrite solutions, potassium permanganate solutions, copper salts, aluminum solutions, aluminon, ammonia salts, and dyes such as hemotoxylin and propidium iodide. Light absorbing materials such as these can be part of a solution, such as an aqueous solution as described above, and/or they can be applied as coatings on various surfaces within a device.

In some embodiments, a Holmium YAG laser can emit laser light energy at a wavelength of about 2,120 nm and can be coupled with various light absorbing materials, including an aqueous or saline-based medium, to treat a vascular obstruction or restriction in a subject. In some embodiments, a thulium laser, such as a Thulium YAG laser, can emit laser light energy at a wavelength of about 2,013 nm and can be coupled with various light absorbing materials, including an aqueous or saline-based medium, to treat a vascular obstruction or restriction in a subject. In some embodiments, a thulium laser, such as a Thulium Fiber laser, can emit laser light energy at a wavelength of about 1,908 nm and can be coupled with various light absorbing materials, including an aqueous or saline-based medium, to treat a vascular obstruction or restriction in a subject. In some embodiments, an Nd-YAG laser can emit laser light energy at a wavelength of about 1,064 nm and can be coupled with various light absorbing materials to treat a vascular obstruction or restriction in a subject. In some embodiments, a doubled YAG laser can emit laser light energy at a wavelength of about 532 nm and can be coupled with various light absorbing materials to treat a vascular obstruction or restriction in a subject. In some embodiments, an alternative band YAG laser can emit laser light energy at a wavelength of about 1,319 nm and can be coupled with various light absorbing materials to treat a vascular obstruction or restriction in a subject. In still other embodiments, an Er-YAG laser can emit laser light energy at a wavelength of about 2,940 nm and can be coupled with various light absorbing materials to treat a vascular obstruction or restriction in a subject.

Carbon dioxide ($CO_2$) lasers can emit infrared light that is highly absorptive in aqueous solutions. $CO_2$ lasers are common surgical lasers and are highly absorptive in tissues due to their high water content. Light absorbing materials that can be coupled with $CO_2$ lasers that emit infrared light, such as light emitted at a 10.6 micron wavelength, to generate pressure waves include, but are not limited to, aqueous solutions such as saline, dextrose, radio-opaque contrast, lactated ringer's, and electrolyte solutions.

Nitrogen lasers can be used to produce low frequency, high energy laser pulses. Nitrogen lasers can emit light in the UV spectrum can emit laser light energy at a wavelength of about 337 nm and can be coupled with various light absorbing materials to generate pressure waves, including but not limited to, radio-opaque contrast as well as metals and oxides such as aluminum, silver, gold, copper, nickel, cerium, zinc, titanium, and dyes such as hydroxycoumarin and aminocoumarin.

Other medically useful lasers that can be used to generate a pressure wave to treat a vascular obstruction or restriction include Ti-Sapphire lasers, which can emit laser light energy at wavelengths of about 800 nm; Ruby lasers, which can emit laser light energy at wavelengths of about 694 nm; and Alexandrite lasers, which can emit laser light energy at about 755 nm. These medical lasers emit laser light energy in the near infrared light spectrum, and can be used for pressure wave generation. Light absorbing material or medium that can be coupled with these laser include, but are not limited to, dyes and colorants which could be used in solution, suspension, or coating on another material or surface within a device. Various materials capable of absorbing laser light energy in these wavelengths include aqueous copper, copper salts, and cupric sulfate, and materials such as fluorophores that are used in fluorescent microscopy (for example, methylene blue).

Dye lasers can also be used to generate pressure waves to treat a vascular occlusion. In some cases, dye lasers can be tuned to output a specific wavelength of light in the visible spectrum, which can allow for the optimization of the laser for a certain light absorbing material, as an alternative or in addition to, using a material which is highly absorptive of a specific wavelength of light. In this way, the light absorbing material can be any of the previously mentioned materials, as well as dyes, colorants, and visible light chromophores.

The force generated by the pressure waves 240 can also obviate the need to inflate the balloon 150 to the high pressures typically required to treat effectively a subject during angioplasty or other balloon procedures (for example, 14-16 atmospheres). In some cases, the balloon 150 of the present disclosure can be inflated with liquid medium 160 to pressures greater than 0 atmospheres to about 20.0 atmospheres. In some cases, the balloon 150 of the present disclosure can be inflated with liquid medium 160 to pressures between about 1.0 atmosphere to about 10.0 atmospheres. In other cases, the balloon 150 of the present disclosure can be inflated with liquid medium 160 to about 0.5, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0 atmospheres. The use of dilation balloon assemblies 150 at low pressures can reduce the potential for damaging healthy vascular tissue during a procedure, and can facilitate the treatment of a greater range and types of vascular obstruction or restrictions.

Figure 3A:
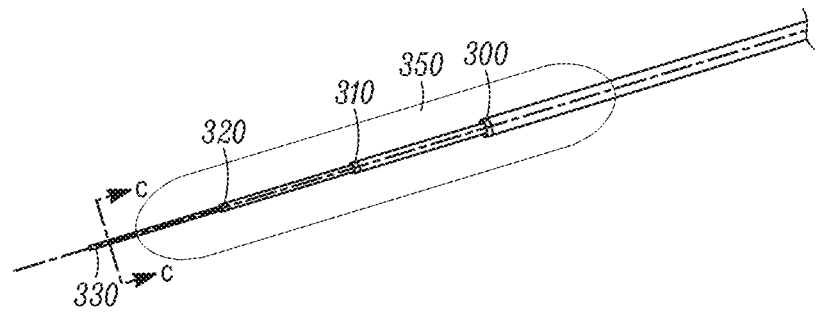
FIG. 3A is a representative perspective view of the distal end of a catheter with multiple concentric proximal emitters, according to one embodiment of the present disclosure.
Figure 3B:
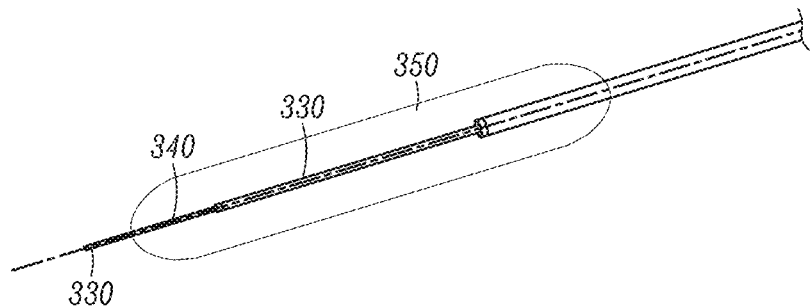
FIG. 3B is a representative perspective view of the distal end of a catheter with multiple single-fiber proximal emitters, according to one embodiment of the present disclosure.

In contrast to U.S. application Ser. No. 13/800,214, which published as US20140277002A1, and disclosed inflating a cutting or scoring balloon, followed by the use of pulsed laser light to cause the cutting or scoring elements to vibrate and assist in the cracking or abrading of the surrounding plaque, the balloon catheter of the present disclosure uses lower pressures, which may improve clinical outcomes. FIG. 3A is a representative perspective view of the distal end a catheter having multiple, telescopically extending, concentric proximal laser emitters 300, 310, 320 coupled to one or more laser catheters. Each of the concentric proximal laser emitters 300, 310, 320 is the termination point of an optical fiber layer that lies within a balloon catheter. By being positioned within the balloon catheter, the transmitted laser light energy can interact with the absorptive liquid medium in several locations along the distal end of the laser ablation catheter, thereby providing the ability to treat a greater range and types of vascular obstruction or restrictions. For example, the concentric proximal laser emitter 300 can be activated to treat a more proximally located vascular obstruction or restriction (with reference to the balloon catheter), while the concentric proximal laser emitter 320 can be activated to treat a more distally located vascular obstruction or restriction. Concentric proximal laser emitter 310 can be used to treat a vascular obstruction or restriction located somewhere in between. FIG. 3B is a representative perspective view of the distal end a catheter having multiple single-fiber proximal laser emitters 330, 340, in lieu of concentric proximal laser emitters. In any of the aforementioned configurations, the liquid medium ports may be arranged in one or more locations along each, or all, of the optical fiber layers.

Figure 3C:
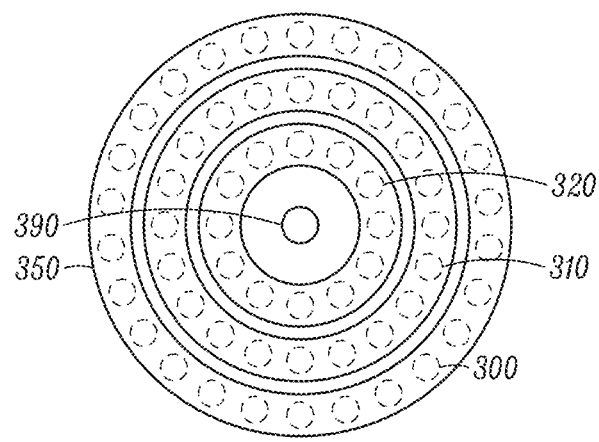
FIG. 3C is a representative cross-sectional view (through plane C in FIG. 3A) of the distal end of a catheter, according to one embodiment of the present disclosure.

FIG. 3C is a cross-sectional view (through plane C in FIG. 3A) of the distal end of a catheter showing multiple layers of optical fibers that terminate at proximal laser emitters 300, 310, 320, which are disposed within the balloon catheter 350. The catheter of FIG. 3C also includes a guidewire lumen to allow a guidewire 390 to be inserted therethrough, thereby facilitating the positioning of the distal end of the catheter within the vessel of a subject.

The multiple proximal laser emitters in FIGS. 3A and 3B can be activated in any sequence during a procedure, including individually or simultaneously with each other, thereby providing a greater range of treatment options. The number, size, and/or location of the emitters can be varied to customize the delivery of the laser light energy into the absorptive liquid medium. For example, multiple proximal laser emitters may decrease the overall pressure required in the balloon to have the same effect as that of a catheter with one or no proximal emitters. The emitters can be permanently fixed within a balloon catheter at the distal end of the catheter or they can be inserted any time during a procedure. Various other numbers and arrangements of proximal laser emitters can be used, depending on the characteristics of the vascular obstruction or restriction and the individual subject being treated, as can be appreciated by one of ordinary skill in the art based on the present disclosure. For example, the proximal laser emitters 300, 310, 320 need not be in multiple layers, but could be in a single layer with a single physical construction to create such emission.

Figure 4A:
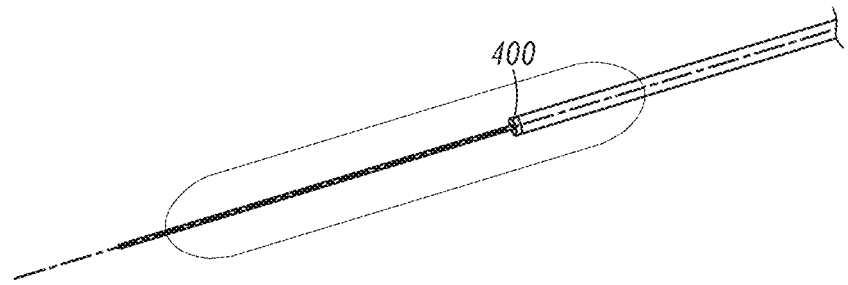
FIG. 4A is a representative perspective view of the distal end of a catheter with a translational proximal emitter in a first position within a balloon catheter, according to one embodiment of the present disclosure.
Figure 4B:
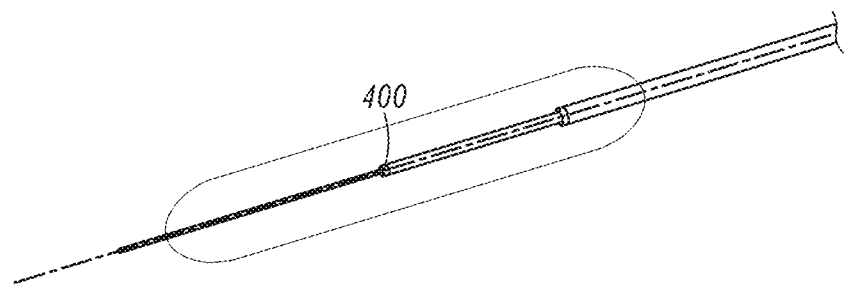
FIG. 4B is a representative perspective view of the distal end of a catheter with a translational proximal emitter in a second position within a balloon catheter, according to one embodiment of the present disclosure.
Figure 4C:
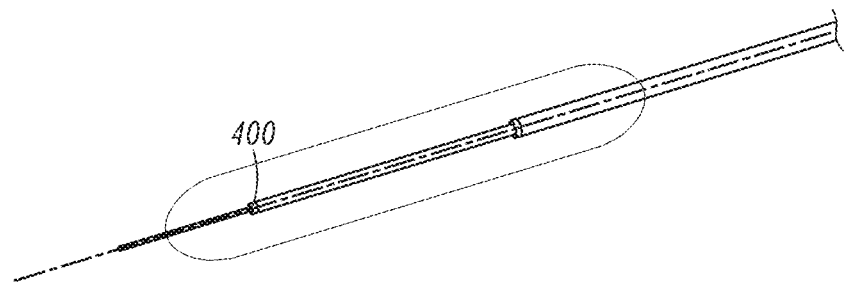
FIG. 4C is a representative perspective view of the distal end of a catheter with a translational proximal emitter in a third position within a balloon catheter, according to one embodiment of the present disclosure.

FIGS. 4A-4C are representative perspective views of the distal end of a laser balloon catheter with a translational proximal (such as, sliding) laser emitter 400 in three different positions within a balloon catheter. The translational proximal laser emitter 400 is the termination point of a layer of optical fibers configured to be translated longitudinally within the balloon catheter along the axis of the distal end of the catheter. This facilitates the use of the entire area of the balloon catheter during a procedure, or it facilitates the use of only a specific area of the balloon catheter during a procedure. FIG. 4A depicts the translational proximal laser emitter 400 in a more proximal position with reference to the balloon catheter; FIG. 4B depicts the translational proximal laser emitter 400 in a medial position with reference to the balloon catheter; and FIG. 4C depicts the translational proximal laser emitter 400 in a more distal position with reference to the balloon catheter. The ability to position the translational proximal laser emitter 400 before, during, or after a procedure provides for the treatment of a greater range and types of vascular obstruction or restrictions in a subject. In some cases, embodiments of the catheters described in FIGS. 3A and 3B may also incorporate the translational positioning of embodiments of the catheters described in FIGS. 4A-4C such that they can slide with respect to each other along the distal end of the catheter.

In some embodiments, catheters of the present disclosure can include a layer of optical fibers than can be translated longitudinally in and out of the balloon catheter along the axis of the distal end of the catheter. The balloon catheter can be coupled to an outer catheter on the catheter, and in some cases, the one or more emitters can be translated longitudinally to the distal tip of the catheter distal to (and externally from) the balloon catheter to, for example, emit light to ablate a portion of a vascular occlusion. In some embodiments, the one or more emitters can then be translated proximally into the balloon catheter, where the one or more emitters can be passed through a valve or opening in the catheter coupled to the balloon catheter such that the emitters can now emit light into a liquid medium contained within the balloon catheter to produce pressure waves to treat a vascular occlusion and/or deliver a therapeutic agent. Such embodiments can enable the use of only a single layer of optical fibers and/or emitters to perform both ablation and pressure wave propagation procedures.

The catheters of the present disclosure may be configured as separate components; for example, laser ablation catheter can be separate from the balloon catheter, and the laser ablation catheter may be inserted into the balloon catheter prior to the commencement of a procedure. The catheters of the present disclosure may also include one or more radiopaque markers positioned on the balloon catheter (for example, marking the proximal and distal ends of the balloon catheter) in order to assist with the placement of the distal end of the catheter at the desired location within the subject's vessel prior to the commencement of a procedure. The catheters of the present disclosure may also include one or more radiopaque markers positioned at and/or near the emitters in order to assist with the placement of the emitters within the balloon catheter, for example, such that the emitters are positioned adjacent to a vascular obstruction or restriction prior to the commencement of a procedure. Radiopaque markers can be made of any suitable materials known in the art, including but not limited to, platinum, iridium, and alloys thereof.

Figure 5:
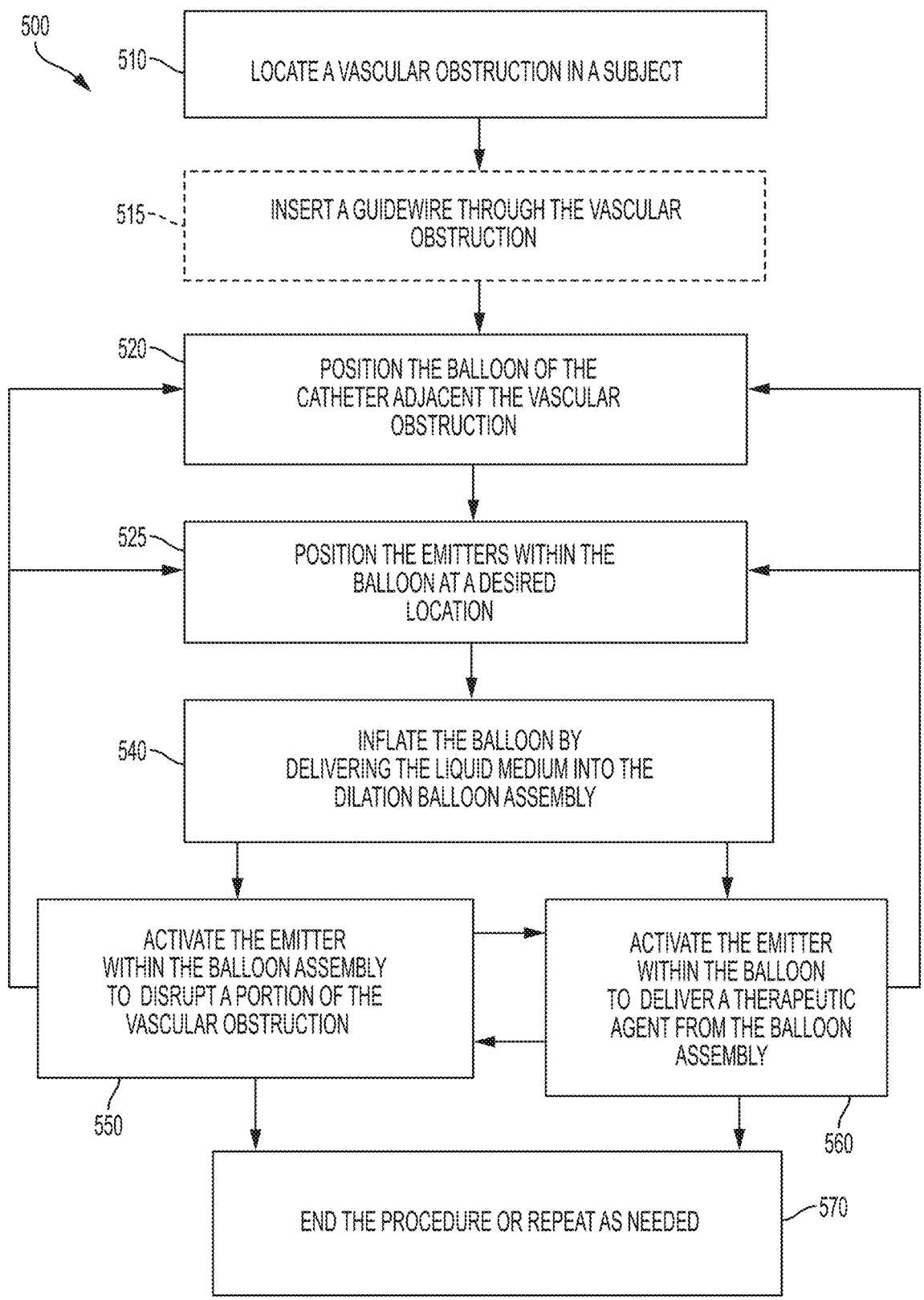
FIG. 5 is a representative flow diagram of methods of treating a subject using a catheter, according to one embodiment of the present disclosure.

Referring to the flow chart in FIG. 5, the present disclosure includes a method for treating a subject with a vascular obstruction or restriction 500 using embodiments of the catheter described herein. Although it is not illustrated in FIG. 5, it may be desirable to use a laser catheter to ablate at least a portion of the vascular occlusion in the vessel of the subject prior to performing the method set forth in FIG. 5 and/or using the a laser catheter to ablate at least a portion of the vascular occlusion in the vessel prior to and/or subsequent to performing any of the steps set forth in FIG. 5. The method 500 in FIG. 5 includes locating a vascular obstruction or restriction in the vessel of a subject 510. The next step, which is optional, includes locating a guidewire at the occlusion and/or inserting a guidewire through the occlusion 515. Thereafter, any of the embodiments of the catheters 100, 1000 described herein may be slid over the guidewire and into the vasculature such that the balloon catheter, which is coupled to the catheter 100, 1000, is positioned adjacent to the vascular obstruction or restriction 520. As discussed herein, the laser emitters within the balloon catheter may be fixed or slidable with respect to the balloon catheter. For example, if the laser emitters are included with the laser catheter, which is slidable within the catheter and balloon catheter of the balloon catheter, the emitters may be positioned (and subsequently re-positioned) anywhere along the length of the balloon at a desired location. Additionally or alternatively, the method 500 includes inflating the balloon catheter by delivering the liquid medium (for example, contrast medium) from the inner lumen of the catheter through one or more liquid medium ports and into the balloon catheter 540. In some cases, the method 500 includes activating at least one laser emitter enclosed within the balloon catheter to emit and send pulses of laser light energy into and/or to react with the liquid medium to produce propagating pressure waves and disrupt a portion of the vascular occlusion 550. In some cases, the method 500 includes activating at least one laser emitter enclosed within the balloon catheter to emit and send pulses of laser light energy into and/or to react with the liquid medium to produce propagating pressure waves to deliver a therapeutic agent to the vascular obstruction or restriction and/or the vascular tissue near the obstruction or restriction 560. Activating a proximal laser emitter to disrupt a portion of a vascular obstruction or restriction and/or to deliver a therapeutic agent can be performed in any sequence, if at all, as part of the method 500. For example, step 550 could be performed without performing step 560, step 560 could be performed without performing step 550, step 550 could be performed serially while performing step 560, such that step 550 is performed firstly and step 560 is performed secondly, step 550 could be performed serially while performing step 560, such that step 560 is performed firstly and step 550 is performed secondly, or steps 550 and 560 could be performed in parallel. Upon completing step 550 and/or step 560, the balloon catheter can optionally be repositioned within the vasculature and adjacent another portion thereof. Similarly, upon completing step 550 and/or step 560, the emitter(s) can optionally be repositioned within the balloon catheter. Either or both the balloon catheter can be repositioned within the vasculature or the emitter(s) within the balloon catheter can be repositioned. The method 500 also includes ending the procedure when the desired therapeutic outcome is obtained, or repeating any of 510 through 560 as may be necessary to treat a subject having a vascular obstruction or restriction. Furthermore, if step 560 is not performed in the method depicted in FIG. 5, a drug eluting (coated) balloon (DEB or DCB) catheter may be used to deliver drugs to the remnants of the vascular occlusion. Disrupting the vascular occlusion with the pressure waves prior to utilizing a DEB may increase the effectiveness of the drugs being applied to the vascular occlusion because to the pressure waves disrupt the intraluminal as well as medial (within the tissue layer of the vascular wall) vascular obstruction or restrictions (for example, calcium deposits), thereby creating a pathway for the drug to enter the intraluminal and medial portions of the vasculature and/or vascular occlusion.

Although the method illustrated in FIG. 5 depicts step 520, which includes positioning the balloon catheter adjacent the vascular occlusion, being performed prior to step 525, which includes positioning the emitters within the balloon catheter at a desired location, step 525 may be performed after or in parallel with step 520. Additionally, although the method illustrated in FIG. 5 depicts step 520 and step 525 as occurring prior to step 540, which includes inflating the balloon catheter with liquid medium, step 540 may be performed prior to or in parallel with one or both of step 520 or step 525. That is, steps 520, 525 and 540 may be performed in any order.

Additionally or alternatively, methods of the present disclosure also include activating at least one proximal laser emitter enclosed within the balloon catheter to emit pulses of laser light energy to react with and/or to react with the liquid medium and propagating pressure waves to assist in stent deployment. Cavitation bubbles generated by pulsing laser light energy, which reacts with the liquid medium and can assist in seating or expanding the stent to its full diameter as part of a medical procedure.

Although a large portion of this disclosure includes a discussion of laser ablation catheters used in conjunction with a balloon catheter, catheters having mechanical cutting instruments may also be used. Laser catheters typically transmit laser energy through emitters housed in a relatively flexible tubular catheter inserted into a body lumen, such as a blood vessel, ureter, fallopian tube, cerebral artery and the like to remove obstruction or restrictions in the lumen. Catheters used for laser angioplasty and other procedures may have a central passageway or tube which receives a guidewire inserted into the body lumen (for example, vascular system) prior to catheter introduction. The guidewire facilitates the advancement and placement of the catheter to the selected portion(s) of the body lumen for laser ablation of tissue.

Examples of laser catheters are sold by The Spectranetics Corporation under the tradenames ELCA™ and Turbo Elite™ (each of which is used for coronary or peripheral intervention or catheterization such as recanalizing occluded arteries, changing lesion morphology, and facilitating stent placement) and SLSII™ and GlideLight™ (which is used for surgically implanted lead removal). The working (distal) end of a laser catheter typically has a plurality of emitters that emit energy and ablate the targeted tissue. The opposite (proximal) end of a laser catheter typically has a coupler, which connects to a laser system or generator. One such example of a laser system is the CVX-300 Excimer Laser System, which is also sold by The Spectranetics Corporation, and is illustrated in FIG. 9, which has been previously discussed herein.

Traditional balloon catheter typically includes a two-catheter construction such that an inner catheter is disposed within an outer catheter, and the inner catheter extends beyond the distal end of the outer catheter. A balloon is coupled to the inner catheter and outer catheter. Incorporating a laser ablation catheter between the inner catheter and outer catheter of a balloon catheter, however, increases the overall size and diameter of the balloon catheter, thereby potentially limiting the ability of the balloon catheter to reach and treat smaller sized vessels, such as peripheral arteries below the knees, particularly those arteries located within the feet. It is, therefore, desirable to reduce the overall size and diameter of the balloon catheter, including the size and diameter of the catheter(s) and/or the balloon. Reducing the overall size and diameter of the balloon catheter will, therefore, increase the balloon catheter's ability to reach and treat smaller sized peripheral arteries and other smaller sized vasculature.

One potential solution for reducing the overall size and diameter of the balloon catheter is to remove the inner catheter, which will allow the balloon and outer catheter (now just one catheter) to be sized smaller. Removing the inner catheter, however, removes (a) the lumen through which the guidewire travelled and (b) the component to which the balloon was coupled and (c) the ability to seal the inflation medium used to inflate the balloon. What is, therefore, needed is a means for coupling the distal portion of the balloon while allowing a guidewire to pass therethrough and for providing a seal with the guidewire upon introduction of the inflation medium into the balloon.

Figure 10B:
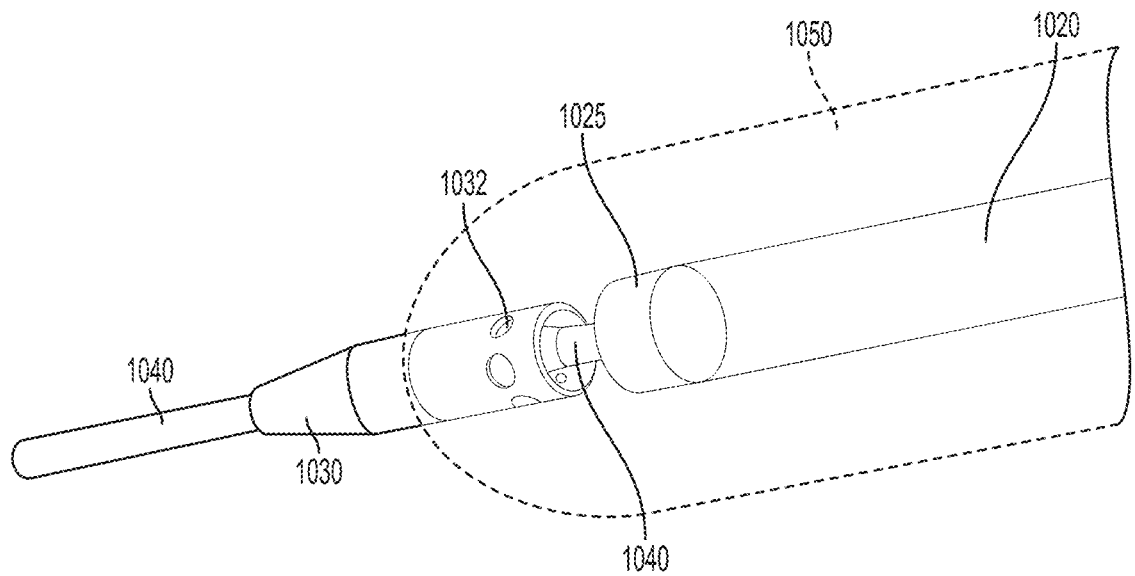
FIG. 10B is an enlarged representative perspective view of the distal end of the balloon catheter and laser ablation catheter illustrated in FIG. 10, wherein a sealable valve is illustrated at the distal end of the balloon.
Figure 11:
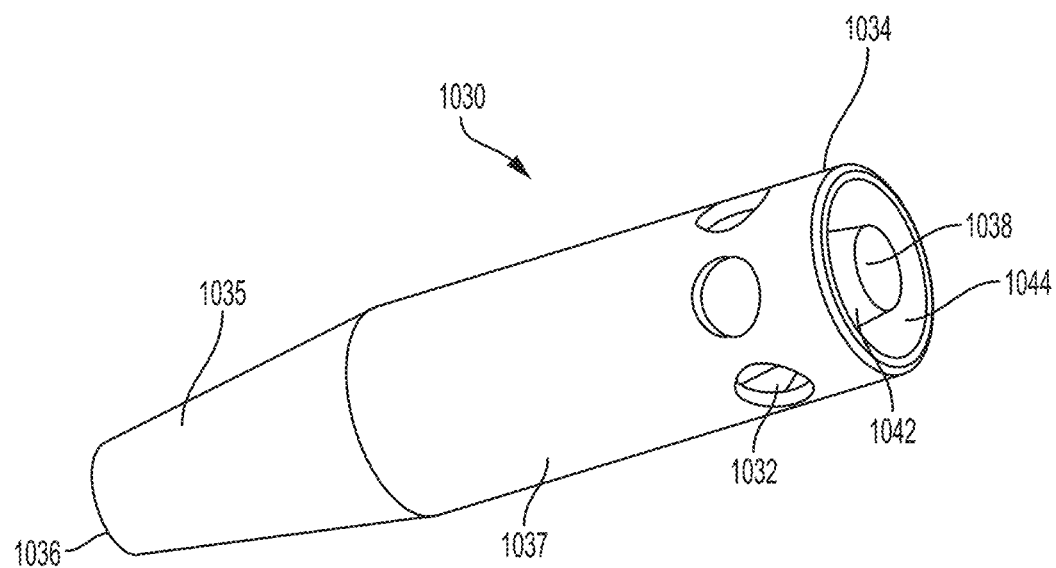
FIG. 11 is an enlarged representative perspective view of the sealable valve depicted in FIGS. 10, 10A and 10B.

Referring to FIGS. 10 and 10A and 10B, there is depicted the distal end of an alternative system for treating an obstruction or restriction within vasculature of a subject that includes such a means and omits a stationary inner catheter, which is typically included within a traditional balloon catheter. The system comprises a catheter 1000 and a laser catheter 1020 insertable and slidable within the catheter 1000. The catheter 1000 includes a catheter 1010 with a lumen (not shown) extending form its proximal end to its distal end, a tip 1030, and a balloon 1050 coupled to the tip 1030 and a distal portion of the catheter 1010. The catheter 1000 does not include a catheter (with a lumen) extending between the distal end of the catheter 1010 and the proximal end of the tip 1030 within the balloon. The system further comprises a laser catheter 1020 comprising a proximal portion, distal portion 1025, which may be protected by a smooth outer metal band, one or more emitters disposed within the laser catheter 1020, and at least one energy source (not shown) coupled to the one or more emitters and exposed at the distal portion 1025 of the laser catheter 1020 within the balloon 1050. The at least one or more emitters extend from the proximal portion of the laser catheter 1020, which is coupled to a laser generator, as discussed with respect to FIG. 9 hereinbefore, Referring to FIGS. 11, 11A, and 11B, the tip 1030 includes a proximal end 1034, a distal end 1036 and a lumen 1038 extending therethrough from its proximal end 1034 to its distal end 1036. The tip 1030 includes a valve that seals the intersection of the tip 1030 and the guidewire 1040 as the guidewire 1040 passes through the guidewire lumen 1038. One example of a valve is that which is depicted in FIGS. 11, 11A, and 11B which illustrate a flange 1046 that is disposed at and/or toward the proximal end 1034 of the tip 1030.

Referring back to FIGS. 10, 10A, and 10B, the balloon 1050 is coupled to the distal end of the catheter 1010 and the tip 1050. Upon introducing the guidewire 1040 through the lumen of the catheter 1010 and into the guidewire lumen 1038 of the tip, the catheter 1010 and tip 1030 are slidably coupled such that the catheter 1010 and tip 1030 can slide over the guidewire 1040, as depicted in FIG. 11A. As illustrated in this figure, there is a gap (or opening) caused by the guidewire lumen 1038 between the flange 1046 and the guidewire 1040. If the gap is maintained during introduction of the inflation medium into the balloon 1050, the inflation medium would travel through the guidewire lumen 1038 and into the patient's vasculature, which may be undesirable. The flange 1046, which may include a tapered portion 1042 that tapers from the tip's distal end toward its proximal end, is configured to radially collapse upon introduction of the inflation medium into the balloon 1050 due to the increased fluid pressure on the flange 1046. The increased fluid pressure on the flange 1046 actuates the flange 1046 and moves it radially inward toward the guidewire lumen 1038 such that the gap between flange 1046 and the guidewire 1040 closes, thereby creating a seal between the between flange 1046 and the guidewire 1040, as depicted in FIG. 11B. The reduced thickness of the tapered portion 1042 of the flange 1046 as the flange 1046 tapers radially inward towards the guidewire lumen 1038 as the flange 1046 progresses from the distal end 1036 toward the proximal portion 1034 increases the flange's ability to flex upon exposure to the pressure created upon introduction of the inflation fluid. Upon removal of the inflation medium from the balloon 1050, the pressure within the balloon 1050 decreases, the pressure on the flange 1046 decreases, and the flange 1046 naturally retracts to its original position as depicted in FIG. 11A, thereby reestablishing the gap between the tip 1030 and the guidewire 1040 so that the two components may slide with respect to one another. Accordingly, the flange 1046 acts as a sealable valve within the tip 1030, and the flange 1046 is actuated with the introduction and removal of the inflation medium into and from the balloon 1050.

Figure 11A:
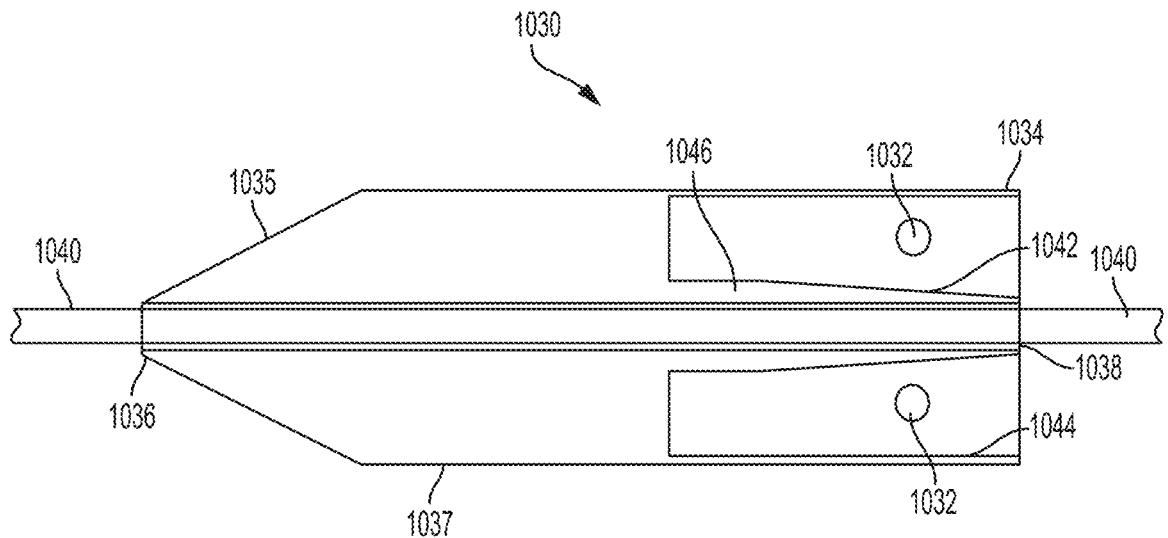
FIG. 11A is an enlarged representative cross-sectional side view of the sealable valve in an unsealed configuration with respect to a guidewire.
Figure 11B:
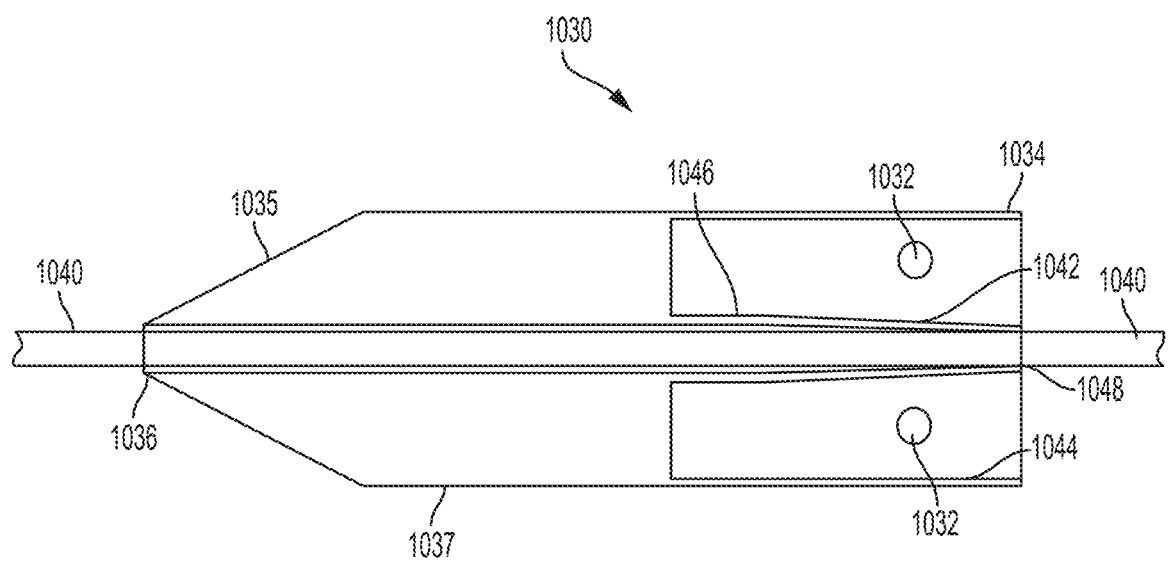
FIG. 11B is an enlarged representative cross-sectional side view of the sealable valve in a sealed configuration with respect to a guidewire.

Although the tapered portion 1042 illustrated in FIGS. 11A and 11B tapers from the tip's distal end toward its proximal end, the direction of the taper may be reversed such that the tapered portion tapers from the tip's proximal end toward its distal end. Additionally, the flange 1046 may taper towards any portion along its length such that a portion of the flange is thinner at one or more locations along its length in comparison to other locations along its length. Accordingly, upon an increased fluid pressure being imparted on the flange 1046, thinner portion of the flange 1046 actuates and moves radially inward toward the guidewire lumen 1038 such that the gap between flange 1046 and the guidewire 1040 closes, thereby creating a seal between the between flange 1046 and the guidewire 1040.

FIGS. 10, 10A, 10B, 11, 11A, and 11B, do not illustrate an inflation lumen through which the inflation medium is introduced and removed from the balloon. Nevertheless, the catheter 1010 may also include a separate inflation lumen (not shown) integrally located within the structure of the catheter 1010 itself or the inflation medium may be introduced into the balloon 1050 through an opening (or gap) between the laser catheter 1020 and the catheter 1010. For the purposes of this disclosure, the inflation shall include both the separate inflation lumen integrally located within the structure of the catheter 1010 itself and an opening (or gap) between the laser catheter 1020 and the catheter 1010.

Referring again to FIGS. 11, 11A, and 11B the tip 1030 may be constructed from any type of compressible or compliant biopolymers, such as silicones or flouro-polymers, compliant adhesives, etc. The configuration of the tip 1030 depicted in these figures includes an exterior wall 1044 and a flange 1046 disposed radially therein, to create a gap therebetween for the inflation medium to enter and actuate the flange 1046. The flange is also depicted as being disposed toward the proximal end 1024 of the tip 130, which itself is depicted as tubular, and its distal end has an inward taper that tapers distally from the exterior wall 1044 towards the guidewire lumen 1038. Although the tip 1030 is depicted as including particular components and shapes, the present disclosure shall include other shapes and components known to one of skill in the art. Moreover, the tip may alternatively include a self-sealing tube constructed of any type of compressible or compliant biopolymers, such as silicones or flouro-polymers, compliant adhesives, etc. For example, the tip may include a tube that has a lumen passing therethrough such that upon insertion of a guidewire, the lumen expands, and upon removable of the guidewire, the lumen contracts, thereby appearing as a slit.

As discussed above, omitting a stationary inner catheter form a traditional balloon catheter and including a tip distally disposed from the catheter of the balloon catheter has the advantage of reducing the size of the balloon, and hence smaller sized balloons can enter smaller vessels, particularly peripheral arteries below the knee. Additionally, when a traditional balloon catheter is inflated with liquid, such as saline (and possibly with a contrast medium), air may become trapped and unable to escape from the balloon. The tip 1030, particularly the actuation of the flange 1046, which acts as sealable valve within the tip 1030, allows the air initially included within the balloon to escape during inflation, thereby potentially increasing the balloon's ease of use, as well as its effectiveness. For example, during preparation of the balloon, it is common to deflate the balloon, thereby extracting as much air as possible, prior to use. However, it is impractical to remove all of the air during such extraction process. The tip 1030, thereby allows a user to remove more or all air from the balloon during preparation. Additionally, it may not be necessary to deflate the balloon and remove any air prior to use, because the air is allowed to escape during inflation with the liquid.

Continuing to FIGS. 10, 10A, 10B, 11, 11A, and 11B, the tip 1030 may include one or more openings 1032 through its exterior wall 1044. The openings 1032 allow the inflation liquid to reach the flange 1046 not only from the gap between the flange 1046 and the exterior wall 1044 at the proximal end 1034 of the tip 1030 but also at a location distal the proximal end 1034 of the tip 1030. Allowing allow the inflation liquid to reach the flange 1046 at or toward its distal portion, potentially increases the likelihood and effectiveness of actuating the flange 1046. Although the tip 1030 is illustrated as having a tubular section 1037 from its proximal end 1034 and a tapered section 1035 from the end of its tubular section toward the tips distal end 1036, the scope of this disclosure shall include other shapes for the tip.

As discussed herein, as the laser light is emitted from the emitter(s), the light interacts with the liquid medium, and the liquid medium absorbs the light energy, thereby creating vapor bubbles within the balloon catheter. The openings 1032 within the tip 1030 may reduce the size of the bubble formed within the balloon catheter and/or reduce the likelihood that the bubble will expand toward the distal end of the balloon catheter.

Additionally, although FIGS. 10, 10A, 10B, 11, 11A, and 11B include a tip 1030 included within a balloon catheter that omits a stationary inner catheter, the scope of this disclosure includes utilizing a tip 1030 in a balloon catheter that includes an inner catheter in addition to an outer catheter to which the proximal end of the balloon is attached.

As discussed above, transmitting pulses of laser light energy from an emitter into a liquid medium generates a plurality of propagating laser-induced pressure waves that cause the balloon catheter, which surrounds the liquid medium, to engage and disrupt at least a portion of the vascular obstruction or restriction. The catheter, which the balloon catheter, and the balloon itself, may each include a guidewire lumen through which a guidewire can pass and cross the occlusion. It may also be desirable to excite and vibrate the guidewire to increase the guidewire's ability to pierce and cross the occlusion. Accordingly, the present disclosure also contemplates directing the laser-induced pressure wave and/or cavitation event toward the guidewire lumen and/or guidewire such that the pressure waves excite and vibrate the guidewire.

Figure 6:
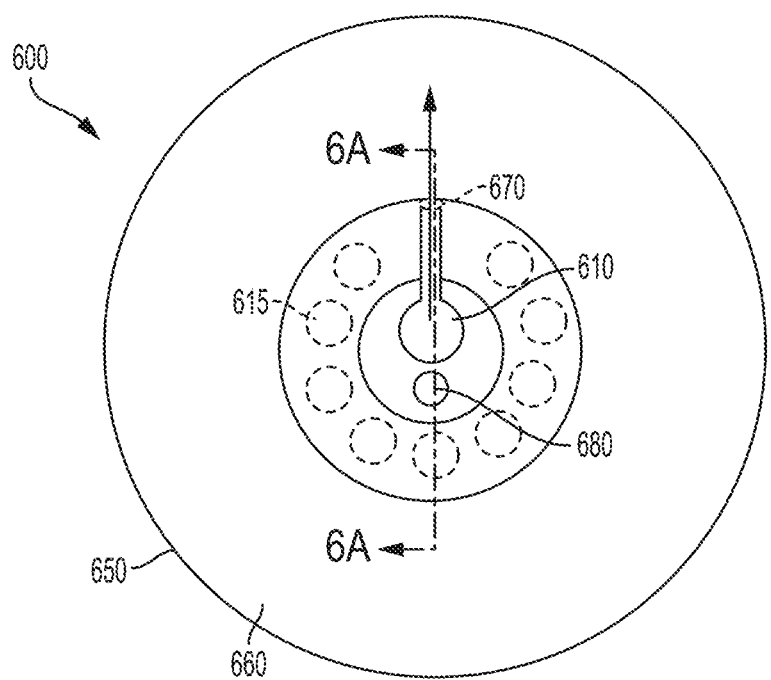
FIG. 6 is a representative end view of the distal end of a catheter with the balloon catheter in a partially inflated configuration, according to one embodiment of the present disclosure.

Referring to FIG. 6, there is depicted an end view of the distal end of a catheter 600 within a balloon catheter 650 in a partially inflated configuration, according to one embodiment of the present disclosure. As shown, the distal end of the catheter 600 includes one or more emitters 615 arranged circumferentially around an inner inflation lumen 610 and an inner guidewire lumen 680. The emitters 615 extend to the distal tip of the catheter and terminate at the distal emitter 620 within the balloon catheter 650.

In the inflated or partially inflated configuration shown in FIG. 6, the balloon catheter 650 is inflated with liquid medium 660. The liquid medium 660 is delivered into the balloon catheter 650 via one or more liquid medium ports 670. The liquid medium port(s) 670 may also serve as a means for removing the liquid medium to modulate the pressure within the balloon (for example, different pressures required by different procedures) and to deflate the balloon catheter 650.

The ability of liquid medium 660 to absorb light energy can degrade after prolonged exposure to the light energy. Liquid medium 660 can be removed from the balloon catheter 650 through a separate set of liquid medium ports that act as liquid medium exit ports. Liquid medium exit ports can, for example, be configured to allow for the slow purgation or exchange of liquid medium 660 through an inner lumen in the catheter, while not significantly altering the overall pressure within the balloon catheter itself.

Figure 6A:
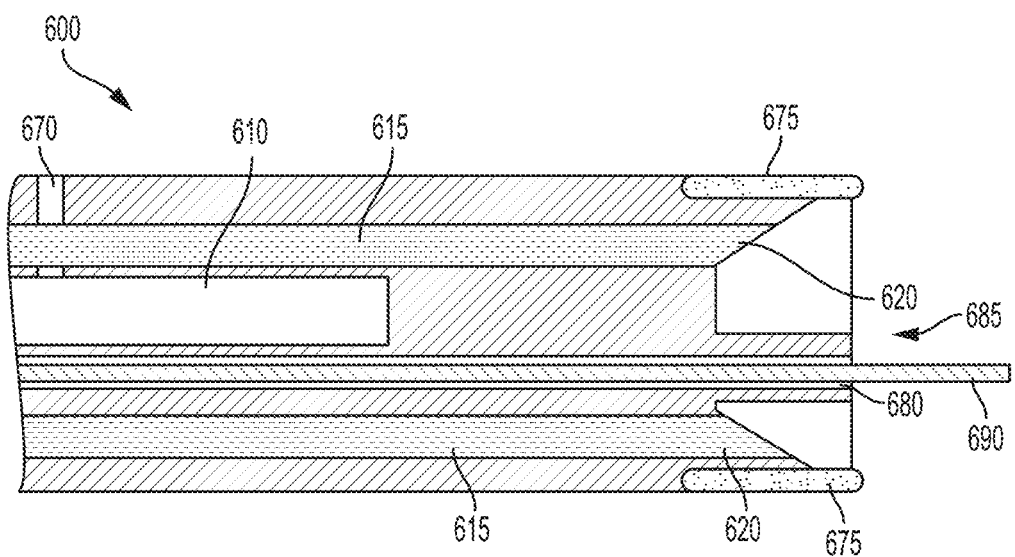
FIG. 6A is a representative cross-sectional view of the distal end of the catheter illustrated in FIG. 6 through plan A-A, according to one embodiment of the present disclosure.
Figure 6A:
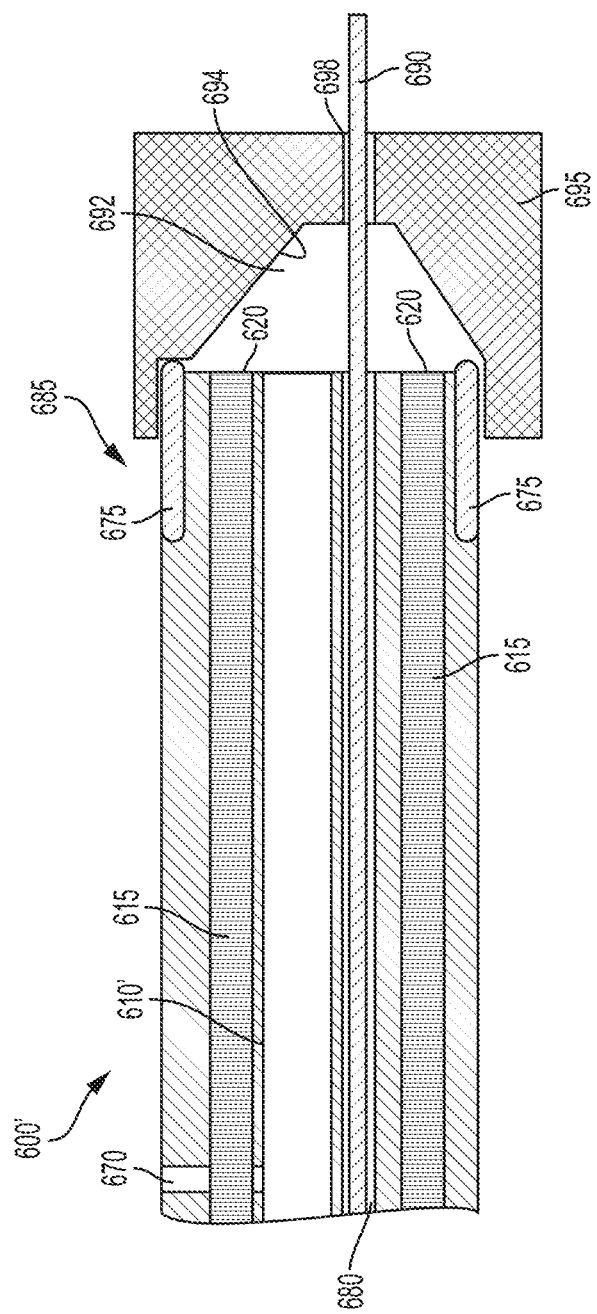

FIGS. 6 and 6A depict the inner inflation lumen 610 and the inner guidewire lumen 680 in a radially offset configuration with respect to the longitudinal axis of the catheter 600. That is, the inflation lumen 610 and the inner guidewire lumen 680 are eccentrically oriented with respect to one another and with respect to the longitudinal axis of the catheter 600. Either the inner inflation lumen 610 or the inner guidewire lumen 680, however, may be concentrically located with respect to the longitudinal axis of the catheter 600.

Additionally, FIG. 6A depicts the inflation lumen 610 terminating within the catheter 600, and the guidewire lumen 680 extending through the distal tip 685 of the catheter 600. The inflation lumen 610, however, may alternatively extend through the distal tip of the catheter such that the liquid medium not only enters the balloon catheter 650 through the one or more liquid medium ports 670, but the liquid medium can also enter the balloon catheter 650 though the opening of the inflation lumen 610 through the distal tip 685 of the catheter 600, or the liquid medium can also enter the patient's vasculature though the opening of the inflation lumen 610 through the distal tip 685 of the catheter 600. Furthermore, although FIG. 6 illustrates only one liquid medium port 670, the catheter 600 may include a plurality of liquid medium ports fluidly coupled to the inflation lumen 610 and disposed concentrically around the perimeter of the laser catheter 600 to inflate the balloon catheter 650 with the liquid medium 660.

Continuing to refer to FIG. 6A, in addition to having a plurality of emitters 615, an inflation lumen 610, one or more liquid medium ports 670, and a guidewire lumen 680, the catheter 600 may also include an outer band 675 that surrounds the distal tip 685, thereby increasing the strength and rigidity of the distal tip. As mentioned above, the present disclosure, particularly the embodiment included in FIG. 6A, co contemplates directing the laser-induced pressure wave and/or cavitation event toward the guidewire lumen 680 and/or the guidewire 690 such that the pressure waves excite and vibrate the guidewire 690. A means for directing the laser-induced pressure wave and/or cavitation event towards the guidewire lumen 680 or the guidewire 690 within the guidewire lumen includes disposing the emitter(s) 620 proximate the distal end 690 of the catheter 600 and/or proximate the distal end of the outer band 675 such that the emitter(s) 620 is recessed from the distal tip 685 of the catheter 600 and/or proximate the distal end of the outer band 675 along the longitudinal axis of the catheter. By recessing the emitter(s) 620 from the distal tip 685 of the catheter 600 and/or proximate the distal end of the outer band 675, the laser-induced pressure wave and/or cavitation event may be directed toward the guidewire lumen 680 and/or the guidewire 690.

An additional means for directing the laser-induced pressure wave and/or cavitation event towards the guidewire lumen 680 or the guidewire 690 within the guidewire lumen includes directing the emitter(s) 620 toward the guidewire lumen 680 or the guidewire 690. For example, as discussed above, the terms "emitter" as used herein may refer to an end portion of a fiber or an optical component that emits light from a distal end thereof. The emitter 620 is directed towards the guidewire lumen 680 and/or the guidewire 690 because the optical fiber is tapered in a manner that the light emitted therefrom is directed radially inward towards the guidewire lumen 680 and/or the guidewire 690. As illustrated in FIG. 6A, the guidewire lumen 680 and/or guidewire 690 may extend longitudinally distal of the emitter 620. Accordingly, as the laser light is emitted from the emitter(s) 620, the light interacts with the liquid medium, and the liquid medium absorbs the light energy, thereby creating vapor bubbles and cavitation events therein and/or producing resultant laser-induced pressure waves that cause the guidewire lumen 680 and/or guidewire 690 to excite and/or vibrate.

Referring to FIG. 6A', there is depicted an alternate embodiment of the present disclosure, particularly an alternate embodiment of a means for directing the laser-induced pressure wave and/or cavitation event towards the guidewire lumen 680 or the guidewire 690. Similar to the embodiment discussed above with respect to FIG. 6A, the embodiment in FIG. 6A' includes a catheter 600' having a plurality emitters 615, an inflation lumen 610, one or more liquid medium ports 670, and a guidewire lumen 680, and an outer band 675 that surrounds the distal tip 685. This embodiment also includes a cap 695 having a guidewire lumen 698 extending therethrough.

The cap 695 can be either removably coupled to the catheter 600', particularly removably coupled to the outer band 675, or the cap can be permanently affixed to the catheter 600', particularly permanently affixed to the outer band 675. The cap 695 includes a proximal (for example, interior) side 694 and a distal (for example, exterior) side. The interior side 694 can be tapered such that a cavity 692 forms between the distal end of the catheter 600' and the interior side 694 of the cap 695, thereby allowing the liquid medium to enter and collect within the cavity 692 after exiting the inflation lumen 610'. Although FIG. 6A' is depicted as having a catheter 600' with a flush distal end and a tapered, recessed cap 695 to create a cavity between the catheter 600' and the cap for the liquid medium to collect, the present disclosure also contemplates having catheter with a recessed distal end, as depicted in FIG. 6A, that could be used in conjunction with a cap having a flush or recessed interior side to create a cavity for the liquid medium to collect. Accordingly, as the laser light is emitted from the emitter(s) 620, the light interacts with the liquid medium within the cavity 692, and the liquid medium absorbs the light energy, thereby creating vapor bubbles and cavitation events therein and/or producing resultant laser-induced pressure waves that can cause the guidewire lumen 680 and/or guidewire 690 to excite and/or vibrate.

Figure 7:
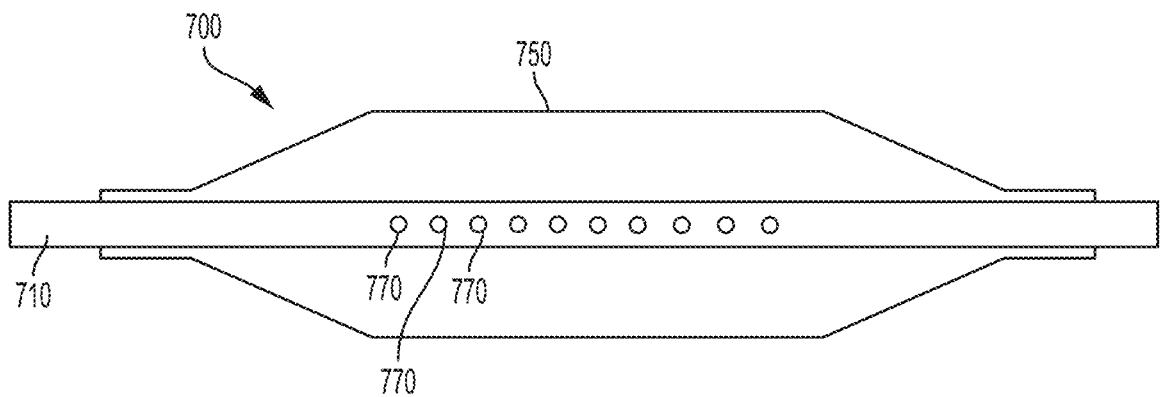
FIG. 7 is a representative cross-sectional view of a catheter, according to an alternate embodiment of the present disclosure, wherein a balloon comprises a pressure-wave reflective material.

Referring to FIG. 7, there is depicted an alternate embodiment of the catheter 700 of the present disclosure, particularly an alternate embodiment of a means for directing the laser-induced pressure wave and/or cavitation event towards the guidewire lumen 710 or the guidewire (not shown). As discussed above, the laser light is emitted from the emitter(s), the light interacts with the liquid medium (introduced into the balloon catheter 750 through ports 770), and the liquid medium absorbs the light energy, thereby creating vapor bubbles and cavitation events therein and/or producing resultant laser-induced pressure waves within the balloon catheter 750. This embodiment comprises the inclusion of pressure-wave reflective material in the balloon 750 such that upon the pressure waves reaching the pressure-wave reflective material in the balloon, the reflective material re-directs at least a portion of the laser-induced pressure wave toward the guidewire lumen 710 and/or guidewire (not shown) to excite and/or vibrate.

The pressure-wave reflective material may include a polymer having a higher or harder durometer in comparison to the materials traditionally used in balloons, such as polyethylene, polyurethane, and polytetrafluoroethylene. The increased durometer and hardness of the pressure-wave reflective material may be achieved by including a filler within the polymer matrix of a single layered balloon, increasing the cross-linking between polymer within the single layered balloon, selecting a harder polymer (in comparison to the traditional balloon materials), or co-extruding an additional harder polymer layer with the traditional polymer layer. If a co-extruded construction is used to manufacture the balloon, then the harder layer may be included on either the interior or exterior of the balloon, and the traditional layer having the lower hardness will be on the opposite side of the balloon. Additionally, a three layered co-extruded structure may be used to manufacture the balloon such that the harder layer is sandwiched between two traditional lower durometer layers.

Figure 8:
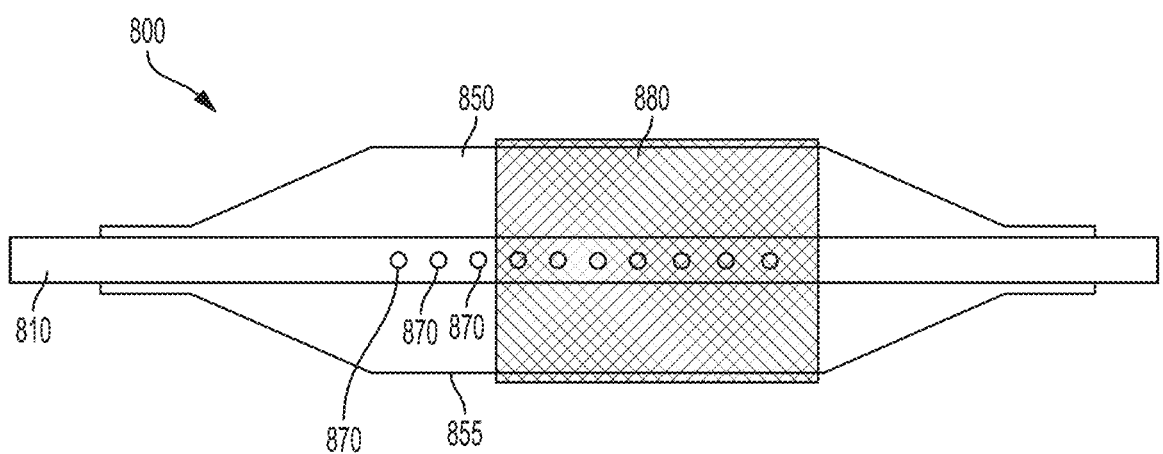
FIG. 8 is a representative cross-sectional view of a catheter, according to an alternate embodiment of the present disclosure, wherein a balloon comprises an alternative pressure-wave reflective material.

Referring to FIG. 8, there is depicted another alternate embodiment of the catheter 800 of the present disclosure, particularly an alternate embodiment of the catheter that comprises a pressure-wave reflective element 880 over the balloon 850. The pressure-wave reflective element 880 has multiple purposes, namely (1) the pressure-wave reflective element 880 reduces or prevents the formation of vapor bubbles exterior of the pressure-wave reflective element 880 and/or the balloon 850, (2) upon the pressure waves reaching the pressure-wave reflective element 880, the reflective element 880 re-directs at least a portion of the pressure waves toward the guidewire lumen 810 and/or guidewire (not shown) to excite and/or vibrate the guidewire, and (3) the pressure-wave reflective element 880 reinforces the balloon 850, Accordingly, the pressure-wave reflective element 880 is (1) a means for reducing or preventing the formation of cavitation bubbles exterior of the pressure-wave reflective element 880 and/or the balloon 850, (2) a means for re-directing at least a portion of the pressure waves toward the guidewire lumen 810 and/or guidewire to excite and/or vibrate the guidewire, and/or (3) a means for reinforcing the balloon 850.

Although the pressure-wave reflective element 880 is illustrated over the balloon 850 in FIG. 8, the pressure-wave reflective element 880 may be on the inside (interior) of the balloon 850, such as an inside layer, or the pressure-wave reflective element 880 may be incorporated or integrated into the balloon 850 itself. Additionally, the pressure-wave reflective element 880 may cover a portion of the balloon 850, as depicted in FIG. 8, or the pressure-wave reflective element 880 may cover the entire balloon 850. Regardless of whether the pressure-wave reflective element 880 is directly or indirectly coupled to the balloon 850, the pressure-wave reflective element 880 is capable of expanding and contracting with the balloon 850. Accordingly, both the pressure-wave reflective element 880 and the balloon 850 have an expanded state and a contracted state.

The pressure-wave reflective element 880 may be directly coupled to the working portion 855 of the balloon 850 or indirectly coupled to the working portion 855 of the balloon 850. The pressure-wave reflective element 880 may be directly coupled to the working portion 855 of the balloon 850 by being affixed to the working portion 855 by a chemical bond, mechanical fixation or some other means of affixation. The pressure-wave reflective element 880 may be indirectly coupled to the working portion 855 of the balloon 850 by directly coupling the pressure-wave reflective element 880 to the proximal end of the balloon 850, the distal end of the balloon 850, the tapered ends of the balloon, and/or the catheter, including the structure that creates the guidewire lumen. Indirectly coupling the pressure-wave reflective element 880 to the working portion 855 of the balloon 850 allows the pressure-wave reflective element 880 to expand and contract with the balloon 850 upon inflation and deflation, respectively, but it also allows the pressure-wave reflective element 880 to expand and contract in a manner such that the pressure-wave reflective element 880 is not permanently attached to the working portion 855 of the balloon 850. That is, indirectly coupling the pressure-wave reflective element 880 to the working portion 855 of the balloon 850 allows the pressure-wave reflective element 880 to expand and contract separately from the balloon 850 but respectively with the balloon.

The pressure-wave reflective element 880 may be constructed of a biocompatible material, including either a polymeric material or a metallic material, such as nitinol, which is a nickel-titanium alloy. The pressure-wave reflective element 880 may be a solid structure or a porous scaffolding structure, as shown in FIG. 8. As discussed in more detail below, the present disclosure contemplates that the pressure-wave reflective element 880 may comprise various shapes and configuration. For example, the sizes of the pores or openings within the scaffolding structure may be adjusted to control the amplitude or direction of the pressure waves approaching the target tissue.

Regarding the pressure-wave reflective element's ability to reduce or prevent the formation of vapor bubbles exterior of the pressure-wave reflective element 880 and/or the balloon 850, it may be preferable for the pressure-wave reflective element 880 to be porous and thereby have openings 885. Referring to FIGS. 15A-15F, the openings 885 within the pressure-wave reflective element 880 may prevent the formation of large sized vapor bubbles on the exterior of the balloon 880. The openings 885 not only allow the pressure waves to pass therethrough, but the quantity and size of the openings 885', particularly with respect to the remainder of the structural mass 887 (or portions thereof) of pressure-wave reflective element 880, may also limit the size of the vapor bubbles that can form on the exterior of the balloon 850. The relationship between the open area and the closed area (or the ratio of the open area to the overall area) within the pressure-wave reflective element 880 should be such that a sufficient amount of the pressure waves pass through the pressure-wave reflective element 880. And the size of the openings 885 should allow the pressure waves to pass therethrough, while also limiting the size of the vapor bubbles that can form on the exterior of the balloon 850. Accordingly, it may be desirable for the percentage of the open area to the overall area of the pressure-wave reflective element 880 to be between 1 percent-99 percent, including any increment therebetween such as 2 percent, 3 percent, 4 percent, 5 percent, 6 percent, 7 percent, 8 percent, 9 percent, 10 percent, . . . , 15 percent . . . 20 percent, . . . , 25 percent, . . . , 30 percent, . . . , 35 percent, . . . , 40 percent, . . . , 45 percent, . . . , 50 percent, . . . , 55 percent, . . . , 60 percent, . . . , 65 percent, . . . , 70 percent, . . . , 75 percent, . . . , 80 percent, . . . , 85 percent, . . . , 90 percent, 91 percent, 92 percent, 93 percent, 94 percent, 95 percent, 96 percent, 97 percent, and 98 percent. It may also be desirable for the ratio of the open area to the overall area of the pressure-wave reflective element 880 to be within a particular range such as between 5 percent to 95 percent, 10 percent to 90 percent, 15 percent to 85 percent, 20 percent to 80 percent, 25 percent to 75 percent, 30 percent to 70 percent, 35 percent to 65 percent, 40 percent to 60 percent, and 45 percent to 55 percent. Additionally, for any of the above listed ratios it may be desirable for each opening 885 to have a particular size, such as between 10 microns to 10,000 microns (1 millimeter), including any increment therebetween such as 10 microns, . . . , 12.5 microns, . . . , 15 microns, 17.5 microns, . . . 20 microns, . . . 30 microns, . . . 40 microns, . . . 50 microns, . . . 75 microns, . . . 100 microns, . . . 125 microns, . . . , 150 microns, . . . 175 microns, . . . , 200 microns, . . . 300 microns, . . . 400 microns, . . . , 500 microns, . . . , 600 microns, . . . , 700 microns, . . . , 800 microns, . . . , 900 microns, . . . , 1000 microns, . . . , 2000 microns, . . . , 3000 microns, . . . , 4000 microns, . . . , 5000 microns, . . . , 6000 microns, . . . , 7000 microns, . . . , 8000 microns, . . . , 9000 microns, . . . , 9100 microns, . . . , 9200 microns, . . . , 9300 microns, . . . , 9400 microns, . . . , 9500 microns, . . . , 9600 microns, . . . , 9700 microns, . . . , 9800 microns, . . . , 9900 microns, . . . and 10,000 microns. It may also be desirable for the size openings 850 within the pressure-wave reflective element 880 to be within a particular range such as between 1000 to 9000 microns, 2000 to 8000 microns, 3000 to 7000 microns, 4000 to 6000 microns, and 4500 to 5500 microns.

The pressure-wave reflective element's ability to reduce or prevent the formation of vapor bubbles exterior of the pressure-wave reflective element 880 and/or the balloon 850 potentially reduces the existence and/or the size of the vapor bubbles formed on the exterior of the balloon catheter, which in turn reduces the likelihood that vapor bubbles will be created and expand and contract between the balloon catheter and the vasculature wall. And reducing or preventing expansion and contraction of vapor bubbles between the balloon catheter and the vasculature wall prevent or reduce the likelihood that a hydraulic force or pressure will be applied to the vascular occlusion and/or to the walls of the vessel, thereby preventing and/or minimizing potential damage to the vasculature itself.

Regarding the pressure-wave reflective element's ability to reinforce the balloon, the pressure-wave reflective element may reduce or prevent the balloon's ability, particularly the balloon's working length's ability, to expand and contract upon creation of the vapor bubbles therein. Reducing the balloon's ability, particularly the balloon's working length's ability, to expand and contract upon the formation of vapor bubbles within the balloon, reduce or prevent the balloon 850 from applying a hydraulic force or pressure to the vascular occlusion and/or to the walls of the vessel.

Figure 15A:
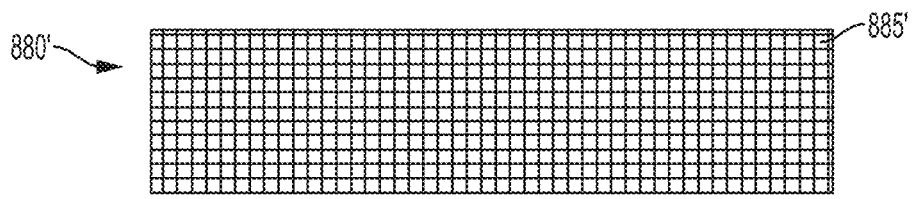
FIG. 15A is a side elevation view of a pressure-wave reflective element comprising a plurality of square-shaped openings, according to one embodiment of the present disclosure.
Figure 15B:
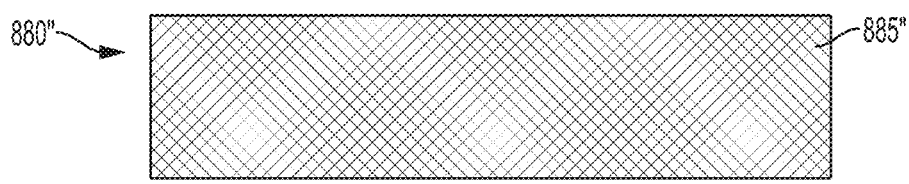
FIG. 15B is a side elevation view of a pressure-wave reflective element comprising a plurality of diamond-shaped openings, according to one embodiment of the present disclosure.
Figure 15C:
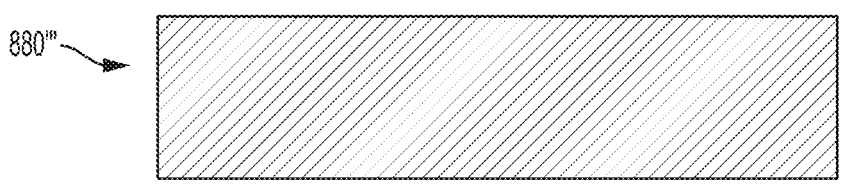
FIG. 15C is a side elevation view of a pressure-wave reflective element comprising a plurality of openings formed by a helical structure wound in a particular direction, according to one embodiment of the present disclosure.
Figure 15D:
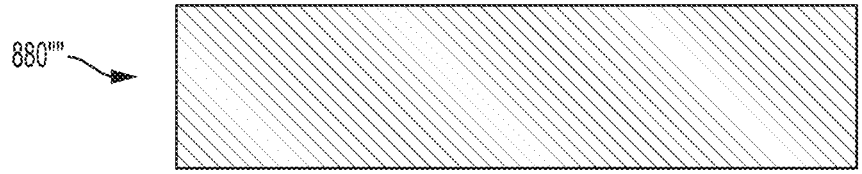
FIG. 15D is a side elevation view of a pressure-wave reflective element comprising a plurality of openings formed by a helical structure wound in a particular direction, according to one embodiment of the present disclosure.
Figure 15E:
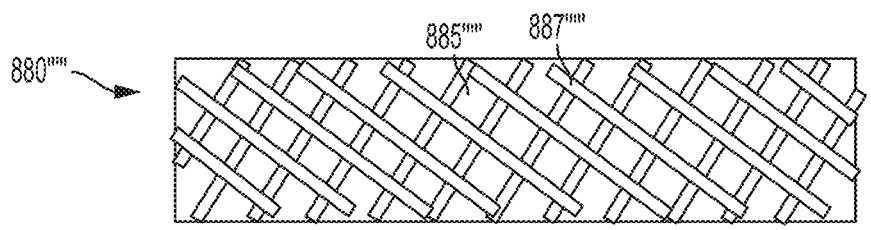
FIG. 15E is a side elevation view of a pressure-wave reflective element comprising a plurality of openings formed by a helical wound ribbons, according to one embodiment of the present disclosure.
Figure 15F:
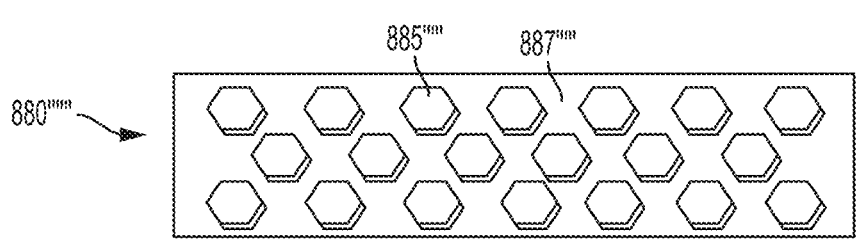
FIG. 15F is a side elevation view of a pressure-wave reflective element comprising a plurality of hexagon-shaped openings, according to one embodiment of the present disclosure.

The openings 850' in the pressure-wave reflective element 880' depicted in FIG. 15A are shown as squares, the openings 850" (and 850"") in the pressure-wave reflective element 880" (and pressure-wave reflective element 880"") depicted in FIG. 15B (and FIG. 15E) are shown as diamonds, the openings 850""' in the pressure-wave reflective element 880""' are shown as hexagons, which are disposed around the circumference of pressure-wave reflective element, as well as along its length. Although the openings in the pressure-wave reflective element in these figures are illustrated as squares, diamonds and hexagons, the openings may have an alternate shape, such as a circle, oval, triangle, rectangle, polygon, pentagon, heptagon, octagon, nonagon, and decagon. For example, FIG. 15C is a side view of a pressure-wave reflective element 880" comprising a plurality of openings formed by a helical structure wound in a particular direction (for example, clockwise or left to right), and FIG. 15D is a side view of a pressure-wave reflective element 850'" comprising a plurality of openings formed by a helical structure wound in an alternate direction (for example, counter-clockwise or right to left). Additionally, the two helically formed pressure-wave reflective elements may be combined to form the pressure-wave reflective element 880"" depicted in FIG. 15E. The pressure-wave reflective element 880"" depicted in FIG. 15E is similar to the pressure-wave reflective element 880" depicted in FIG. 15B, but the pressure-wave reflective element 880" depicted in FIG. 15B is braided and the pressure-wave reflective element 880"" depicted in FIG. 15E is wound or formed by one or two hypotubes. Additionally, the structural mass 887 (or portions thereof) of the pressure-wave reflective element 880"" depicted in FIG. 15E is larger than the structural mass (or portions thereof 1128") of the pressure-wave reflective element 880" depicted in FIG. 15B because braided materials are generally smaller in size. Referring to FIG. 15F, the structural mass 887""' (or portions thereof) of the pressure-wave reflective element 880""', are substantial in comparison to the size of the hexagonal openings 885""'. It may be desirable for the ratio of the area of the openings 885 to the area of the structural mass 887 of the pressure-wave reflective element 880 to be between 1:0.01 and 1:100, including any increment therebetween such as 1:0.01, 1:0.02, 1:0.03, 1:0.04, 1:0.05, 1:0.06, 1:0.06, 1:0.07, 1:0.08, 1:0.09, 1:0.10, . . . , 1:0.20, . . . , 1:0.30, . . . , 1:0.40, . . . , 1:0.50, . . . , 1:0.60, . . . , 1:0.70, . . . , 1:0.80, . . . , 1:0.90, 1:0.91, 1:0.92, 1:0.93, 1:0.94, 1:0.95, 1:0.96, 1:0.97, 1:0.98, 1:0.99, 1:1, 1:2, 1:3, 1:4, 1:5, 1:6, 1:7, 1:8, 1:9, 1:10, . . . , 1:15, . . . 1:20, . . . , 1:25, . . . , 1:30, . . . , 1:35, . . . , 1:40, . . . , 1:45, . . . , 1:50, . . . , 1:55, . . . , 1:60, . . . , 1:65, . . . , 1:70, . . . , 1:75, . . . , 1:80, . . . , 1:85, . . . , 1:90, 1:91, 1:92, 1:93, 1:94, 1:95, 1:96, 1:97, 1:98, 1:99, and 1:100. It may also be the ratio of the area of the openings 885 to the area of the structural mass 887 of the pressure-wave reflective element 880 to be within a particular range such as between 1:0.01 and 1:100, 1:0.10 and 1:90, 1:0.20 and 1:80, 1:0.30 and 1:70, 1:0.40 and 1:60, 1:0.50 and 1:50, 1:0.60 and 1:40, 1:0.70 and 1:30; 1:0.80 and 1:20, 1:0.90 and 1:10, 1:0.90 and 1:9, 1:0.90 and 1:8, 1:0.90 and 1:7, 1:0.90 and 1:6, 1:0.90 and 1:5, 1:0.90 and 1:4, 1:0.90 and 1:3, 1:0.90 and 1:2, or any increments therebetween, such as 1:0.91 and 1:1.9, 1:0.92 and 1:1.8, 1:0.93 and 1:1.7, 1:0.94 and 1:1.6, 1:0.95 and 1:1.5, 1:0.96 and 1:1.4, 1:0.97 and 1:1.3, 1:0.98 and 1:1.2 and 1:0.99 and 1:1.01.

In some embodiments, the devices and methods of the present disclosure can also be used to deliver laser-induced pressure waves to disrupt a vascular occlusion or restriction and/or deliver a therapeutic agent using a substantially solid light absorbing material instead of liquid medium. In some circumstances, pairing a laser that emits a specific wavelength of light with a light absorbing material designed to absorb light at that wavelength can significantly increase the energy efficiency of the resultant laser-induced pressure waves produced by the reaction. The use of such pairings can ultimately reduce the energy input required to treat a vascular occlusion or restriction and/or deliver a therapeutic agent, which can increase the safety of the procedure and reduce costs. For example, the balloon assemblies described in the present disclosure can be filled with air or a substantially inert liquid medium (for example, saline) instead of contrast medium, which can significantly reduce the amount and size of vapor bubbles produced along with the laser-induced pressure waves. Because the laser-induced pressure waves can propagate outside of the balloon to disrupt a vascular occlusion and/or deliver a therapeutic agent, it can be advantageous in some circumstances to reduce (for example, by filing the balloon catheter with saline) or eliminate (for example, by filling the balloon catheter with air or inert gas) the production of vapor bubbles. In other cases, liquid medium used to inflate the balloon can be pre-treated to remove the amount of gas dissolved in it using methods known to one of ordinary skill in the art based on the present disclosure, as this can also reduce the amount of vapor bubbles generated along with the laser-induced pressure waves.

For certain applications, it may be desirable to increase the amount and/or the size of vapor bubbles produced along with a laser-induced pressure wave that is generated by emitting laser light energy into a corresponding light absorbing liquid medium. For example, when entering smaller diameter sized blood vessels, the size of the catheter may be limited. In some cases, the force that vapor bubbles exert on tissue (for example, a vascular occlusion) may be proportional to the size of the individual vapor bubbles created, as the bubbles expand and contract after laser light energy is emitted into liquid medium and a laser-induced pressure wave is generated. That is, the strength of the laser-induced pressure wave and/or the size of the vapor bubble may be limited with the use of a non-gas saturated liquid medium. One manner by which the size of individual vapor bubbles can be increased (for example, to impart greater amount of force on a particular tissue) is to saturate the liquid medium with gaseous substances so that the gas within the liquid medium exhibits a higher vapor pressure as compared to that of the liquid medium without such gas. Suitable gaseous substances that may be used to create gas-saturated liquid medium include, but are not limited to, ambient air, carbon dioxide, iodine gas, oxygen, nitrogen, compressed air, nitrous oxide, and combinations of these.

The higher vapor pressure of the gaseous substance added to the liquid medium will cause the gaseous substance to return to a gaseous state faster (under smaller pressure fluctuations) than the liquid medium. In other words, less pressure is required to cause the saturated gaseous substances to come out of solution, resulting in the creation of larger vapor bubbles, and concomitantly, a greater amount of force. In some cases, the use of gas-saturated liquid medium allows for the use of laser light energy at decreased intensities, or decreased pulses or pulse durations, without any accompanying decrease in the overall force generated by the vapor bubbles (as each vapor bubble is larger). This can enhance both the safety and efficacy of the procedure being performed.

The gaseous substances can be imparted to the liquid medium through various means, including under pressure, through mechanical agitation, and/or by bubbling the gas into the liquid medium. In some cases, gas-saturated liquid medium can be prepared prior to a procedure and then injected into a balloon prior to performing the procedure. Additionally or alternatively, gaseous substances can be delivered into that liquid medium that is already present in the catheter balloon.

The gases and/or gaseous substances may be dissolved and quantified by the amount of gases present in a 1 kg of the liquid medium. The maximum amount of gas that will dissolve in the liquid medium is dependent on the solubility of the particular gas in that liquid medium, the pressure, and the temperature as described by Henry's law of gas solubility. For example, carbon dioxide may be dissolved into water at a concentration of 1.25 g/kg of water or less at 30 degrees Celsius under atmospheric pressure. And upon dissolving carbon dioxide into water or saline, an overall concentration between 0.25-3.5 g/kgH$_2$O is produced. The concentrations of other dissolved gases in a kilogram of liquid medium ranges from 1 mg-1 g/kg for iodine, 5-80 mg/kg for oxygen, 5-40 mg/kg for nitrogen, 5-500 mg/kg for room air, and 0.1-4 g/kg for nitrous oxide.

The gases and/or gaseous substances may be dissolved in quantities above the theoretical limit, which is known as super saturation. The theoretical limit is described by Henry's law as mentioned previously. By dissolving the gases under increased pressure or decreased temperature and then returning it to normal atmospheric conditions, it is possible to dissolve a larger quantity of gas then is possible at atmospheric conditions. For example, 2.5 g of carbon dioxide may be dissolved into 30 degrees Celsius water under 2 atm of pressure, and then returned to atmospheric pressure. For any dissolved gas, the saturation percentage is defined by the concentration of gas over the theoretical maximum concentration. For any of the previously mentioned gases in a supersaturated solution, the saturation percentage can range from 100-300 percent.

The use of a gas saturated liquid medium or super saturated liquid medium may also increase the laser-induced pressure wave caused by the interaction of the laser light and the liquid medium. That is, the gas saturated liquid medium or super saturated liquid medium may contain larger potential energy, which when activated by the laser light, may create a larger laser-induced pressure wave in comparison to a laser-induced pressure wave created by the interaction of laser light and a non-gas saturated liquid medium.

Suitable light absorbing material can be any agent capable of absorbing light energy and producing a laser-induced pressure wave. For example, the light absorbing material can contain an aromatic hydrocarbon with iodine bonded to it, such as iodinated x-ray contrasts. Low osmolar, non-ionic, iodinated, and radio-opaque contrasts are also suitable light absorbing materials that can be used to produce laser-induced pressure waves. Other light absorbing materials include, but are not limited to, iodinated contrasts such as Diatrizoic acid, Metrizoic acid, Iodamide, Iotalamic acid, Ioxitalamic acid, Ioglicic acid, Acetrizoic acid, Iocarmic acid, Methiodal, Diodone, Metrizamide, Iohexol, Ioxaglic acid, Iopamidol, Iopromide, Iotrolan, Ioversol, Iopentol, Iodixanol, Iomeprol, Iobitridol, Ioxilan, Iodoxamic acid, Iotroxic acid, Ioglycamic acid, Adipiodone, Iobenzamic acid, Iopanoic acid, Iocetamic acid, Sodium iopodate, Tyropanoic acid, Calcium iopodate, Iopydol, Propyliodone, Iofendylate, Lipiodol, non-iodinated contrasts such as Barium sulfate, MRI contrast agents such as Gadobenic acid, Gadobutrol, Gadodiamide, Gadofosveset, Gadolinium, Gadopentetic acid, Gadoteric acid, Gadoteridol, Gadoversetamide, Gadoxetic acid, Ferric ammonium citrate, Mangafodipir, Ferumoxsil, and Ferristene Iron oxide nanoparticles, Perflubron, Glucose and other carbohydrates, Albumen and other proteins, Nitroglycerin or other vasodilators, Hydrocarbons such as Oils, Alcohols, or other organic functional groups (Amines, Alkanes, Carboxyl, and the like), blood/tissue products such as Platelet Rich Plasma (PRP), packed red cells, plasma, platelet, fat, Charcoal, biocompatible materials such as stainless steel, biopolymers, and bioceramics, or other pharmacological agents which contain a combination of aromatic carbon rings and functional groups such as Salicylic acid, Acetylsalicylic acid, Methyl salicylate, Mesalazine, Aspirin, Acetaminophen, Ibuprofen, Clopidogrel, or other pharmacological and/or biological agents which may be compatible with the medical procedures described herein.

Suitable light absorbing material can also include those materials capable of absorbing wavelengths in the UV spectrum. For example, light absorbing materials can include, but are not limited to, PABA, Padimate 0, Phenylbenzimidazole sulfonic acid, Cinoxate, Dioxybenzone, Oxybenzone, Homosalate, Menthyl anthranilate, Octocrylene, Octyl methoxycinnamate, Octyl salicylate, Sulisobenzone, Trolamine salicylate, Avobenzone, Ecamsule, 4-Methylbenzylidene camphor, Tinosorb M, Tinosorb S, Tinosorb A2B, Neo Heliopan AP, Mexoryl XL, Benzophenone-9, Uvinul T 150, Uvinul A Plus, Uvasorb HEB, Parsol SLX, or Amiloxate, Silicon and its various atomic structures, Cadmium telluride, Copper indium gallium selenide, Gallium arsenide, Ruthenium metalorganic dye, Polyphenylene vinylene, Copper phthaloncyanine, Carbon fullerenes and derivatives, Carbon compounds such as Graphite, Graphene, Diamond, Charcoal, Titianium and oxides, Nickel and oxides, Gold, Silver, Zinc and oxides, Tin and oxides, Aluminum and oxides, or alloys or ceramics of the preceding metals.

Light absorbing material may be combined with various other compounds to facilitate their attachment to a substrate. For example, light absorbing materials may be combined with various compounds (for example, solubilizing agents) that aid in the generation of a solution or mixture comprising the light absorbing material, which can be used to coat the substrate. In some embodiments, a biodegradable and biocompatible hydrophobic polymer may be used as a light absorbing material. For example, the biodegradable and biocompatible hydrophobic polymer may be poly(glycerol sebacate acrylate) (PGSA), or variations and combinations thereof, which can be crosslinked using ultraviolet light. Ultraviolet light may be emitted from the distal end of a catheter, which may be disposed within or outside of an inflatable balloon, to activate the PGSA, for example.

Other light absorbing material can also include agents having adhesive-like properties, and in some cases, the light absorbing properties of these agents can be in addition to, or independent of, their use as adhesives. For example, light absorbing materials can include, but are not limited to, cyanoacrylates, bovine serum albumin (BSA)—glutaraldehyde, fibrin sealants, gelatin matrix thrombin, gelatin sponge, oxidized cellulose, collagen sponge, collagen fleece, recombinant factor VIIa, and the like. In some embodiments, the light absorbing material may comprise hydrophobic functional groups, such as hexanoyl (Hx; C6), palmitoyl (Pam; C16), stearoyl (Ste; C18), and oleoyl (Ole; C18 unsaturated) groups, so as to resist being washed out or disengaged from their substrate in predominately aqueous environments (for example, vascular tissue). Such light absorbing materials can include, but are not limited to, 10Ole—disuccinimidyl tartrate, 10Ste—disuccinimidyl, and variations and combinations thereof.

Light absorbing material can be configured to exhibit high absorption of light energy from an emitter. Light energy can be emitted at any suitable wavelength capable of generating laser-induced pressure waves. Light energy can be emitted between about 1 nanometer and about 1 millimeter. In some cases, light can be emitted from about 10 nanometers to about 5000 nanometers. In some cases, light can be emitted from about 100 nanometers to about 1000 nanometers. In some cases, light can be emitted from about 250 nanometers to about 750 nanometers. In some cases, light can be emitted from about 300 nanometers to about 600 nanometers. In still other cases, light can be emitted from about 300 nanometers to about 350 nanometers.

In general, the light absorbing material can be located anywhere within the balloon catheter, so long as it generally intersects with the path of light emitted from the emitter, thereby generating a reaction between the light and the absorbing material. In some embodiments, the light absorbing material may be substantially solid (for example, stable in a generally solid state, such as metals and metal alloys). Substantially solid light absorbing material can be used to construct various portions of the components of the catheter that are located within the balloon, and/or substantially solid light absorbing material can be used to construct a separate structure that is independent of another catheter component.

In some embodiments, the light absorbing material can be applied to a separate supporting structure (such as, a support structure that is not predominately made of light absorbing material, or a support structure that is not being used as a light absorbing material) and used to generate laser-induced pressure waves using the devices and methods of the present disclosure. In some embodiments, the light absorbing materials are stable only in liquid, gel, or semi-liquid forms. In these embodiments, the light absorbing material can be included as part of a formulation or coating that is suitable for application to a support structure, such as impregnated in hydrogel or other solid support matrix. In some embodiments, the light absorbing materials can be part of a formulation or coating containing other agents that facilitate their placement on and/or adherence to a support structure. For example, solid absorbing materials can be formulated with coating agents, thickening agents, adhesive agents, and/or other pharmaceutical or biological agents that are suitable for use with the devices and methods of the present disclosure.

Figure 12:
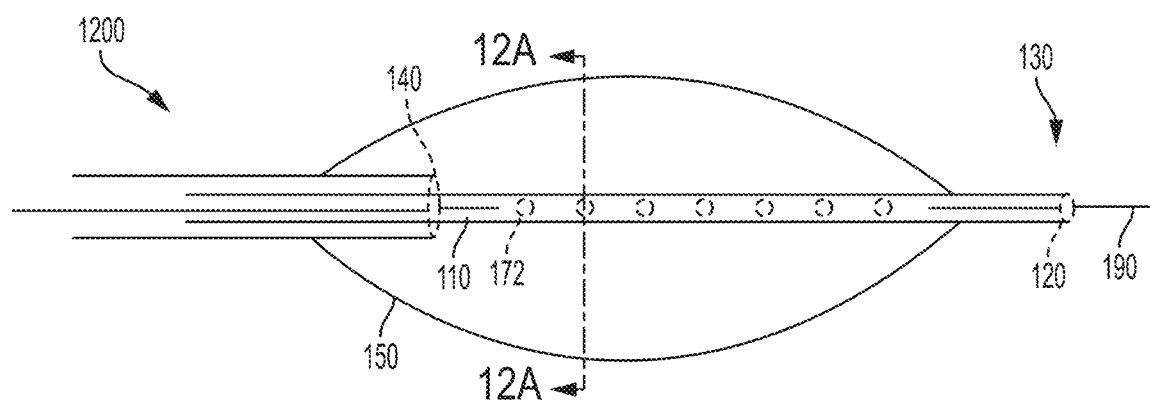
FIG. 12 is a representative longitudinal view of the distal end of the catheter including a balloon catheter, according to one embodiment of the present disclosure.
Figure 12A:
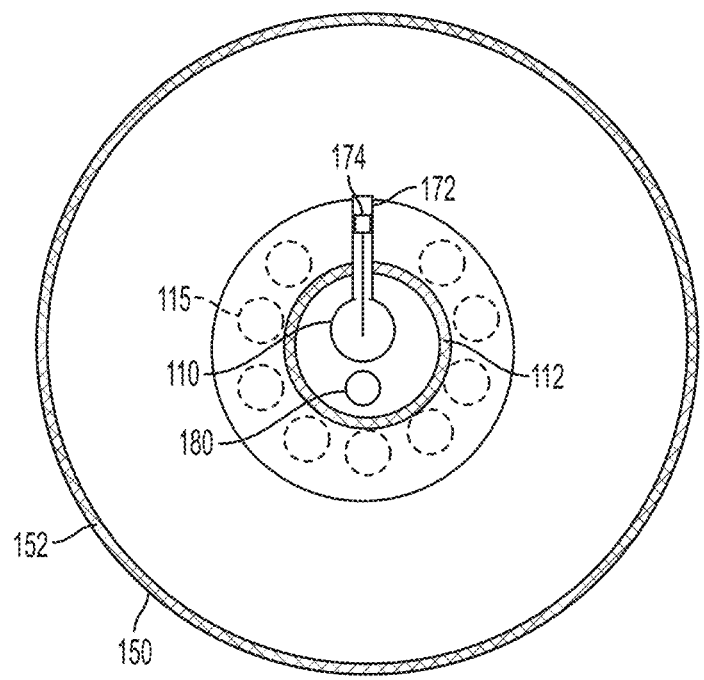
FIG. 12A is a representative cross-sectional view (through plane A in FIG. 12) of the distal end of a catheter with the balloon in a partially inflated configuration, according to one embodiment of the present disclosure.

Referring to FIGS. 12 and 12A, the distal end of catheter 1200 of the present disclosure can include one or more layers of emitters arranged circumferentially around or adjacent to an inner lumen 110, as well as a support structure for use as a substrate for the application of light absorbing material. For example, FIG. 12A is a cross-sectional view along the plane demarcated by line A-A in FIG. 12, and the light absorbing material support structure 174 is shown exiting the inner lumen 110 through port 172. The light absorbing material can be applied as a coating, as described above, on the distal end of the support structure 174 exposed to the inner cavity of the balloon 150, and the distal end support structure 174 can be positioned such that it generally intersects with the path of the light emitted from the distal end of the emitters 115, thereby generating a reaction between the light and the absorbing material. The balloon 150 can be inflated with an inert gas or liquid, as described above, through one or more inflation medium ports. Additionally, the distal end of the light absorbing material support structure 174 can be extended to intersect generally with the path of light emitted from any of the emitters that are depicted in FIGS. 3A-3C. The distal end of the light absorbing material support structure 174 can also exit any ports 172 located along the inner lumen, as shown in FIG. 12.

Figure 13:
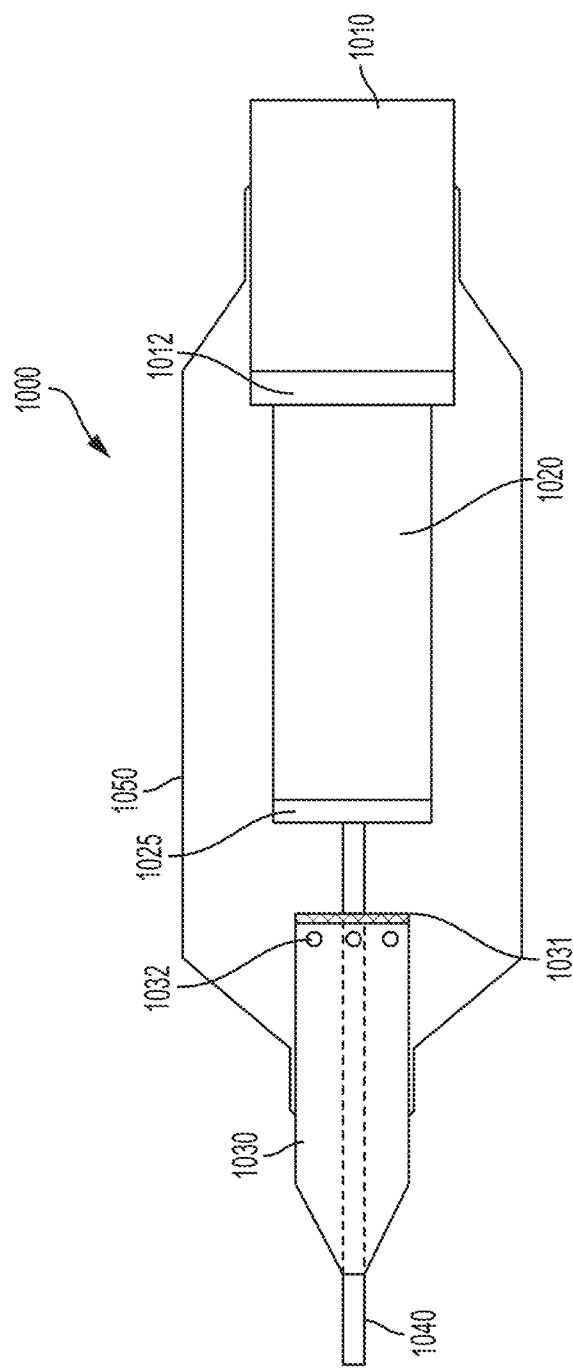
FIG. 13 is a representative cross-sectional side view of the distal end of the balloon catheter, including an energy absorbing material, and laser ablation catheter.

In some embodiments, as shown in FIG. 12A, the light absorbing material can be applied to various surfaces within the balloon 150 itself instead of being applied to a support structure. For example, the light absorbing material can be applied as a coating to the inner surface of the balloon 152 or portions thereof. The laser light emitted from the distal end of the emitters 115 can be directed upward and/or outward such that it can react with the light absorbing material 150 to generate a laser-induced pressure wave, without the need for an additional support structure. Additionally, the light absorbing material can be applied as a coating to the external surface of the inner lumen 112. In this case, the laser light emitted from the distal end of the emitters 115 can be directed downward and/or inward such that it can react with the light absorbing material 112 to generate a laser-induced pressure wave, without the need for an additional support structure. In other embodiments, the light absorbing material can also be applied as a coating to one or more proximal surfaces 1031 of the distal tip of the catheter 1030, as shown in FIG. 13. In this case, laser light emitted from the distal portion 1025 of the laser catheter 1020 within the balloon catheter 1050 can contact the light absorbing material located on a proximal surface 1031 of the distal tip 1030 to generate a laser-induced pressure wave, without the need for an additional support structure.

Figure 14:
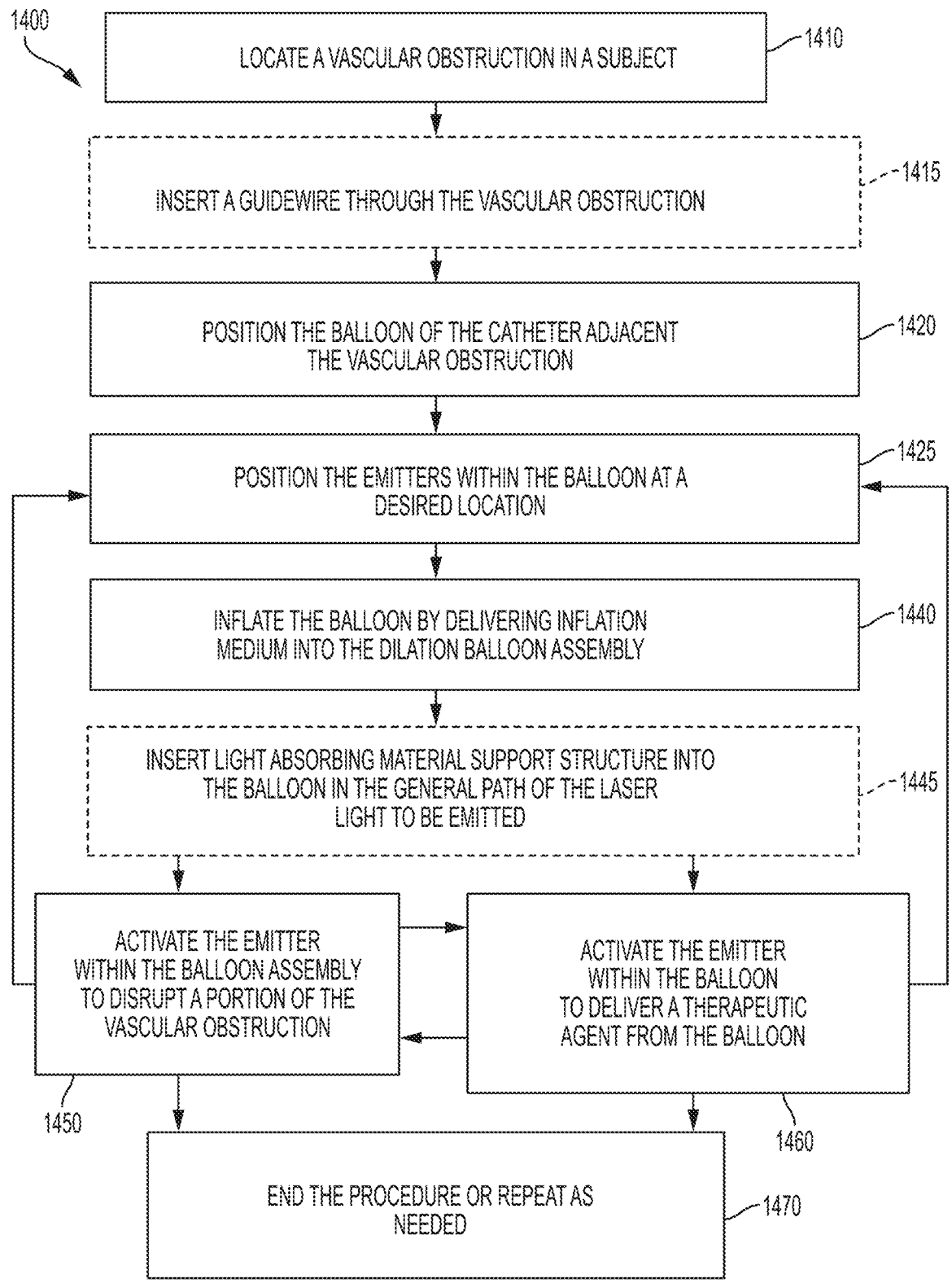
FIG. 14 is a representative flow diagram of methods of treating a subject using a catheter having energy absorbing material, according to one embodiment of the present disclosure.

Referring to the flow chart in FIG. 14, the present disclosure includes a method for treating a subject with a vascular obstruction or restriction 1400 using embodiments of the catheter described herein. Although it is not illustrated in FIG. 14, it may be desirable to use a laser catheter to ablate at least a portion of the vascular occlusion in the vessel of the subject prior to performing the method set forth in FIG. 14 and/or using the a laser catheter to ablate at least a portion of the vascular occlusion in the vessel prior to and/or subsequent to performing any of the steps set forth in FIG. 5. The method 1400 in FIG. 14 includes locating a vascular obstruction or restriction in the vessel of a subject 1410. The next step, which is optional, includes locating a guidewire at the occlusion and/or inserting a guidewire through the occlusion 1415. Thereafter, any of the embodiments of the catheters described herein may be slid over the guidewire and into the vasculature such that the balloon catheter, which is coupled to the catheter, is positioned adjacent to the vascular obstruction or restriction 1420. As discussed herein, the emitters within the balloon catheter may be fixed or slidable with respect to the balloon catheter. For example, if the emitters are included with the laser catheter, which is slidable within the catheter and balloon of the balloon catheter, the emitters may be positioned (and subsequently re-positioned) anywhere along the length of the balloon at a desired location. Additionally or alternatively, the method 1400 includes inflating the balloon by delivering inflation medium (for example, liquid medium comprising saline or gas medium comprising inert air) from the inner lumen of the catheter through one or more inflation medium ports and into the balloon 1440. In some cases, if a light absorbing material support structure is being used, the method 1400 includes optionally inserting and positioning the light absorbing material support structure into the balloon catheter such that it lies in the general path of the laser light emitted from the catheter 1445. In other cases, the light absorbing material is applied as a coating to one or more surfaces within the balloon catheter, and step 1445 is not performed. Instead, the method 1400 includes activating at least one energy source coupled to at least one emitter enclosed within the balloon catheter to send pulses of laser light energy to the area where the light absorbing material is located to produce propagating laser-induced pressure waves and disrupt a portion of the vascular occlusion 1450. In some cases, the method 1400 includes activating at least one energy source coupled to at least one emitter enclosed within the balloon catheter to send pulses of laser light energy to the area where the light absorbing material is located to produce propagating laser-induced pressure waves to deliver a therapeutic agent to the vascular obstruction or restriction and/or the vascular tissue near the obstruction or restriction 1460. Delivering light energy through a proximal emitter to disrupt a portion of a vascular obstruction or restriction and/or to deliver a therapeutic agent can be performed in any sequence, if at all, as part of the method 1400. For example, step 1450 could be performed without performing step 1460, step 1460 could be performed without performing step 1450, step 1450 could be performed serially while performing step 1460, such that step 1450 is performed firstly and step 1460 is performed secondly, step 1450 could be performed serially while performing step 1460, such that step 1460 is performed firstly and step 1450 is performed secondly, or steps 1450 and 1460 could be performed in parallel. Upon completing step 1450 and/or step 1460, the balloon catheter can optionally be repositioned within the vasculature and adjacent another portion thereof. Similarly, upon completing step 1450 and/or step 1460, the emitter(s) can optionally be repositioned within the balloon catheter, such as by sliding the emitters (or a laser catheter) within the balloon catheter (and catheter holding the balloon catheter). Either or both the balloon can be repositioned within the vasculature or the emitter(s) within the balloon catheter can be repositioned. The method 1400 also includes ending the procedure when the desired therapeutic outcome is obtained, or repeating any of 1410 through 1460 as may be necessary to treat a subject having a vascular obstruction or restriction. Furthermore, if step 1460 is not performed in the method depicted in FIG. 14, a drug eluting (coated) balloon (DEB or DCB) catheter may be used to deliver drugs to the remnants of the vascular occlusion. Disrupting the vascular occlusion with the laser-induced pressure waves prior to utilizing a DEB may increase the effectiveness of the drugs being applied to the vascular occlusion because to the laser-induced pressure waves disrupt the intraluminal as well as medial (within the tissue layer of the vascular wall) vascular obstruction or restrictions (for example, calcium deposits), thereby creating a pathway for the drug to enter the intraluminal and medial portions of the vasculature and/or vascular occlusion.

Although the method illustrated in FIG. 14 depicts step 1420, which includes positioning the balloon catheter adjacent the vascular occlusion or restriction, being performed prior to step 1425, which includes positioning the emitters within the balloon at a desired location, step 1425 may be performed after or in parallel with step 1420. Additionally, although the method illustrated in FIG. 14 depicts step 1420 and step 1425 as occurring prior to step 1440, which includes inflating the balloon catheter with liquid medium, step 1440 may be performed prior to or in parallel with one or both of step 1420 or step 1425. Additionally, although the method illustrated in FIG. 14 depicts step 1420 and step 1425 and 1440 as occurring prior to step 1445, which includes inserting light absorbing material support structure into the balloon catheter in the general path of the laser light to be emitted, step 1445 may be performed prior to or in parallel with one or both of step 1420 or step 1425. That is, steps 1420, 1425, 1440 and 1445 may be performed in any order.

Figure 16A:
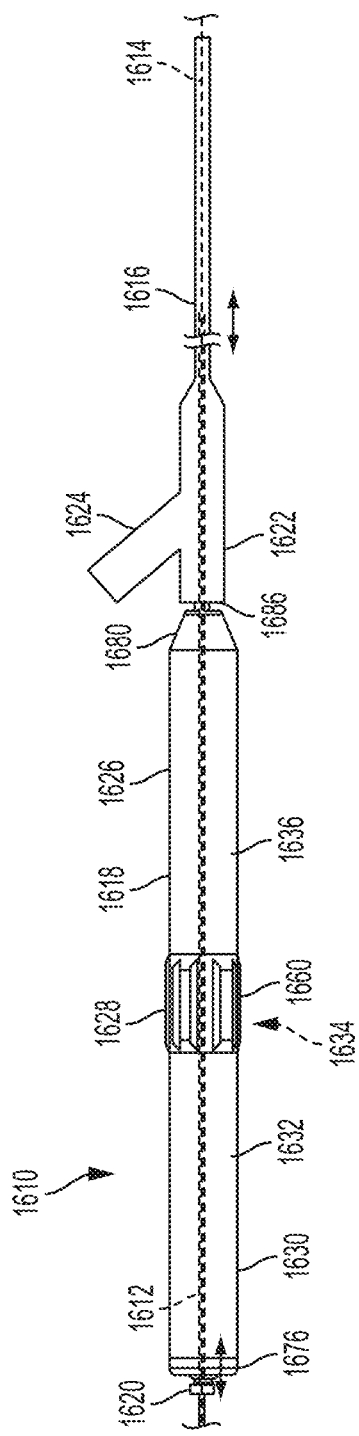
FIG. 16A is an elevation view of a kit that includes a laser catheter radially disposed within a handle and a catheter and over a guidewire, according to one embodiment of the present disclosure.
Figure 16B:
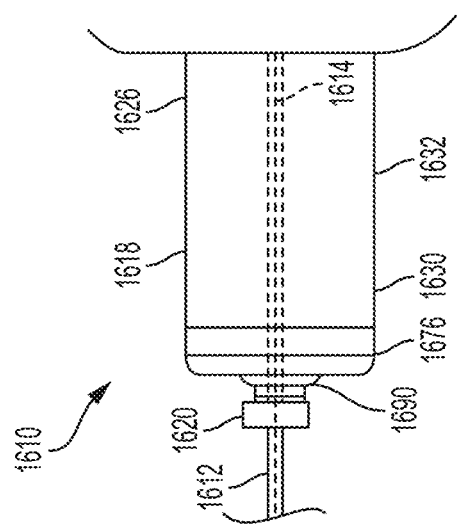
FIG. 16B is a detail elevation view of the laser catheter and the handle of FIG. 16A at a proximal end of the handle.

Referring to FIGS. 16A and 16B, a laser catheter system 1610 generally includes a laser catheter 1612, a guidewire 1614, a catheter 1616, and a handle 1618 that translatably couples the laser catheter 1612 to a catheter 1616 of a balloon catheter. The laser catheter 1612, the guidewire 1614, and the balloon catheter, including the catheter 1616 thereof, may be similar to, for example, the components of the two-piece catheter systems or kits described herein. As a specific example, the laser catheter 1612, the guidewire 1614, and the catheter 1616 may be similar to the components described above in connection with FIGS. 4A-4C, FIG. 10A and/or FIG. 13. The laser catheter 1612 is disposed within a lumen of the catheter 1616 and the handle 1618, and the laser catheter 1612 includes a proximal coupling 1620 for coupling to the handle 1618. The guidewire 1614 is disposed within a lumen of the laser catheter 1612. The catheter 1616 includes a proximal coupling 1622 for coupling to the handle 1618. The catheter 1616 also includes a balloon surrounding a portion of the catheter 1616, and the distal end of the catheter 1616 has an opening such that the laser catheter 1612 enters into the balloon. For example, referring to FIG. 13, item 1010 is a catheter, and item 1020 is a laser catheter, and the laser catheter 1020 slides through the catheter 1010 and into the opening of the balloon 1050.

A liquid medium is introduced into the catheter 1616 distal to the laser catheter 1612 within the balloon, particularly distal to the emitters of the laser catheter 1612 such that when the laser is activated, the liquid absorbs the light and creates laser-induced pressure waves and/or vapor bubbles and/or a cavitation event and resultant pressure waves within the balloon. The liquid is introduced via the lumen or a space between the laser catheter 1612 and the catheter 1616, which in turn receives the liquid from a proximal port 1624 coupled to the catheter 1616.

Figure 17E:
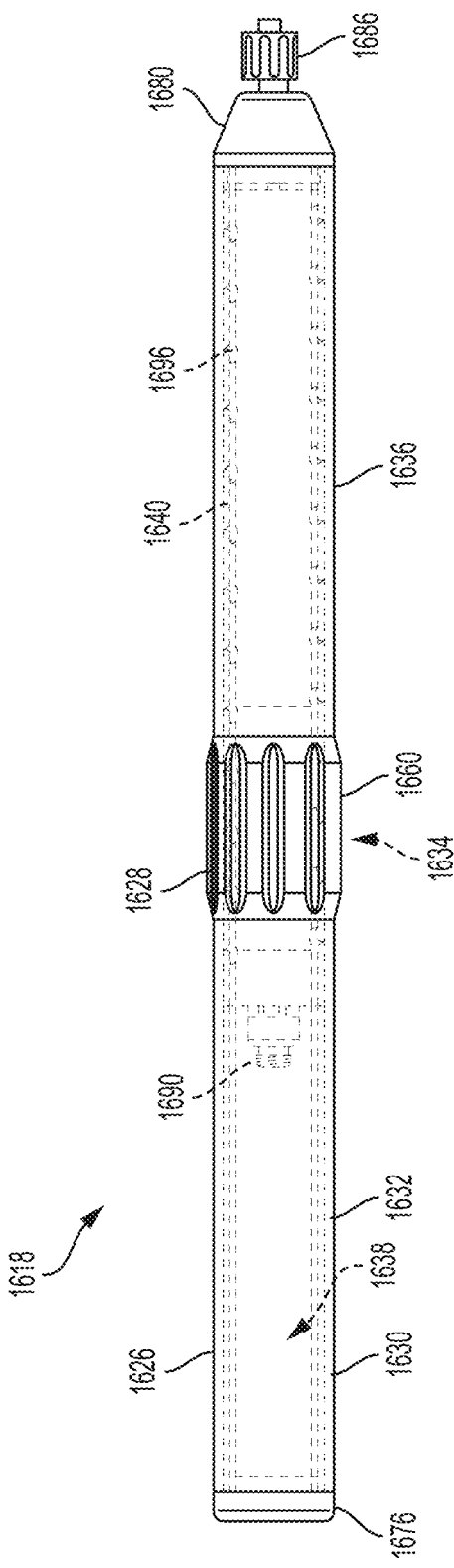
FIG. 17E is an elevation view of the handle of FIG. 16A, wherein several external components are partially transparent to illustrate internal components, and the shaft is shown in a distal position.
Figure 17F:
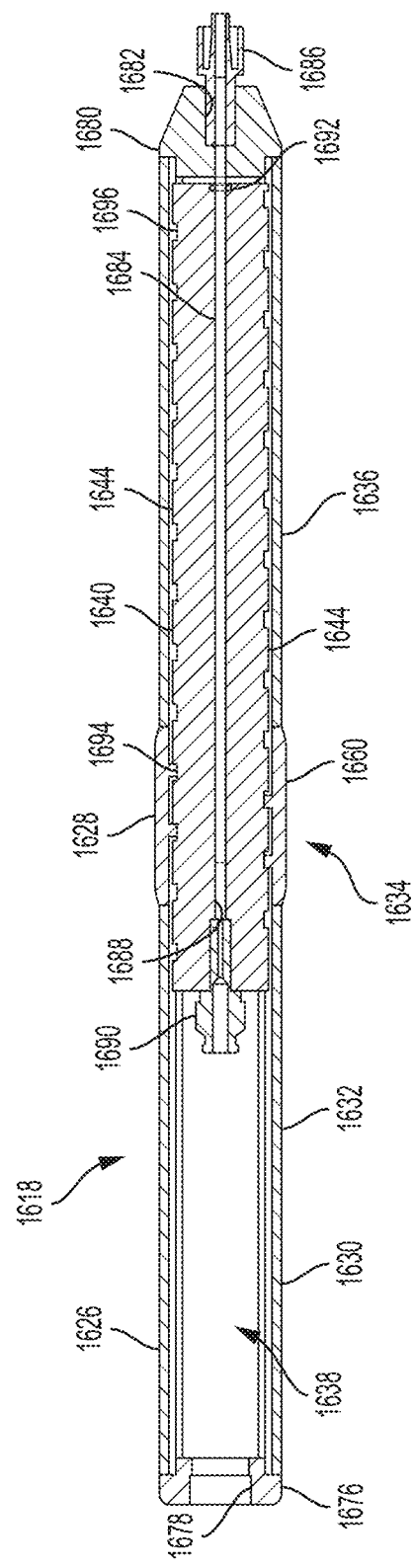
FIG. 17F is a cross-sectional view of the handle of FIG. 16A, wherein the shaft is shown in the proximal position.
Figure 17G:
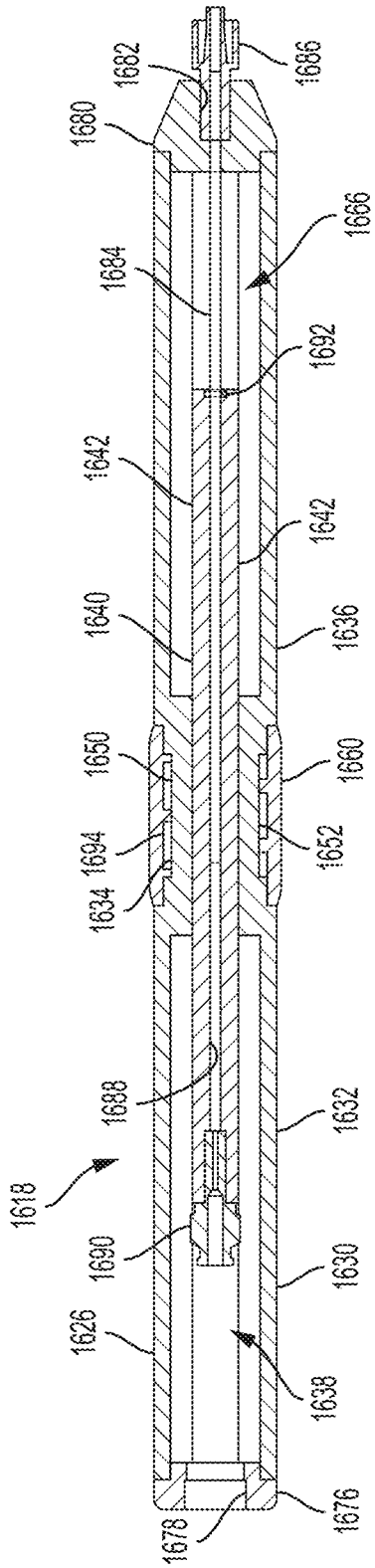
FIG. 17G is a cross-sectional view of the handle of FIG. 16A, wherein the shaft is shown in an intermediate position.

Referring now to FIGS. 16A, 16B, 17A-16G, the handle 1618 generally includes a base 1626 that couples to the catheter 1616 and a drive mechanism 1628 that couples to the laser catheter 1612. As described in further detail below, a portion of the drive mechanism 1628 is translatably coupled to the base 1626 to facilitate translating the laser catheter 1612 within the lumen of the catheter 1616 and within the balloon (for example, to the various positions shown in FIGS. 4A-4C). The drive mechanism 1628 may be translated to a proximal position relative to the base 1626 (see FIGS. 17A-17C), a distal position relative to the base 1626 (see FIGS. 17E and 17F), and an infinite number of intermediate positions therebetween (see FIGS. 17D and 17G). As a result, the laser catheter 1612 may be translated to corresponding positions relative to the catheter 1616 and relative to the balloon.

Figure 18A:
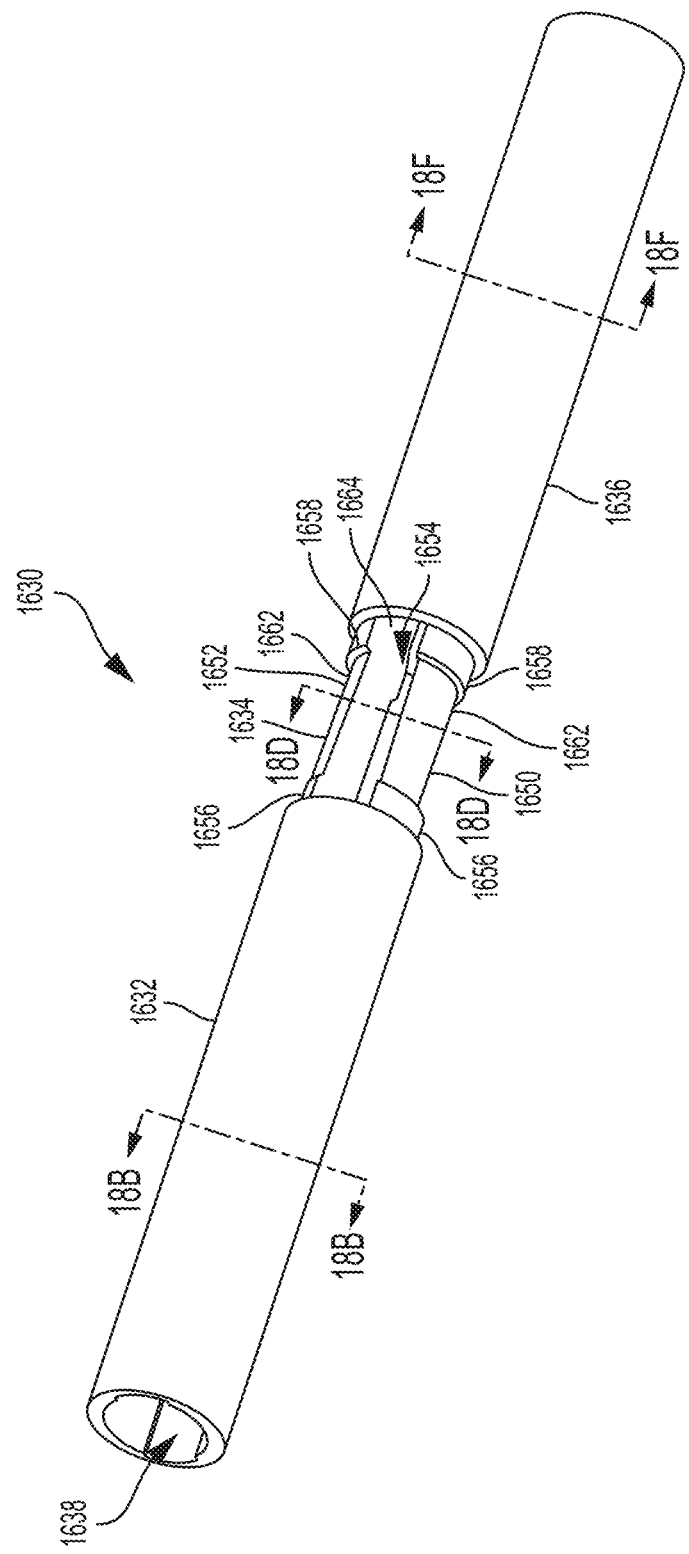
FIG. 18A is a perspective view of a frame of the handle of FIG. 16A.
Figure 18B:
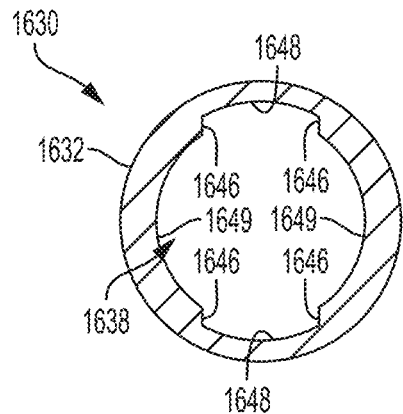
FIG. 18B is an elevation cross-sectional view of the frame along line 18B-18B of FIG. 18A.
Figure 18C:
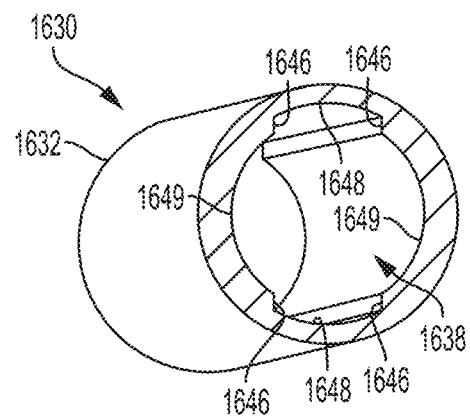
FIG. 18C is a perspective cross-sectional view of the frame along line 18B-18B of FIG. 18A.
Figure 18D:
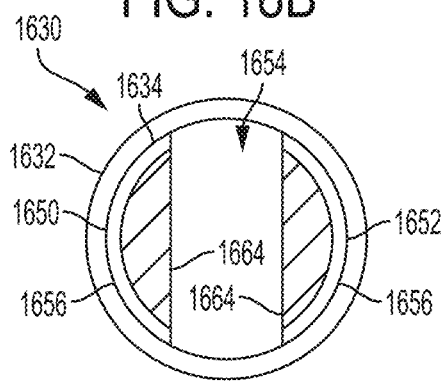
FIG. 18D is an elevation cross-sectional view of the frame along line 18D-18D of FIG. 18A.
Figure 18E:
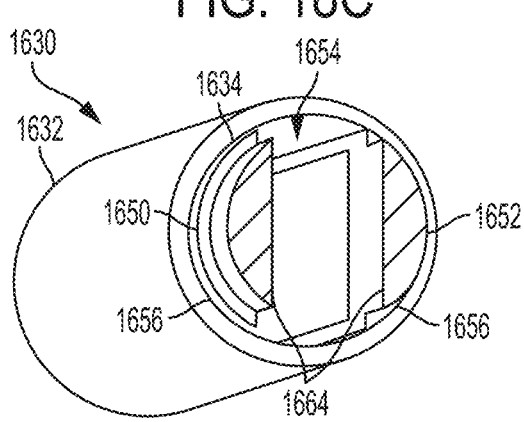
FIG. 18E is a perspective cross-sectional view of the frame along line 18D-18D of FIG. 18A.
Figure 18F:
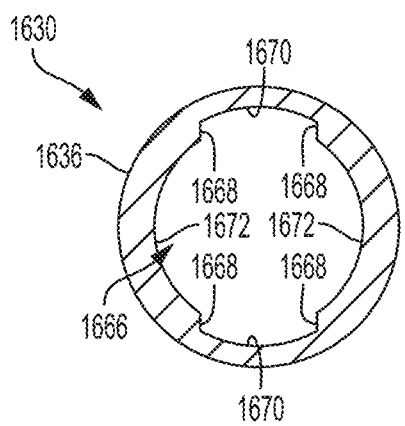
FIG. 18F is an elevation cross-sectional view of the frame along line 18F-18F of FIG. 18A.
Figure 18G:
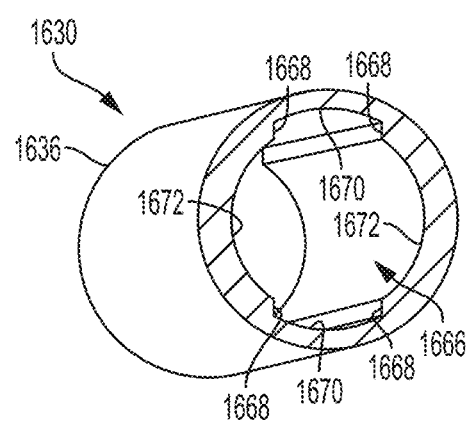
FIG. 18G is a perspective cross-sectional view of the frame along line 18F-18F of FIG. 18A.
Figure 19:
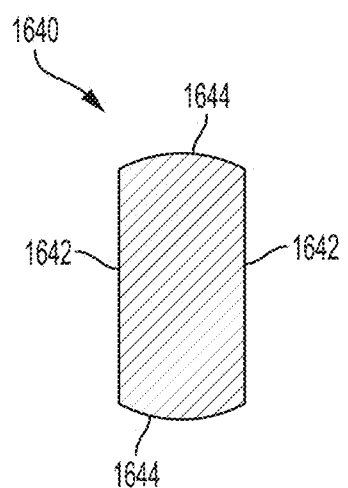
FIG. 19 is an elevation cross-sectional view of the shaft of the handle of FIG. 16A.

Referring now to FIGS. 16A-19, the base 1626 includes an elongated, hollow frame 1630 that movably couples to the drive mechanism 1628. The frame 1630 includes a proximal portion 1632, an intermediate portion 1634, and a distal portion 1636. The proximal portion 1632 defines a proximal passageway 1638 for translatably receiving a shaft 1640 of the drive mechanism 1628 therein. Referring specifically to FIGS. 18B, 18C, and 19, the proximal passageway 1638 may include a first key feature that, by coupling to a second key feature of the shaft 1640, inhibits rotation of the shaft 1640 relative to the frame 1630. For example, the second key feature of the shaft 1640 may be a non-circular cross-sectional area, and the first key feature of the proximal passageway 1638 may be a cross-sectional area that is approximately identical (that is, permitting sufficient clearance to permit relative longitudinal translation, but inhibit relative rotation and transverse translation) to the cross-sectional area of the shaft 1640, or a cross-sectional area that is approximately identical to a portion of the cross-sectional area of the shaft 1640. As a more specific example and as shown in FIGS. 18B, 18C, and 19, the shaft 1640 includes rectangle-like cross-sectional shape, with two opposing flat side surfaces 1642 and two opposing arcuate side surfaces 1644. The proximal passageway 1638 includes a cross-sectional area that is approximately identical to a portion of the cross-sectional area of the shaft 1640. Specifically, the proximal passageway 1638 is defined by four opposing flat side surfaces 1646 and two opposing arcuate side surfaces 1648. The flat side surfaces 1646 and the arcuate side surfaces 1648 engage the flat side surfaces 1642 and the arcuate side surfaces 1644 of the shaft 1640, respectively, to permit relative longitudinal translation, but inhibit relative rotation and transverse translation of the shaft 1640 relative to the frame 1460. In the present example, the proximal passageway 1438 is also defined by two additional opposing arcuate side surfaces 1649 that extend between the flat side surfaces 1646. The arcuate side surfaces 1649 are disposed apart from the shaft 1640 to reduce sliding friction between the shaft 1640 and the frame 1630.

Referring specifically to FIGS. 18A, 18D, and 18E, the intermediate portion 1634 of the frame 1630 includes a first bearing portion 1650, a second bearing portion 1652, and an opening 1654 extending therebetween and aligned with the proximal passageway 1638. Each of the first and second bearing portions 1650, 1652 includes first and second bearing surfaces 1656, 1658. The first and second bearing surfaces 1656, 1658 rotatably support a control element 1660 of the drive mechanism 1628. Each of the first and second bearing portions 1650, 1652 also includes a clearance surface 1662 between the bearing surfaces 1656, 1658. The clearance surface 1662 is also disposed radially inwardly relative to the bearing surfaces 1656, 1658. The clearance surface 1662, together with the opening 1654, facilitates driving engagement of the control element 1660 with the shaft 1640, as described in further detail below. Within the opening 1654, each of the first and second bearing portions 1650, 1652 includes a guide surface 1664. The guide surface 1664 is translatably coupled to the shaft 1640 and inhibits the shaft 1640 from rotating within the frame 1630.

Figure 17H:
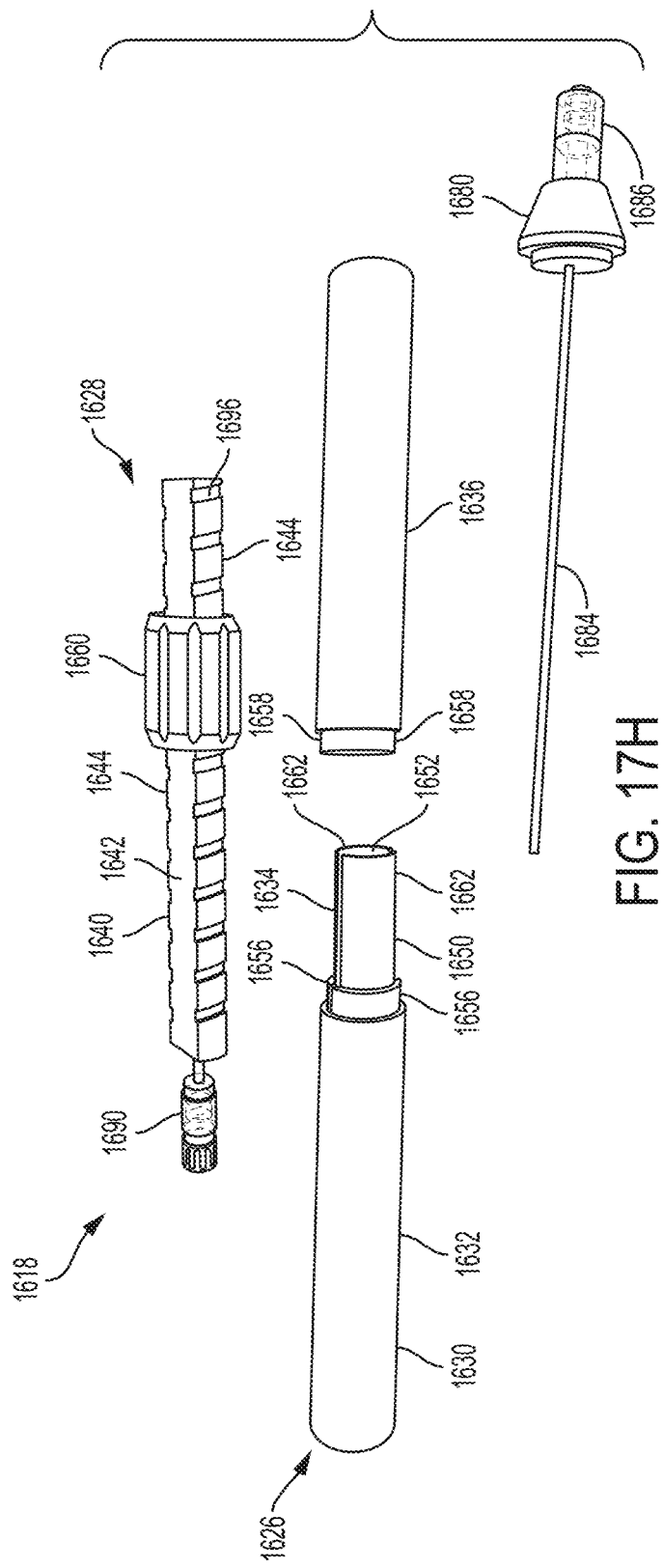
FIG. 17H is an exploded view of the handle of FIG. 16A.
Figure 17I:
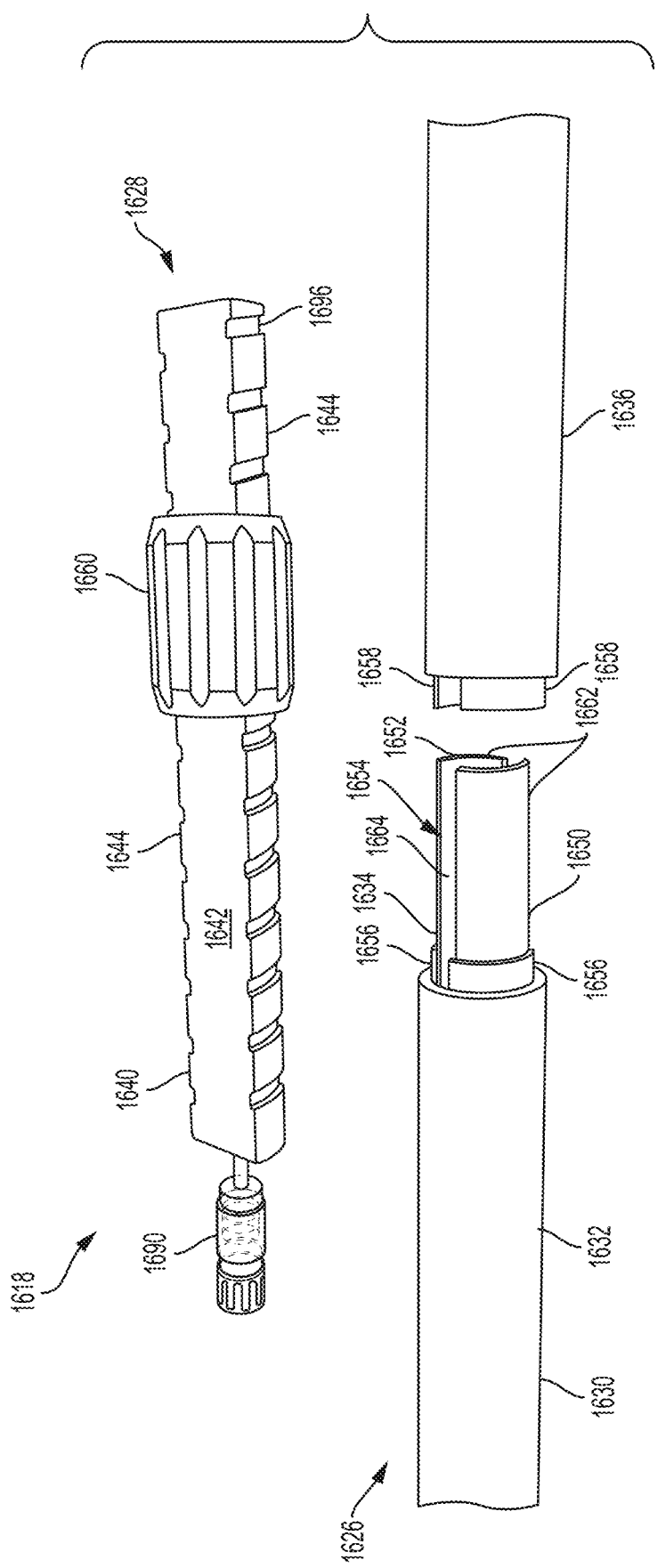
FIG. 17I is a detail exploded view of the handle of FIG. 16A.
Figure 17J:
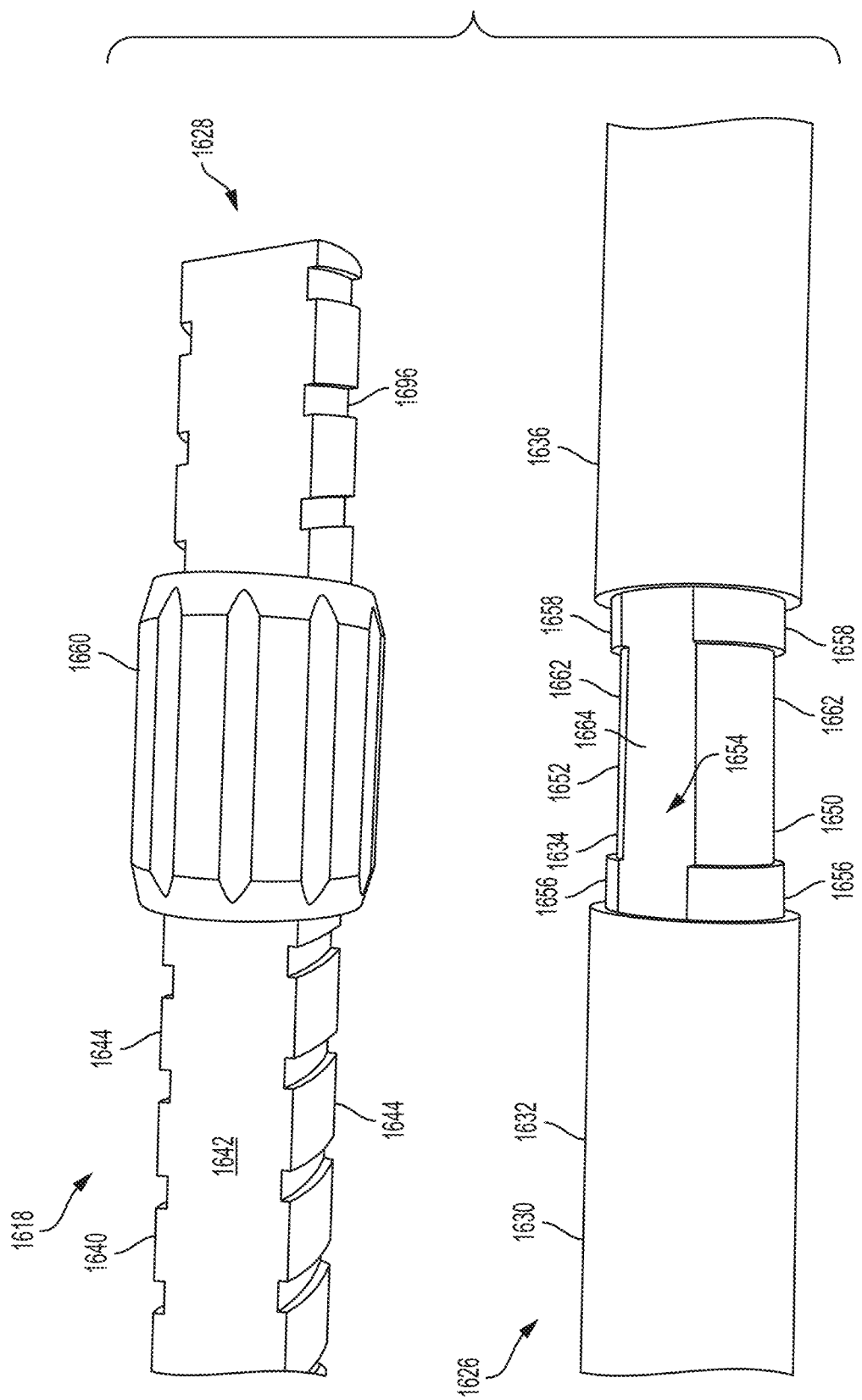
FIG. 17J is another detail exploded view of the handle of FIG. 16A.

Referring briefly to FIGS. 17H-17J, to facilitate assembly of the base 1626, each clearance surface 1662 may be monolithically coupled with the first bearing surface 1656, 1658. After positioning the shaft 1640 within the frame 1630 and the control element 1660 over the first bearing surface 1656, 1658 and the clearance surface 1662, each clearance surface 1662 may couple to the second bearing surface 1656, 1658 via, for example, press fit, one or more adhesives, snap connectors (not shown), or the like.

Referring to FIGS. 18A, 18F, and 18G, the distal portion 1636 of the frame 1630 may be similar to the proximal portion 1632 of the frame 1630. That is, the distal portion 1636 defines a distal passageway 1666 aligned with the opening 1654 for translatably receiving the shaft 1640. Referring specifically to FIGS. 18F, 18G, and 19 and in a similar manner to the proximal passageway 1638, the distal passageway 1666 may include a first key feature that, by coupling to the second key feature of the shaft 1640, inhibits rotation of the shaft 1640 relative to the frame 1630. For example, the second key feature of the shaft 1640 may be a non-circular cross-sectional area, and the first key feature of the distal passageway 1666 may be a cross-sectional area that is approximately identical to the cross-sectional area of the shaft 1640, or a cross-sectional area that is approximately identical to a portion of the cross-sectional area of the shaft 1640. In accordance with the specific example described above and as shown in FIGS. 18F, 18G, and 19, the distal passageway 1666 includes a cross-sectional area that is approximately identical to a portion of the cross-sectional area of the shaft 1640. Specifically, the distal passageway 1666 is defined by four opposing flat side surfaces 1668 and two opposing arcuate side surfaces 1670. The flat side surfaces 1668 and the arcuate side surfaces 1670 engage the flat side surfaces 1642 and the arcuate side surfaces 1644 of the shaft 1640, respectively, to permit relative longitudinal translation, but inhibit relative rotation and transverse translation of the shaft 1640 relative to the frame 1630. In the present example, the distal passageway 1666 is also defined by two additional opposing arcuate side surfaces 1672 that extend between the flat side surfaces 1668. The arcuate side surfaces 1672 are disposed apart from the shaft 1640 to reduce sliding friction between the shaft 1640 and the frame 1630.

Referring again to FIGS. 16A-18G, at its proximal end, the frame 1630 couples to a proximal cover 1676 (for example, via press fit, one or more adhesives, or the like). The proximal cover 1676 includes a proximal aperture 1678 (see FIGS. 17F and 17G) for permitting the laser catheter 1612 to extend into the frame 1630. At its distal end, the frame 1630 couples to a distal cover 1680 (for example, via press fit, one or more adhesives, or the like). The distal cover 1680 includes a distal aperture 1682 (see FIGS. 17F and 17G) for permitting the laser catheter 1612 to extend out of the frame 1630 and into the catheter 1616. The distal aperture 1682 press-fittingly receives a tube 1684 (for example, a hypotube 1684) that extends into the shaft 1640 and receives the laser catheter 1612. The distal aperture 1682 also press-fittingly receives a distal coupling 1686 that detachably and sealingly couples to the proximal coupling 1622 of the catheter 1616 of the balloon catheter.

Referring now to FIGS. 16A and 17A-17J, the drive mechanism 1628 generally includes the shaft 1640 and the control element 1660. Referring specifically to FIGS. 17F-17J, the shaft 1640 includes a shaft passageway 1688 for permitting the laser catheter 1612 to extend through the shaft 1640 and for receiving the tube 1684. The shaft 1640 passageway 1688 press-fittingly receives a proximal coupling 1690 that detachably and sealingly couples to the proximal coupling 1620 of the laser catheter 1612. As such, movement of the control element 1660 relative to the base 1626 causes the shaft 1640 to translate within the base 1626, and the laser catheter 1612 thereby translates within the lumen of the catheter 1616 and translates within the balloon.

The shaft 1640 passageway 1688 also receives a seal 1692, for example, an O-ring, which translatably engages the outer surface of the tube 1684. As such, the seal 1692 inhibits the liquid in the shaft 1640 passageway 1688 (received from the catheter 1616 via the distal coupling 1686 and the hypotube 1684) from exiting the shaft 1640 by flowing between the shaft 1640 and the tube 1684.

As described briefly above, the control element 1660 is rotatably supported by the frame 1630. The control element 1660 includes a first engagement feature that couples to a second engagement feature of the shaft 1640 such that rotation of the control element 1660 relative to the base 1626 causes translation of the shaft 1640 relative the base 1626 (and translation of the laser catheter 1612 within the lumen of the catheter 1616 and within the balloon). For example and as shown in the Figures, the first engagement feature may be a first threaded surface 1694 within the control element 1660, and the second engagement feature may be a second threaded surface 1696 formed on the arcuate side surfaces 1644 of the shaft 1640. Stated differently, the shaft 1640 may include a second, interrupted threaded surface that extends from the opening 1654 in the frame 1630 to engage the first threaded surface 1694 of the control element 1660. In any case, rotation of the control element 1660 and the first threaded surface 1694, together with the shaft 1640 being rotatably fixed within the frame 1630, causes translation of the second threaded surface 1696 and the shaft 1640 relative to the frame 1630 (and translation of the laser catheter 1612 within the lumen of the catheter 1616 and within the balloon).

Figure 20:
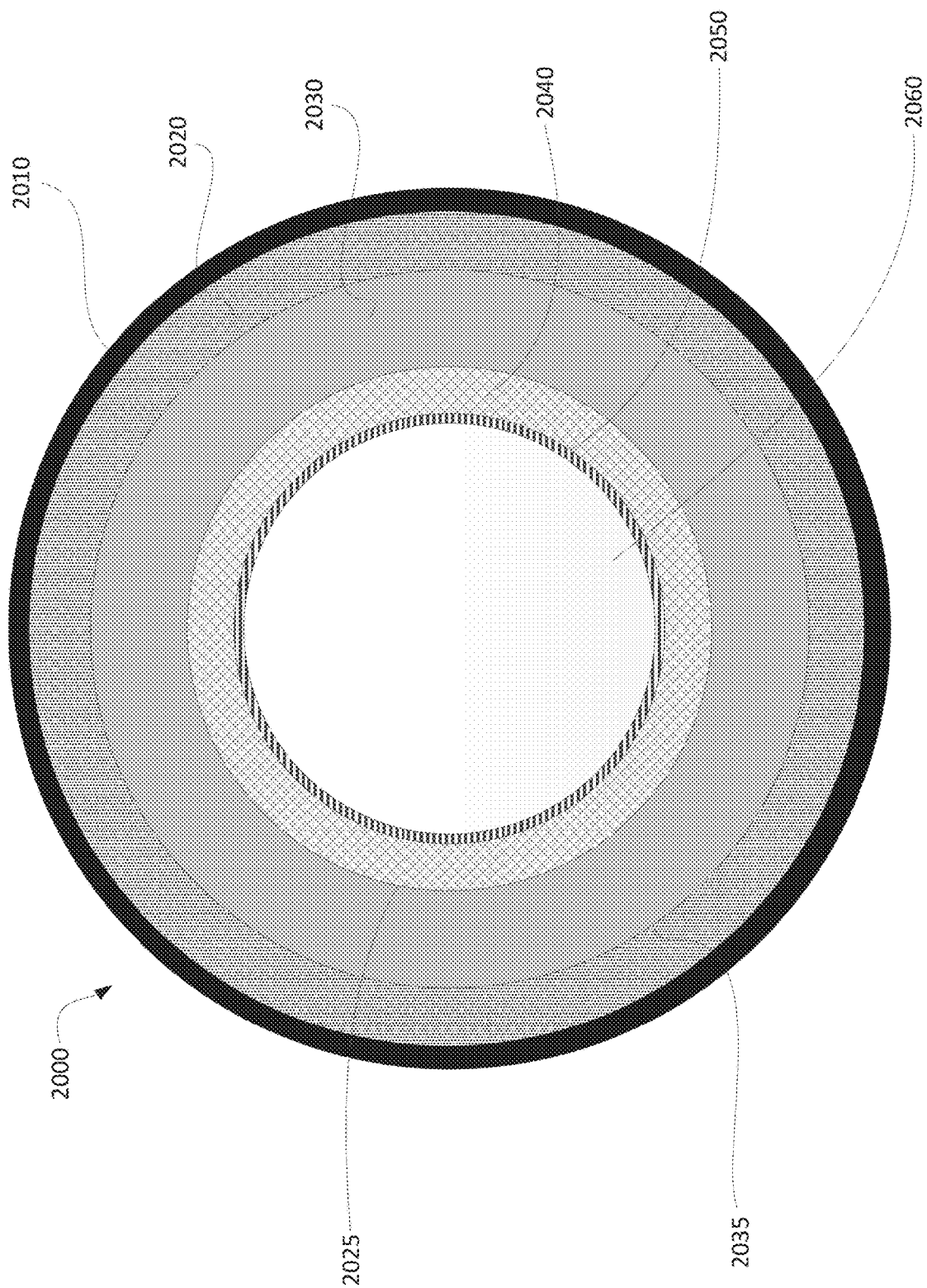
FIG. 20 is a cross-sectional view of an arterial wall taken along a direction perpendicular to the longitudinal axis of the arterial wall.

As discussed above with respect to FIG. 5, the present disclosure discusses using a laser catheter to ablate at least a portion of the vascular occlusion in the vessel of the subject prior to using the balloon catheter to disrupt the remaining portion of the vascular occlusion. FIGS. 20-21F are included to illustrate the formation of a vascular occlusion within the vasculature of a subject. Referring to FIG. 20, there is depicted a cross-sectional view of a healthy arterial wall 2000 taken along a direction perpendicular to the longitudinal axis of the arterial wall. A healthy arterial wall 2000, or vascular wall, typically includes an outer layer referred to as the "adventitia" or "adventicia" which is shown in FIG. 20 as layer 2020. There may be additional layers, such as layer 2010 of the arterial wall 2000, on the outside of the adventitia. A healthy arterial wall 2000 also includes a middle or central layer referred to as the media 2030. The media 2030 is located radially inward of and adjacent to the inner portion of the adventitia 2020. The media 2030 has a layers of smooth muscle cells and layers of elastin fiber that allows the artery to expand and contract. A healthy arterial wall 2000 also includes an inner layer referred to as the intima 2040. The intima 2040 is located radially inward of and adjacent to the media 2030. A healthy arterial wall 2000 also includes an endothelium layer 2050, which is located on the inner most surface of the intima 2040 and creates the boundary for the passageway (or inner lumen) 2060.

As mentioned above, the media 2030 is located radially inward of and adjacent to the inner portion of the adventitia 2020. Specifically, an external elastic membrane, commonly referred to as the external elastic lamina, 2035 separates the media 2030 from the adventitia 2020. As also mentioned above, the intima 2040 is located radially inward of and adjacent to the inner portion of the media 2030. An internal elastic membrane 2025, commonly referred to as the internal elastic lamina, separates the intima 2040 from the media 2030.

Referring to FIG. 20A, there is depicted a smaller version of the structure of the healthy arterial wall 2000 depicted in FIG. 20. Also, FIG. 21A is a longitudinal-sectional view of the healthy arterial wall 2000 taken along a direction parallel to the longitudinal axis of the arterial wall. Specifically, FIG. 21A is a longitudinal-sectional view of the structure of the healthy arterial wall 2000 taken along line B-B of FIG. 20A.

Referring to FIG. 21B, over time, fat and/or lipids 2070' may start to collect and/or deposit in the intima 2040' of the arterial wall 2000' as a result of buildup of fat and lipids in the blood. This disease process is commonly referred to as atherosclerosis and occurs in the arteries of the body including the coronary and peripheral arteries. It is this collection of fat and/or lipids 2070' in the intima 2040' that will lead to the formation of a vascular occlusion that can reduce or completely obstruct blood flow in the passageway 2060'. Overtime this buildup of fat and lipids 2070' becomes a heterogeneous mix 2065' (commonly referred to as plaque) of many constituents including but not limited to fats, lipids, fibrin, fibro-calcific plaque, calcium crystals, thrombus, etc. For example, a portion of the fat and/or lipids 2070' may turn into plaque 2065" and even become calcified, which is depicted as 2055" in FIG. 21C. As the fat and/or lipids 2070" collect, turn into plaque 2065" and/or become calcified 2055", the intima 2040" starts to inflame and expand, thereby decreasing the cross-sectional area of the passageway 2060".

Referring to FIG. 21D, as atherosclerotic disease progresses, and the condition of the arterial wall 2000''' is left untreated, the plaque 2065''' continue to collect, and the intima 2040''' continues to expand and decrease the cross-sectional area of the passageway 2060'''. However, upon the intima 2040'ᵛ of the arterial wall 2000'ᵛ reaching its limit to expand further, the intima 2040'ᵛ and the endothelium can rupture 2058'ᵛ and release the plaque contents previously contained in the thickened lipids and enlarged intima white blood cells into the passageway 2060'ᵛ, as depicted in FIG. 21E. Platelets and fibrin collect within the passageway 2060ᵛ of the arterial wall 2000ᵛ to try and repair the rupture, and in doing so form an occlusion 2080ᵛ, which may have calcified portions 2085ᵛ, as depicted in FIG. 21F. This figure also illustrates that formation of the occlusion 2080ᵛ further decreases the size of the passageway 2060ᵛ and in some instances fully obstructs flow.

Referring to FIG. 21D and FIG. 21G, a laser catheter 1020 may be used to debunk or remove plaque buildup contained behind the intima 2065''' or within the occlusion 2080ᵛ''' or a portion thereof from the passageway of the arterial wall 2000ˇ'. After debunking the plaque buildup or the occlusive disease, the catheter of the present disclosure may be used to treat the remaining portion of the plaque buildup 2065''' or the occlusion 2080ˇ''', particularly by disrupting the calcified portions 2085ˇ''' as depicted in FIG. 21H by use of laser-induced pressure waves as described previously, thereby leaving the treated arterial wall 2000ˇ''' in a condition as depicted in FIG. 21I. FIG. 21I illustrates the arterial wall 2000ˇ''' with an enlarged passageway 2060ˇ''', the majority of the plaque 2065''' or occlusion 2080ˇ''' removed, and the calcification of the remaining portion of the occlusion, along with the calcification of the intima 2040ˇ''', fractured or modified making it more amenable to dilation at lower atmospheric pressures. FIGS. 20A and 21A-21I use similar numeric values, but the different figures include different indicators, such as ' and ˇ and combinations thereof, for the numeric values due to the changes occurring within the arterial wall as the occlusion is formed and treated, which is progressively illustrated from one figure to the next. For purposes of brevity, certain layers of the arterial wall 2000 are omitted from the discussion of particular figures, and numeric values of certain items of the arterial wall 2000 are omitted from the particular figures. Nevertheless, one should consider the layers of the arterial wall 2000, and the formations therein, to have the same numeric values even if omitted from FIGS. 20A and 21A-21I.

Figure 22:
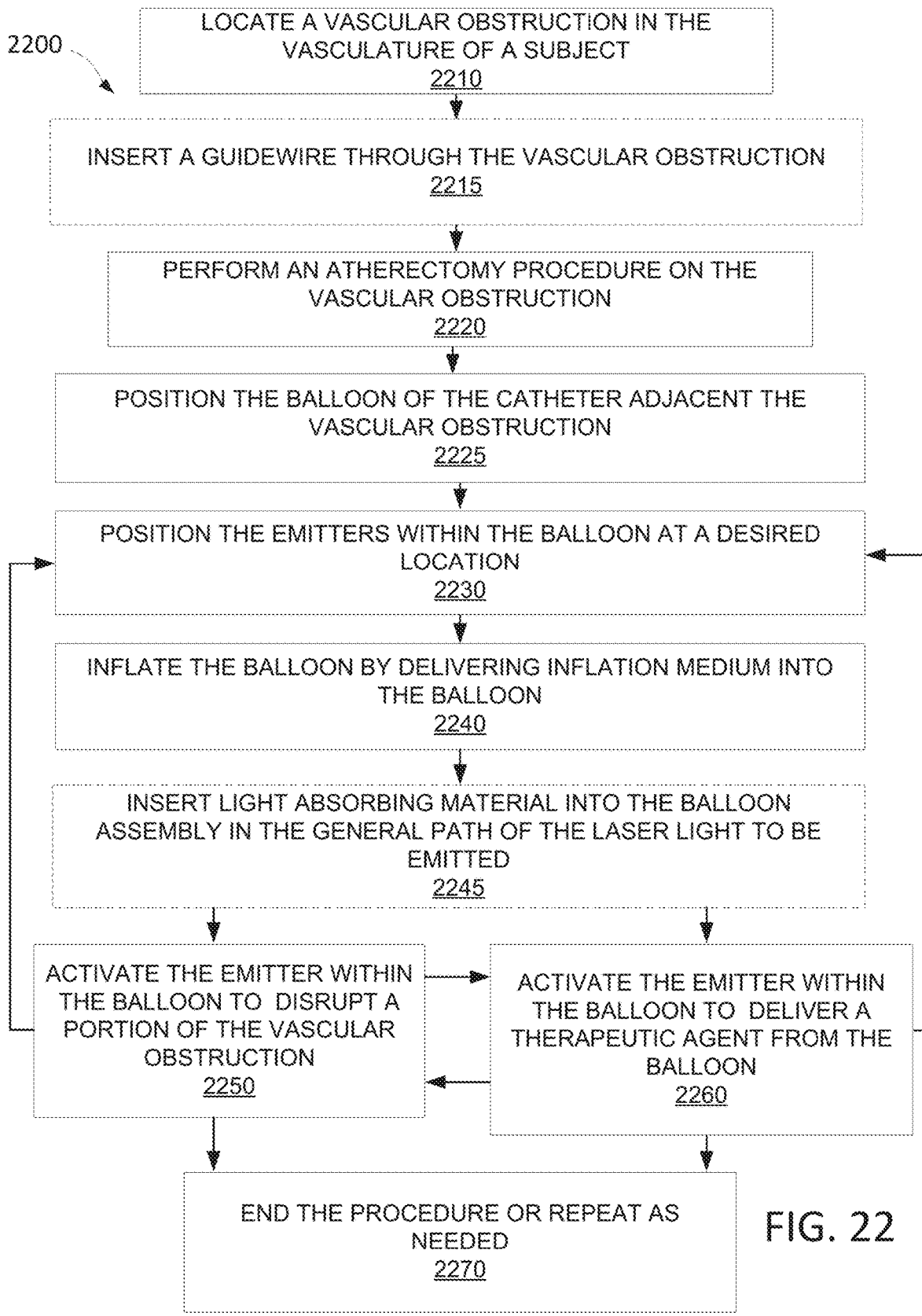
FIG. 22 is a method of removing an obstruction or restriction and treating the remainder of the obstruction or restriction within the intima with a laser-induced balloon catheter.

Referring to FIG. 22, there is a method 2200 of removing plaque buildup or occlusive disease by performing an atherectomy procedure and treating the remainder of the occlusion within the intima with the catheter of the present disclosure. This method 2200 may be used to treat coronary arteries and/or peripheral arteries including but not limited to arteries of the vasculature of the legs, the renal arteries, subclavian arteries, etc. The method 2200 in FIG. 22 includes locating a vascular obstruction or restriction in the vessel of a subject at step 2210. The next step 2215, which is optional, includes locating a guidewire at the occlusion and/or inserting a guidewire through the occlusion or through the passageway past the occlusion. Step 2220 includes performing an atherectomy procedure to remove the plaque or occlusion or a portion thereof. One type of atherectomy device is an ablation catheter, such as a laser ablation catheter, which is capable of ablating at least a portion of the vascular occlusion. Other types of ablation catheters include radiofrequency ablation catheters, microwave ablation catheters, and cryoablation catheters. Atherectomy devices other than ablation catheters, such as mechanical atherectomy devices, may also be used to remove the occlusion.

After the occlusion (or a portion thereof) is removed from the vasculature, step 2225 may then be performed. Step 2225 includes positioning a balloon catheter of the present disclosure adjacent the vascular occlusion. For example, if a clinician uses a catheter 100, 800, 1000 or any other catheter described herein, which have a guidewire lumen, the catheter(s) may be slid over the guidewire and into the vasculature such that the balloon catheter, which is coupled to the catheter(s), is positioned adjacent to the vascular obstruction or restriction (or remainder thereof). At step 2230, the emitters included with the laser catheter are positioned (and subsequently re-positioned) at any desired location along the length of the balloon. The method 2200 also includes step 2240, which comprises inflating the balloon catheter by delivering the liquid medium (for example, contrast medium) from the inner lumen of the catheter through one or more liquid medium ports and into the balloon catheter 1050. Additionally or alternatively, the method may include step 2245, which includes inserting additional light absorbing material into the balloon catheter in the general path of the laser light to be emitted. In some cases, the method 2200 includes the step 2250 of activating at least one energy source coupled to at least one emitter enclosed within the balloon catheter to emit and send pulses of laser light energy into and/or to react with the liquid medium to produce propagating laser-induced pressure waves and disrupt a remaining portion of the vascular occlusion. Disrupting the remaining portion of the vascular occlusion, particularly any calcified portions within the vascular occlusion, produces cracks in the calcified portions and/or reduces the size of the calcified portions because the pressure waves disrupt the calcified portions, thereby cracking the calcified portions and/or fragmenting the size of the calcified particles such that the contiguous area is reduced. In some cases, the method 2200 includes the step 2260 of activating at least one energy source coupled to at least one emitter enclosed within the balloon catheter to emit and send pulses of laser light energy into and/or to react with the liquid medium to produce propagating laser-induced pressure waves to deliver a therapeutic agent to a remaining portion of the vascular occlusion and/or the vascular tissue near the occlusion.

One of the benefits of the present disclosure is that the catheter and balloon catheter depicted in FIG. 21H may optionally include a reflective element, such as the pressure-wave reflective element 880 depicted over the balloon 850 of FIG. 8 above. The pressure-wave reflective element 880, or the alternatives illustrated in FIGS. 15A-15F, may reduce or prevent the formation of vapor bubbles on the exterior of the pressure-wave reflective element and/or the balloon and/or reinforces the balloon such as to minimize or prevent balloon expansion. Reinforcing the balloon and/or reducing or preventing the formation of vapor bubbles on the exterior of the pressure-wave reflective element reduces or prevents the balloon catheter from dilating the arterial wall while simultaneously allowing the pressure wave to penetrate the arterial wall and disrupt calcified portions in the occlusion and/or intima. That is, incorporating a pressure-wave reflective element, reinforcing the balloon and/or reducing or preventing the formation of vapor bubbles on the exterior of the pressure-wave reflective element potentially inhibits displacement of the soft tissue within the arterial wall and potential delamination of the layers of the arterial wall.

Although the method illustrated in FIG. 22 depicts steps 2210 through 2270 of method 2200 as being performed serially, any or all of the steps within the method 2200 may in any order and/or in parallel with any of the other steps. For example, activating an emitter to disrupt a portion of a vascular occlusion and/or to deliver a therapeutic agent can be performed in any sequence, if at all, as part of the method 2200. For example, step 2250 could be performed without performing step 2260, step 2260 could be performed without performing step 2250, step 2250 could be performed serially while performing step 2260, such that step 2250 is performed firstly and step 2260 is performed secondly, step 2260 could be performed serially while performing step 2250, such that step 2260 is performed firstly and step 2250 is performed secondly, or steps 2250 and 2260 could be performed in parallel. Upon completing step 2250 and/or step 2260, the balloon catheter can optionally be repositioned within the vasculature and adjacent another portion thereof. Similarly, upon completing step 2250 and/or step 2260, the emitter(s) can optionally be repositioned within the balloon. The balloon can be repositioned within the vasculature and/or the emitter(s) can be repositioned within the balloon. The method 2200 also includes ending the procedure when the desired therapeutic outcome is obtained, or repeating any of steps 2210 through 2260 as may be necessary to treat a subject having a vascular obstruction or restriction. Furthermore, if step 2260 is not performed in the method 2200, a drug eluting (coated) balloon (DEB or DCB) catheter may be used to deliver drugs to the remnants of the vascular occlusion. Disrupting the remaining portion of the vascular occlusion with the laser-induced pressure waves prior to utilizing a DEB may increase the effectiveness of the drugs being applied to the vascular occlusion because the laser-induced pressure waves disrupt calcium formed in the intima layer, as well as media layer of the vascular wall(s), thereby creating a pathway for the drug to enter the intima and media layers of the vasculature and/or vascular occlusion.

The present disclosure also contemplates using the laser-induced balloon assembly with conventional angioplasty balloons, as well as with DEBs. For example, a surgical procedure may include performing an atherectomy with a laser catheter, using the laser-induced balloon assembly to treat the calcified portions of the vasculature as set forth in FIG. 22 above, and then inserting an angioplasty balloon into the vasculature adjacent the relevant portion of the vasculature and expanding the angioplasty balloon to dilate the relevant portion of the vasculature.

As discussed above, the laser-induced pressure waves created by the catheter of the present disclosure not only disrupt occlusion and/or calcium in the intima layer, the laser-induced pressure waves created by the catheter of the present disclosure can also disrupt calcification of the media layer within the vascular wall(s). That is, the laser-induced pressure waves may be used to fracture or modify calcified media regardless of whether the vasculature includes an occlusion. For example, patients with medial artery calcification, which is also known as Mönckeberg's sclerosis, could potentially benefit from being treated with the catheter of the present disclosure.

Figure 23:
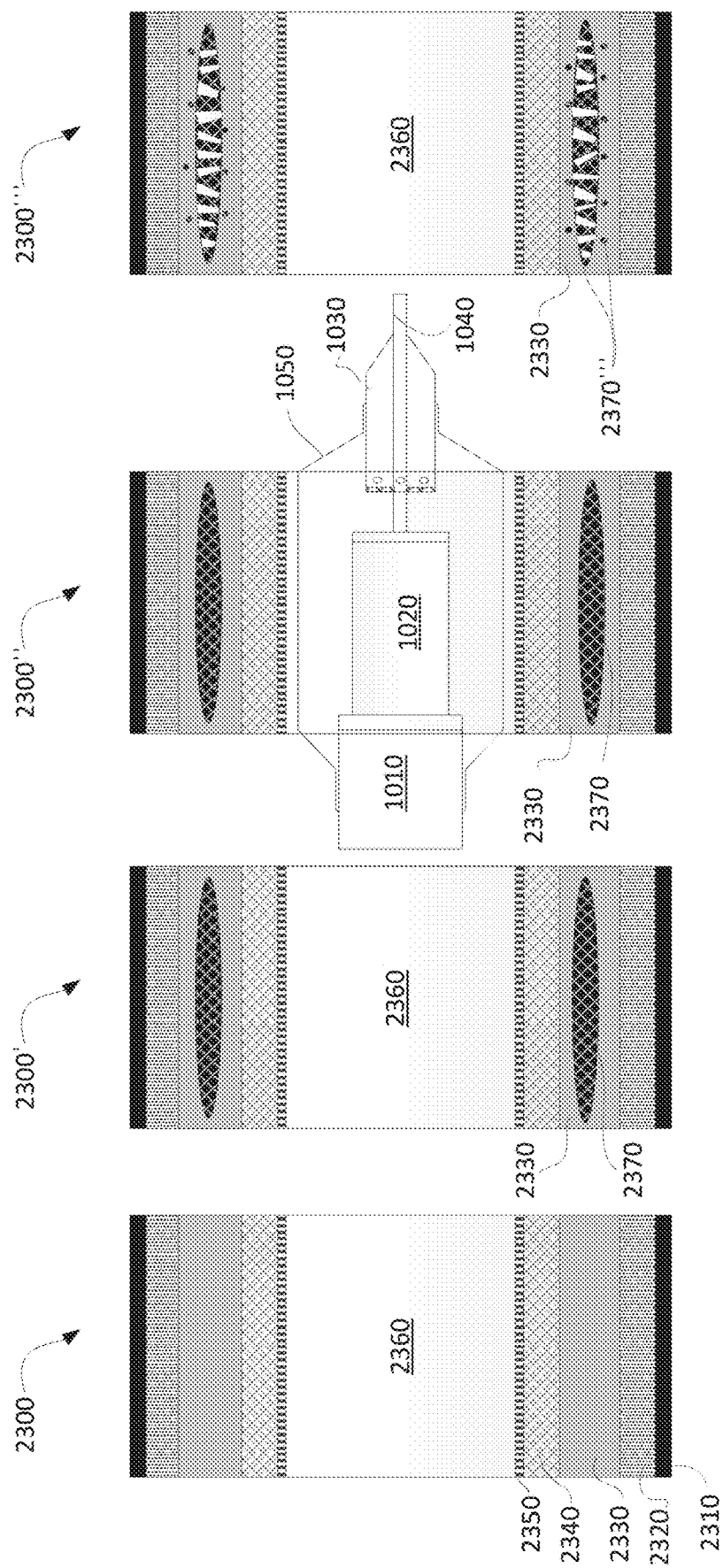
FIG. 23A is a longitudinal-sectional view of a healthy arterial wall taken along a direction parallel to the longitudinal axis of the arterial wall similar to the arterial wall depicted in FIG. 21A.
FIG. 23B is a longitudinal-sectional view of an arterial wall taken along a direction parallel to the longitudinal axis of the arterial wall with calcification of the media.
FIG. 23C is a longitudinal-sectional view of an arterial wall taken along a direction parallel to the longitudinal axis of the arterial wall with a laser-induced balloon catheter located adjacent the portion of the arterial wall that includes the calcified media.
FIG. 23D is another longitudinal-sectional view of an arterial wall taken along a direction parallel to the longitudinal axis of the arterial wall.

Referring to FIG. 23A, there is depicted a healthy arterial wall 2300 similar to the arterial wall depicted in FIG. 21A. For example, reference numerals 2010, 2020, 2030, 2040, 2050 and 2060 of FIG. 21A correspond to reference numerals 2310, 2320, 2330, 2340, 2350 and 2360 of FIG. 23A. That is, reference numerals 2310 and 2320 are the externa, reference numeral 2330 is the media, reference numeral 2340 is the intima, reference numeral 2350 is the endothelium, and reference numeral 2360 is the passageway.

Referring to FIG. 23B, there is depicted is a cross-sectional view of an arterial wall 2300' that includes calcium deposits 2370 formed in the media 2330. The calcium deposits begin as crystal aggregates and typically aggregate along the elastin fibrin layers within the media. As Mönckeberg's sclerosis (commonly referred to as medial calcification) progresses, multiple layers of calcium can form that involve up to the full circumference of the vessel. The calcium can also extend radially into the adventitia and intima layers. Mönckeberg's sclerosis (medial calcification) is caused by a recruitment of calcium by the smooth muscle cells and is attributed but not limited to common comorbidities found in patients suffering from vascular disease including diabetics, kidney disease patients and other metabolic or hormonal imbalances. The media 2330 includes smooth muscle cells and elastin fiber, which allow the artery to expand and contract. Upon formation of calcium deposits 2370, however, the artery's ability to expand and contract is reduced. That is, formation of calcium deposits 2370 in the media 2330 reduces the compliance of the artery 2300', which in turn potentially reduces the amount of blood flow through such arteries and can potentially negatively affect other health conditions, such as diabetes. This condition can occur with atherosclerotic disease as described previously or be an isolated condition without the narrowing of the lumen of the artery.

The catheter of the present disclosure is able to create laser-induced pressure waves, which fracture or disrupt the calcium deposits 2370 in the media 2330 of the arterial wall 2300" as shown in FIG. 23C, thereby increasing the compliance of the arterial wall 2300''' and blood flow therethrough. Furthermore, one of the benefits of the present disclosure is that the catheter and balloon catheter depicted in FIG. 23C, may optionally include a reflective element, such as the pressure-wave reflective element 880 depicted over the balloon 850 if FIG. 8 above. The pressure-wave reflective element 880, or the alternatives illustrated in FIGS. 15A-15F, may reduce or prevent the formation of vapor bubbles on the exterior of the pressure-wave reflective element and/or the balloon and/or reinforces the balloon such as to minimize or prevent balloon expansion. Reinforcing the balloon and/or reducing or preventing the formation of vapor bubbles on the exterior of the pressure-wave reflective element reduces or prevents the balloon catheter from expanding and contracting the arterial wall while simultaneously allowing the laser-induced pressure wave to penetrate the arterial wall and hammer calcium deposits in media.

FIGS. 23A-2D use similar numeric values, but the different figures include different indicators, such as " and ˇ and combinations thereof, for the numeric values due to the changes occurring within the arterial wall as the calcium in the media is formed and treated, which is progressively illustrated from one figure to the next. For purposes of brevity, certain layers of the arterial wall 2300 are omitted from the discussion of particular figures, and numeric values of certain items of the arterial wall 2300 are omitted from the particular figures. Nevertheless, one should consider the layers of the arterial wall 2300, and the formations therein, to have the same numeric values even if omitted from FIGS. 23A-23D.

Figure 24:
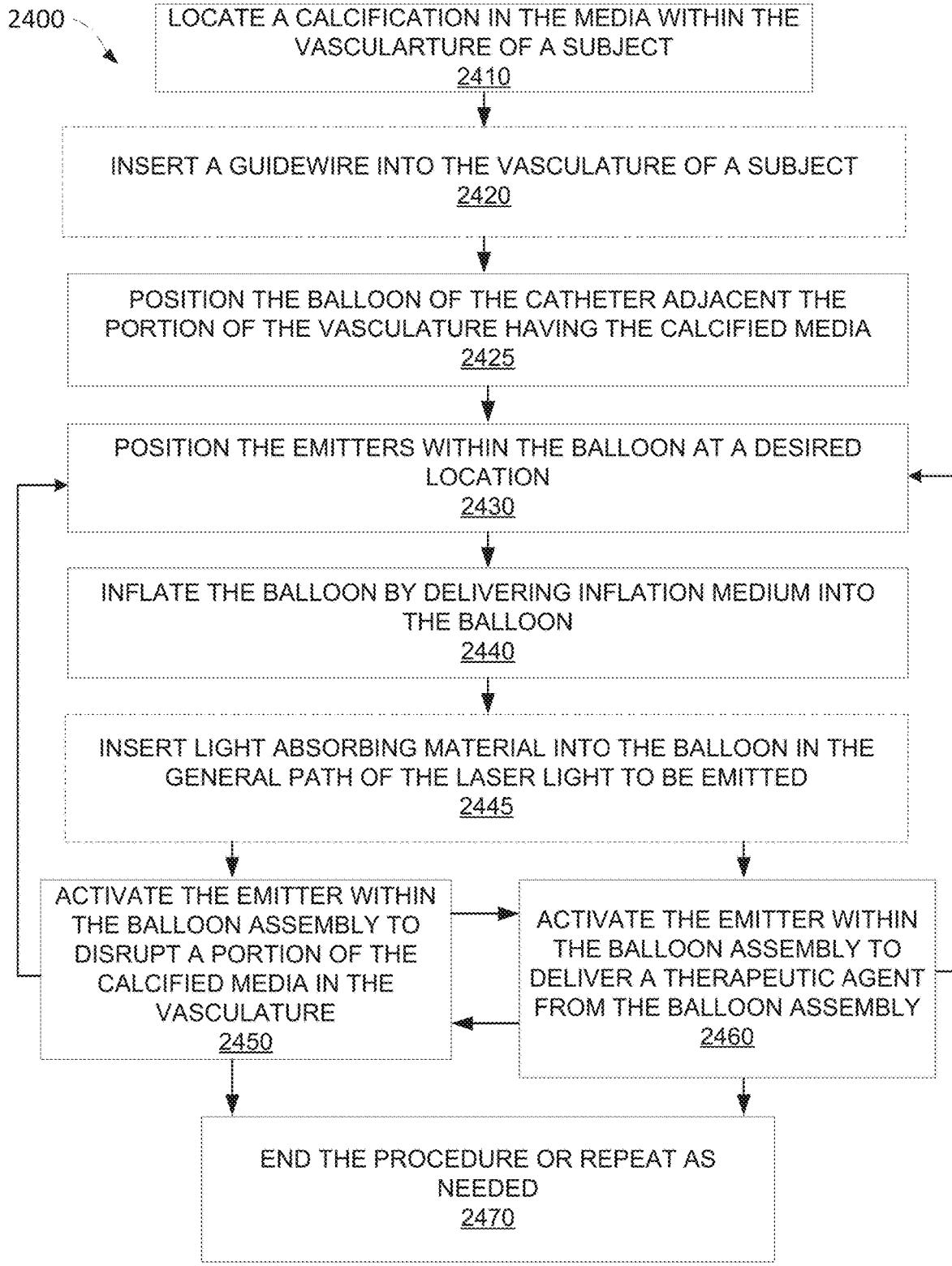
FIG. 24 is a method of using a laser-induced balloon catheter to treat the calcified media.

Referring to FIG. 24, there is depicted a method 2400 of using a catheter to generate laser-induced pressure waves to treat the calcium deposits in the media by disrupting the calcium deposits to increase vasculature compliance, thereby increasing blood flow therethrough. This method 2400 may be used to treat calcium deposits in the media of coronary arteries and/or peripheral arteries. The method 2400 in FIG. 24 includes locating a calcification in the media within the vasculature of a subject at step 2410. The next step 2420, which is optional, includes locating a guidewire at the occlusion and/or inserting a guidewire through the occlusion or through the passageway past the portion of the vasculature that includes the calcified portion(s) in the media.

After locating the calcified portion(s) in the media within the vasculature, step 2425 may then be performed. Step 2425 includes positioning a balloon catheter of the present disclosure adjacent the vasculature that includes the calcified portion(s) in the media. For example, if a clinician uses a catheter 100, 800, 1000 or any other catheter described herein, which have a guidewire lumen, the catheter(s) may be slid over the guidewire and into the vasculature such that the balloon catheter, which is coupled to the catheter(s), is positioned adjacent to the vascular obstruction or restriction (or remainder thereof). At step 2430, the emitters included with the laser catheter are positioned (and subsequently re-positioned) at any desired location along the length of the balloon. The method 2400 also includes step 2440, which comprises inflating the balloon catheter by delivering the liquid medium (for example, contrast medium) from the inner lumen of the catheter through one or more liquid medium ports and into the balloon catheter 1050. Additionally or alternatively, the method may include step 2445, which includes inserting additional light absorbing material into the balloon catheter in the general path of the laser light to be emitted. In some cases, the method 2400 includes the step 2450 of activating at least one energy source coupled to at least one emitter enclosed within the balloon of the balloon catheter to crack the calcified portion(s) in the media and/or breaks the calcified portions into smaller particles. Disrupting the calcified portion(s) within the media cracks the calcified portion(s) because the laser-induced pressure waves are absorbed by the calcified portions. In some cases, the method 2400 includes the step 2460 of activating at least one energy source coupled to at least one emitter enclosed within the balloon of the balloon catheter to emit and send pulses of laser light energy into and/or to react with the liquid medium to produce propagating laser-induced pressure waves to deliver a therapeutic agent to through the cracks in the calcified portions through the cracks in the calcified portions and/or through (or to) potentially.

Referring again to step 2450 of method 2400 in FIG. 24, the emission of propagating laser-induced pressure waves from the balloon catheter into the calcified portions in the media disrupts the calcified portion(s) in the media. Disrupting the calcified portion(s) within the media cracks the calcified portion and/or reduces the size of the calcified portion(s) because the laser-induced pressure waves are absorbed by the calcified portion(s), thereby increasing the arterial wall's compliance, which in turn leads to improved blood flow and positive implications for other health conditions.

EXAMPLES

Example 1

Vascular Testing: Improved Arterial Wall Compliance

An example of the benefit of using a laser-induced balloon catheter of the present disclosure is as follows. Using optical coherence tomography, a section of an artery from a cadaver, namely the superficial femoral artery to the posterior tibial artery, having calcium segments in both the intima and media was identified. A 5.0 mm balloon catheter was inserted into the artery and inflated to 1 atm while the balloon was located at the relevant segment. Upon inflation to 1 atm, the balloon had a diameter of about 4.90 mm at its largest point of inflation within the artery and about 3.35 mm over a length of 13.3 mm at its minimum point of inflation, which occurred at the location of the occlusion. Moreover, the artery's minimum lumen area (MLA) was about 8.93 mm$^2$, and the diameter stenosis (the minimum lumen diameter divided by the maximum lumen diameter) was about 27.4%. A Spectranetics 2.0 mm over-the-wire (OTW) Turbo-Elite™ laser atherectomy catheter was inserted into the balloon which was filled to 1 atm with a solution comprising 50% saline solution and 50% contrast media. The Turbo-Elite™ laser atherectomy catheter produced pulsed laser light at 1 Hz and produced 50 mJ of energy per pulse for about 40 to 50 pulses while translating inside the fluid filled balloon. After firing the laser catheter within the fluid filled balloon, the balloon inflated at 1 atm to a diameter of about 5.3 mm at one of its largest points of inflation within the artery and about 4.97 mm over a length of 9.33 mm at its minimum point of inflation. Moreover, the artery's minimum lumen area (MLA) was about 19.54 mm$^2$, and the diameter stenosis (the minimum lumen diameter divided by the maximum lumen diameter) was about 10.5%. Accordingly, using the minimum lumen area (MLA) was increased about 131%, namely from about 8.93 mm$^2$ to about 19.54 mm$^2$, and the diameter of the artery at the occlusion increased about 52%, namely from about 3.35 mm to about 4.90 mm.

Treatment using a laser-induced balloon catheter significantly improved tissue compliance.

Example 2

Vascular Testing: Improved Arterial Wall Compliance at Reduced Inflation Pressure Another example of the benefit of using a laser-induced balloon catheter of the present disclosure is as follows. An angioplasty balloon was used as a control. Using optical coherence tomography, a section of an artery from a cadaver having calcium segments in both the intima and media was identified. A 6 mm balloon catheter was inserted into the identified section of the artery and inflated to 1 atm while the balloon was located at the relevant arterial segment. Upon inflation to 1 atm, the balloon had a mean diameter of about 1.92 mm and a cross sectional area of about 2.91 mm$^2$. The balloon catheter was then inflated to 6 atm, which is a "nominal" pressure for treating a stenosed artery. Upon reaching this inflation pressure, the balloon had a mean diameter of 3.50 mm and covered a cross sectional area of the artery equating to about 9.67 mm$^2$.

The same 6 mm balloon was inserted into a different section of an artery from a cadaver having calcium segments in both the intima and media was identified. A similarly sized angioplasty balloon catheter was then inserted into a more distal segment of the same calcified artery and inflated to 1 atm, while the balloon was located at the relevant arterial segment. Upon inflation to 1 atm, the balloon had a mean diameter of about 1.92 mm and an area of about 2.90 mm$^2$, very similar to the previously treated segment. The balloon catheter was then inflated to 1 atm, and upon reaching this inflation pressure, the balloon had a mean diameter of 3.5 mm and covered a cross sectional area of the artery equating to about 9.67 mm$^2$. The angioplasty balloon catheter was then removed from the artery. Subsequently, a Spectranetics 2.0 mm over-the-wire (OTW) Turbo-Elite™ laser atherectomy catheter was inserted into the balloon. The balloon was filled to 1 atm with a solution comprising 50% saline solution and 50% contrast media. The Turbo-Elite™ laser atherectomy catheter produced pulsed laser light at 1 Hz and produced 30 mJ of energy per pulse for 15 pulses while translating inside the fluid filled balloon. The laser atherectomy catheter was removed from the balloon. After firing the laser catheter within the fluid filled balloon, the fluid filled balloon was removed from the arterial section, and the previously inserted angioplasty balloon catheter was reinserted and inflated. Specifically, the balloon catheter was inflated to a pressure of 4 atm. At this pressure the diameter of the balloon expanded to about 3.23 mm and had a cross sectional area of about 8.34 mm$^2$. All measurements were taken using optical coherence tomography. After treatment with the laser-induced pressure wave, the balloon expanded within the calcified artery, and the fluid filled angioplasty balloon was able to expand to a similar diameter within an artery having calcified media but required less pressure to do so—about one-third the amount of inflation pressure.

Treatment using a laser-induced pressure wave inside a balloon significantly reduced the amount of pressure required to dilate an artery with a calcified media.

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, for example, for improving performance, achieving ease and \ or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for improving the compliance of a blood vessel within a subject, the method comprising:
   locating a calcified portion in the media of the blood vessel of the subject;
   positioning a catheter within the blood vessel, the catheter comprising:
      a tube having a lumen, a proximal end and a distal end;
      one or more emitters arranged around or adjacent to the lumen, wherein the one or more emitters have respective distal ends disposed adjacent the distal end of the tube;
      a balloon circumferentially arranged around a portion of the distal end of the tube; and
      one or more liquid medium ports disposed about the catheter and within the balloon;
   positioning the balloon adjacent the calcified portion in the media;
   inflating the balloon by delivering a liquid medium through the lumen of the tube and out the one or more liquid medium ports into the balloon until a desired inflation pressure is obtained; and
   emitting one or more pulses of light energy from the distal ends of the one or more emitters, wherein the one or more pulses of light energy reacts with the liquid medium and generates a plurality of propagating laser-induced pressure waves that disrupt the calcified portion in the media, thereby improving the compliance of the blood vessel, and wherein the one or more pulses of light energy comprise a wavelength of between about 300 nanometers to about 350 nanometers, at pulse durations between about 100 nanoseconds to about 150 nanoseconds, and at frequencies between about 1 pulse per second to about 250 pulses per second.

2. The method of claim 1, wherein the liquid medium is any one of iodine-containing contrast medium or gadolinium contrast medium.

3. The method of claim 1, wherein the inflation pressure obtained by delivering liquid medium into the balloon is between about 0.25 atmospheres and about 5.0 atmospheres of pressure.

4. The method of claim 1, wherein the plurality of propagating laser-induced pressure waves enhances penetration of one or more therapeutic agents into the media.

5. The method of claim 1, wherein the one or more therapeutic agents comprises one or more oxidation-insensitive drugs in a polymer-free drug preparation.

6. The method of claim 5, wherein the one or more oxidation-insensitive drugs is one or more of taxanes, thalidomide, statins, corticoids, and lipophilic derivatives of corticoids.

7. The method of claim 4, wherein total energy output for the one or more pulses of light energy comprises energy between about 30 to about 80 millijoules per millimeter squared ($mJ/mm^2$).

8. A method for improving the compliance of a blood vessel within a subject, the method comprising:
   locating a calcified portion in the media of the blood vessel of the subject;
   positioning a catheter within the blood vessel, the catheter comprising:
      a tube having a lumen, a proximal end and a distal end;
      one or more emitters arranged around or adjacent to the lumen, wherein the one or more emitters have respective distal ends disposed adjacent the distal end of the tube;
      a balloon circumferentially arranged around a portion of the distal end of the tube; and
      one or more liquid medium ports disposed about the catheter and within the balloon;
   positioning the balloon adjacent the calcified portion in the media;
   inflating the balloon by delivering a liquid medium through the lumen of the tube and out the gone or more liquid medium ports into the balloon until a desired inflation pressure is obtained; and
   emitting one or more pulses of light energy from the distal ends of the one or more emitters, wherein the one or more pulses of light energy reacts with the liquid medium and generates a plurality of propagating laser-induced pressure waves that disrupt the calcified portion in the media, thereby improving the compliance of the blood vessel, wherein the one or more pulses of light energy comprises a wavelength a—of about 308 nanometers, at pulse durations between about 120 nanoseconds and about 140 nanoseconds, and at frequencies between about 25 pulses per second to about 80 pulses per second, and wherein the plurality of propagating laser-induced pressure waves enhances penetration of one or more therapeutic agents into the media.

9. A method for disrupting a calcified portion contained within the media of a blood vessel wall of a subject, the method comprising:
 positioning a catheter within a blood vessel of the subject, the catheter comprising:
  a tube having a guidewire lumen, an inflation lumen, a proximal end and a distal end;
  a plurality of emitters circumferentially arranged around or adjacent to the guidewire lumen, wherein at least a portion of the plurality of emitters comprises a distal end;
  a balloon circumferentially arranged around a portion of the tube and around at least a portion of the distal end of the plurality of emitters;
  one or more liquid medium ports disposed within the tube and within the balloon; and
  a pressure-wave reflective element disposed adjacent the balloon;
 positioning the balloon adjacent the calcified portion within the media of the blood vessel wall;
 inflating the balloon by delivering a liquid medium through the inflation lumen and out the one or more liquid medium ports into the balloon until a desired inflation pressure is obtained; and
 emitting one or more pulses of light energy from the distal end of the plurality of emitters, whereupon the one or more pulses of light energy reacts with the liquid medium and generates one or more laser-induced pressure waves that propagate through the balloon and disrupt the calcified portion within the media, and wherein the one or more pulses of light energy comprise a wavelength of between about 300 nanometers to about 350 nanometers, at pulse durations between about 100 nanoseconds to about 150 nanoseconds, and at frequencies between about 1 pulse per second to about 250 pulses per second.

10. The method of claim 9, wherein the pressure-wave reflective element comprises a plurality of openings.

11. The method of claim 10, wherein the plurality of openings are between 10 microns and 10 millimeters.

12. The method of claim 10, wherein a percentage of the plurality of openings within an area of a portion of the pressure-wave reflective element is between 10 percent and 90 percent.

13. The method of claim 10, wherein an area of the pressure-wave reflective element comprises the plurality of openings and a structural mass, wherein a ratio of an area of the plurality of openings to an area of the structural mass within the area of the pressure-wave reflective element is between 10:1 and 1:10.

14. The method of claim 10, wherein the plurality of openings comprise at least one of the following shapes: circle; oval; triangle; square; rectangle; polygon; diamond; pentagon; hexagon; heptagon; octagon; nonagon; and decagon.

15. The method of claim 14, further comprising the step of re-positioning the balloon such that the balloon is adjacent another calcified portion in the media within the blood vessel wall.

16. The method of claim 15, further comprising the step of moving the plurality of emitters within the balloon.

17. The method of claim 16, wherein the plurality of emitters is re-positioned within the pressure-wave reflective element.

18. The method of claim 10, further comprising the step of re-positioning the plurality of emitters within the balloon.

19. The method of claim 10, wherein the plurality of emitters is re-positioned within the pressure-wave reflective element.

\* \* \* \* \*